(12) United States Patent
Larson et al.

(10) Patent No.: US 10,849,977 B2
(45) Date of Patent: *Dec. 1, 2020

(54) LIQUID PROTEIN FORMULATIONS CONTAINING THIAMINE

(71) Applicant: Eagle Biologics, Inc., Woodcliff Lake, NJ (US)

(72) Inventors: Alyssa M. Larson, Dana Point, CA (US); Kevin Love, Boston, MA (US); Alisha K. Weight, Mill Creek, WA (US); Alan Crane, Waban, MA (US); Robert S. Langer, Newton, MA (US); Alexander M. Klibanov, Boston, MA (US)

(73) Assignee: EAGLE BIOLOGICS, INC., Woodcliff Lake, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/903,635

(22) Filed: Feb. 23, 2018

(65) Prior Publication Data

US 2018/0177876 A1 Jun. 28, 2018

Related U.S. Application Data

(63) Continuation of application No. 14/484,160, filed on Sep. 11, 2014, now Pat. No. 9,925,263.

(60) Provisional application No. 62/030,521, filed on Jul. 19, 2014, provisional application No. 62/026,497, filed on Jul. 18, 2014, provisional application No. 62/008,050, filed on Jun. 5, 2014, provisional application No. 61/988,005, filed on May 2, 2014, provisional application No. 61/946,436, filed on Feb. 28, 2014, provisional application No. 61/943,197, filed on Feb. 21, 2014, provisional application No. 61/940,227, filed on Feb. 14, 2014, provisional application No. 61/876,621, filed on Sep. 11, 2013.

(51) Int. Cl.

| | | |
|---|---|---|
| A61K 39/395 | (2006.01) | |
| A61K 47/06 | (2006.01) | |
| A61K 9/19 | (2006.01) | |
| C07K 16/32 | (2006.01) | |
| A61K 47/24 | (2006.01) | |
| A61K 9/00 | (2006.01) | |
| A61K 47/20 | (2006.01) | |
| A61K 47/22 | (2006.01) | |
| C07K 16/22 | (2006.01) | |
| C07K 16/24 | (2006.01) | |
| C07K 16/28 | (2006.01) | |
| A61K 38/00 | (2006.01) | |

(52) U.S. Cl.

CPC .......... *A61K 47/06* (2013.01); *A61K 9/0019* (2013.01); *A61K 9/19* (2013.01); *A61K 39/3955* (2013.01); *A61K 47/20* (2013.01); *A61K 47/22* (2013.01); *A61K 47/24* (2013.01); *C07K 16/22* (2013.01); *C07K 16/241* (2013.01); *C07K 16/2839* (2013.01); *C07K 16/2863* (2013.01); *C07K 16/2887* (2013.01); *C07K 16/32* (2013.01); *A61K 38/00* (2013.01)

(58) Field of Classification Search
None
See application file for complete search history.

(56) References Cited

U.S. PATENT DOCUMENTS

| | | |
|---|---|---|
| 3,682,174 A | 8/1972 | Cohen |
| 4,092,410 A | 5/1978 | Ogata et al. |
| 4,171,698 A | 10/1979 | Genese |
| 4,816,567 A | 3/1989 | Cabilly et al. |
| 5,001,000 A | 3/1991 | Rohrbacher et al. |
| 5,034,506 A | 7/1991 | Summerton et al. |
| 5,142,047 A | 8/1992 | Summerton et al. |
| 5,166,315 A | 11/1992 | Summerton et al. |
| 5,168,062 A | 12/1992 | Stinski |
| 5,217,866 A | 6/1993 | Summerton et al. |
| 5,334,162 A | 8/1994 | Harris |
| 5,356,802 A | 10/1994 | Chandrasegaran |
| 5,385,839 A | 1/1995 | Stinski |
| 5,436,150 A | 7/1995 | Srinivasan |
| 5,454,786 A | 10/1995 | Harris |

(Continued)

FOREIGN PATENT DOCUMENTS

| | | |
|---|---|---|
| CN | 1789575 A | 6/2006 |
| CN | 1798575 | 7/2006 |

(Continued)

OTHER PUBLICATIONS

Costantini et al., Effects of Overdose of High-Dose thiamine treatmenst, Gerentology and Geriatric Studies, vol. 4, p. 389-390, 2018.*

(Continued)

*Primary Examiner* — Yunsoo Kim
(74) *Attorney, Agent, or Firm* — BakerHostetler

(57) ABSTRACT

Concentrated, low-viscosity, low-volume liquid pharmaceutical formulations of proteins have been developed. Such formulations can be rapidly and conveniently administered by subcutaneous or intramuscular injection, rather than by lengthy intravenous infusion. These formulations include low-molecular-weight and/or high-molecular-weight proteins, such as mAbs, and viscosity-lowering agents that are typically bulky polar organic compounds, such as many of the GRAS (US Food and Drug Administration List of compounds generally regarded as safe) and inactive injectable ingredients and FDA approved therapeutics.

20 Claims, 7 Drawing Sheets

(56) References Cited

U.S. PATENT DOCUMENTS

| | | |
|---|---|---|
| 5,487,994 A | 1/1996 | Chandrasegaran |
| 5,506,337 A | 4/1996 | Summerton et al. |
| 5,521,063 A | 5/1996 | Coull et al. |
| 5,527,675 A | 6/1996 | Coull et al. |
| 5,539,082 A | 7/1996 | Nielsen et al. |
| 5,569,193 A | 10/1996 | Hofstetter et al. |
| 5,608,038 A | 3/1997 | Eibl et al. |
| 5,623,049 A | 4/1997 | Loebberding et al. |
| 5,641,870 A | 6/1997 | Rinderknecht et al. |
| 5,698,195 A | 12/1997 | Le et al. |
| 5,698,685 A | 12/1997 | Summerton et al. |
| 5,714,331 A | 2/1998 | Buchardt et al. |
| 5,730,978 A | 3/1998 | Wayner |
| 5,736,137 A | 4/1998 | Anderson et al. |
| 5,736,336 A | 4/1998 | Buchardt et al. |
| 5,773,571 A | 6/1998 | Nielsen et al. |
| 5,779,668 A | 7/1998 | Grabenkort |
| 5,786,571 A | 7/1998 | Bethel et al. |
| 5,819,988 A | 10/1998 | Sawhney et al. |
| 5,819,998 A | 10/1998 | Chehebar |
| 5,821,337 A | 10/1998 | Carter et al. |
| 5,840,299 A | 11/1998 | Bendig et al. |
| 5,871,736 A | 2/1999 | Bruegger et al. |
| 5,962,405 A | 10/1999 | Seelich |
| 6,033,665 A | 3/2000 | Yednock |
| 6,054,297 A | 4/2000 | Carter et al. |
| 6,065,645 A | 5/2000 | Sawhney et al. |
| 6,171,586 B1 | 1/2001 | Lam et al. |
| 6,184,037 B1 | 2/2001 | Rolland et al. |
| 6,217,866 B1 | 4/2001 | Sela et al. |
| 6,235,883 B1 | 5/2001 | Jakobovits et al. |
| 6,252,055 B1 | 6/2001 | Relton |
| 6,267,958 B1 | 7/2001 | Andya et al. |
| 6,394,314 B1 | 5/2002 | Sawhney et al. |
| 6,443,612 B1 | 9/2002 | Keller |
| 6,457,609 B1 | 10/2002 | Keller |
| 6,525,102 B1 | 2/2003 | Chen et al. |
| 6,551,840 B2 | 4/2003 | Ono et al. |
| 6,564,972 B2 | 5/2003 | Sawhney et al. |
| 6,602,503 B1 | 8/2003 | Lobb et al. |
| 6,685,940 B2 | 2/2004 | Andya et al. |
| 6,698,622 B2 | 3/2004 | Sawhney et al. |
| 6,730,328 B2 | 5/2004 | Maskiewicz et al. |
| 6,875,432 B2 | 4/2005 | Liu et al. |
| 7,030,097 B1 | 4/2006 | Saltzman et al. |
| 7,390,786 B2 | 6/2008 | Warne et al. |
| 7,501,000 B2 | 3/2009 | Rosenflanz et al. |
| 7,666,413 B2 | 2/2010 | Liu et al. |
| 7,740,842 B2 | 6/2010 | Arvinte et al. |
| 7,758,860 B2 | 7/2010 | Warne et al. |
| 8,142,776 B2 | 3/2012 | Liu et al. |
| 8,383,114 B2 | 2/2013 | Sloey et al. |
| 8,476,239 B2 | 7/2013 | Dali et al. |
| 8,500,681 B2 | 8/2013 | Gonnelli et al. |
| 8,703,126 B2 | 4/2014 | Liu et al. |
| 8,715,651 B2 | 5/2014 | Maestro et al. |
| 8,779,094 B2 | 7/2014 | Johnston et al. |
| 8,802,095 B2 | 8/2014 | Houston et al. |
| 8,906,368 B2 | 12/2014 | Bolli et al. |
| 9,072,668 B2 | 7/2015 | Dai et al. |
| 9,084,743 B2 | 7/2015 | Teschner et al. |
| 9,084,777 B2 | 7/2015 | Morichika et al. |
| 9,309,316 B2 | 4/2016 | Dali et al. |
| 9,320,797 B2 | 4/2016 | Sloey et al. |
| 9,457,089 B2 | 10/2016 | Soula |
| 9,605,051 B2 | 3/2017 | Soane et al. |
| 9,669,242 B2 | 6/2017 | Chen et al. |
| 9,677,061 B2 | 6/2017 | Bookbinder et al. |
| 9,771,427 B2 | 9/2017 | Hofer et al. |
| 2002/0190082 A1 | 12/2002 | Keller |
| 2003/0113316 A1 | 6/2003 | Kaisheva et al. |
| 2004/0191243 A1 | 9/2004 | Chen et al. |
| 2004/0197324 A1 | 10/2004 | Liu et al. |
| 2004/0247672 A1 | 12/2004 | Tracy et al. |
| 2005/0019337 A1 | 1/2005 | Ryall |
| 2005/0158303 A1 | 7/2005 | Liu et al. |
| 2006/0142234 A1 | 6/2006 | Chen et al. |
| 2007/0053900 A1 | 3/2007 | Liu et al. |
| 2007/0065373 A1 | 3/2007 | Morton et al. |
| 2007/0093462 A1 | 4/2007 | Rogers et al. |
| 2007/0172479 A1 | 7/2007 | Warne et al. |
| 2007/0172517 A1 | 7/2007 | Ben-Sasson et al. |
| 2007/0184084 A1 | 8/2007 | Chen et al. |
| 2008/0071063 A1 | 3/2008 | Allan et al. |
| 2008/0226689 A1 | 9/2008 | Berry et al. |
| 2008/0248991 A1 | 10/2008 | Dyer et al. |
| 2009/0280129 A1 | 11/2009 | Liu et al. |
| 2010/0061949 A1 | 3/2010 | Schmidt-Jacobsen et al. |
| 2010/0136062 A1 | 6/2010 | Fernandez et al. |
| 2010/0239567 A1 | 9/2010 | Esue |
| 2011/0065675 A1 | 3/2011 | Buchwald et al. |
| 2011/0145940 A1 | 6/2011 | Voytas et al. |
| 2011/0212094 A1 | 9/2011 | Ghayur et al. |
| 2011/0262626 A1 | 10/2011 | Sun et al. |
| 2011/0305734 A1 | 12/2011 | Edelson et al. |
| 2012/0148556 A1 | 6/2012 | Lebowitz et al. |
| 2012/0230982 A1 | 9/2012 | Zhou et al. |
| 2012/0231009 A1 | 9/2012 | Ramani et al. |
| 2012/0263783 A1 | 10/2012 | Messmer |
| 2013/0028907 A1 | 1/2013 | Parshad et al. |
| 2013/0028920 A1 | 1/2013 | Gurny et al. |
| 2013/0058958 A1 | 3/2013 | Bowen et al. |
| 2013/0171128 A1 | 7/2013 | Huang et al. |
| 2013/0216525 A1 | 8/2013 | Chen |
| 2013/0216556 A1 | 8/2013 | Fowler et al. |
| 2013/0309226 A1 | 11/2013 | Armstrong et al. |
| 2013/0317457 A1 | 11/2013 | Schmitt et al. |
| 2014/0023655 A1 | 1/2014 | Monck et al. |
| 2014/0127227 A1 | 5/2014 | Chang |
| 2014/0294859 A1 | 10/2014 | Sloey et al. |
| 2014/0378370 A1 | 12/2014 | Johnston et al. |
| 2014/0378655 A1 | 12/2014 | Anderson |
| 2015/0044198 A1 | 2/2015 | Liu et al. |
| 2015/0071920 A1 | 3/2015 | Larson et al. |
| 2015/0150979 A1 | 6/2015 | Yates et al. |
| 2015/0209431 A1 | 7/2015 | Ma et al. |
| 2015/0225485 A1 | 8/2015 | Liu et al. |
| 2015/0284466 A1 | 10/2015 | Morichika et al. |
| 2016/0002624 A1 | 1/2016 | Dibble et al. |
| 2016/0074515 A1 | 3/2016 | Soane et al. |
| 2016/0090419 A1 | 3/2016 | Morichika et al. |
| 2016/0193346 A1 | 7/2016 | Houston et al. |
| 2016/0367675 A1 | 12/2016 | Liu et al. |
| 2017/0049888 A1 | 2/2017 | Liu et al. |

FOREIGN PATENT DOCUMENTS

| | | |
|---|---|---|
| CN | 101061185 | 10/2007 |
| CN | 102573459 A | 7/2012 |
| EP | 1981824 A2 | 10/2008 |
| EP | 2335725 A1 | 6/2011 |
| EP | 2538973 A2 | 1/2013 |
| GB | 0750373 A | 6/1956 |
| GB | 1231494 A | 5/1971 |
| JP | 03-190823 A | 8/1991 |
| JP | 08-173533 A | 7/1996 |
| JP | 2003-129666 A | 5/2003 |
| JP | 2004-002429 A | 1/2004 |
| JP | 2006-523461 | 10/2006 |
| JP | 2007-523050 | 8/2007 |
| JP | 2009-511497 | 3/2009 |
| JP | 2010-505773 | 2/2010 |
| JP | 2010-124827 A | 6/2010 |
| JP | 2013-509189 A | 3/2013 |
| JP | 2013-525484 | 6/2013 |
| JP | 2013-528570 | 7/2013 |
| JP | 2015-508774 A | 3/2015 |
| RU | 2485133 | 6/2013 |
| WO | 99/18994 A1 | 4/1999 |
| WO | 02/44321 A2 | 6/2002 |
| WO | 2002/092014 A2 | 11/2002 |
| WO | 2003/101479 | 12/2003 |
| WO | 2004/089335 A2 | 10/2004 |
| WO | 2004/092361 A1 | 10/2004 |

(56) References Cited

FOREIGN PATENT DOCUMENTS

| | | | |
|---|---|---|---|
| WO | 2006/071693 | A2 | 7/2006 |
| WO | 2007/088110 | A2 | 8/2007 |
| WO | 2007/138014 | A1 | 12/2007 |
| WO | 2008/092084 | A2 | 7/2008 |
| WO | 2009/015367 | A2 | 1/2009 |
| WO | 2009/026122 | A1 | 2/2009 |
| WO | 2009/043049 | A2 | 4/2009 |
| WO | 2009/120684 | | 10/2009 |
| WO | 2009/141397 | | 11/2009 |
| WO | 2010/132047 | A1 | 11/2010 |
| WO | 2011/069037 | A2 | 6/2011 |
| WO | 2011/072246 | A2 | 6/2011 |
| WO | 2011/095543 | A1 | 8/2011 |
| WO | 2011/104381 | A2 | 9/2011 |
| WO | 2011/109415 | A2 | 9/2011 |
| WO | 2011/116090 | | 9/2011 |
| WO | 2011/139718 | A1 | 11/2011 |
| WO | 2012/010832 | A1 | 1/2012 |
| WO | 2012/141978 | A2 | 10/2012 |
| WO | 2013/063275 | | 5/2013 |
| WO | 2013/096791 | A1 | 6/2013 |
| WO | 2013/112986 | A1 | 8/2013 |
| WO | 2013/123114 | A2 | 8/2013 |
| WO | 2013/176772 | A1 | 11/2013 |
| WO | 2014/018423 | A2 | 1/2014 |
| WO | 2014/023816 | A1 | 2/2014 |
| WO | 2015/038777 | | 3/2015 |
| WO | 2015/038782 | | 3/2015 |
| WO | 2015/038811 | | 3/2015 |
| WO | 2015/038818 | | 3/2015 |

OTHER PUBLICATIONS

Zapata et al., Engineering linear F (ab') 2 fragments for efficient production in *Escherichia coli* and enhanced antiproliferative activity. Protein Engineering, Design and Selection. Oct. 1, 1995;8(10):1057-1062.
Yip et al, Therapeutic value of glycosaminoglycans in cancer, Molecular cancer therapeutics 5.9, Sep. 2006, 2139-2148.
Wasser et al., "Therapeutic Effects of Substances Occurring in Higher Basidiomycetes Mushrooms: A Modern Perspective" Critical Reviews in Immunology, 1999,19, pp. 65-96.
Wang, Monoclonal antibody pharmacokinetics and pharmacodynamics. Clinical Pharmacology & Therapeutics. Nov. 1, 2008;84(5):548-558.
Wang et al., "Antibody Structure, Instability, and Formulation" Journal of Pharmaceutical Sciences, vol. 96, Jan. 2007, pp. 1-26.
Vazquez-Rey, "Aggregates in Monoclonal Antibody Manufacturing Processes" Biotechnology and Bioengineering, Jul. 2011, vol. 108, No. 7., pp. 1494-1508.
Van Rantwijk et al., "Biocatalysis in Ionic Liquids" Chem. Rev., 2007,107, pp. 2757-2785.
Ui-Tei et al., "Sensitive Assay of RNA Interference in *Drospohila* and Chinese Hamster Cultured Cells Using Firefly Luciferase Gene as Target", FEBS letters 479, 2000, pp. 79-82.
Tzianabos, "Polysaccharide Immunomodulators as Therapeutic Agents: Structural Aspects and Biologic Function" Clinical Microbiology Reviews, Oct. 2000, pp. 523-533.
Sutherland, Biotechnology of microbial exopolysaccharides, Cambridge University Press; 1990, pp. 70-88.
Stirchak et al., "Uncharged Stereoregular Nucleic Acid Analogues. 1. Synthesis of a Cytosine-continaing Oligomer with Carbamate Internucleoside Linkages" Organic. Chem., 1987, pp. 4202-4206.
Srinivasan et al., "Non-Aqueous Suspensions of Antibodies are Much Less Viscous Than Equally Concentrated Aqueous Solutions" Pharm Res, 2013, 30, pp. 1749-1757.
Smith et al., "Nucleic Acid Nanostructures for Biomedical Applications", Nanomedicine, 2013, pp. 105-121.
Shire et al., "Challenges in the Development of High Protein Concentration Formulations" Journal of Pharmaceutical Sciences, Jul. 2004, vol. 93, pp. 1390-1402.
Sheldon et al., "Biocatalysts in Ionic Liquids" Green Chem., 2002, 4, pp. 147-151.
Scolnik, mAbs: a business perspective. InMAbs Mar. 1, 2009 (vol. 1, No. 2, pp. 179-184). Taylor & Francis.
Roy et al., "Effect of Hydrotropes on Solution Behaviour of Amphiphiles" Current Science, vol. 85, No. 8, Oct. 25, 2003, pp. 1148-1155.
Riduan et al., "Imidazolium Salts and Their Polymeric Materials for Biological Applications" Chem. Soc. Rev., 2013 42, pp. 9055-9070.
Remington: "The Science and Practice of Pharmacy", 20th Edition, Alfonso R. Gennaro, Ed., Lippincott Williams & Wilkins, Copyright 2000,18 Pages.
Reichmann et al., Reshaping human antibodies for therapy, Nature 332:323-329, 1988.
Reichert, Which are the antibodies to watch in 2013?. InMAbs Jan. 1, 2013 (vol. 5, No. 1, pp. 1-4). Taylor & Francis.
Presta, Antibody engineering. Current Opinion in Structural Biology. Aug. 1, 1992;2(4):593-596.
Pearlman, Peptide and Protein Drug Delivery, 247-301, Vincent Lee, Ed., Marcel Dekker, Inc., New York, N.Y. (1991).
Pathak et al., "Do Clustering Monoclonal Antibody Solutions Really Have a Concentration Dependence of Viscosity?", Biophysical Journal, vol. 104, Feb. 2013, pp. 913-923.
Patel, Therapeutic Importance of Sulfated Polysaccharides From Seaweeds: Updating the Recent Findings. 3 Biotech, 2012, pp. 171-185.
Palek et al, "Effect of Procaine HC1 on ATP: Calcium-Dependent Alterations in Red Cell Shape and Deformability" Blood, Jul. 1977, 50(1), pp. 155-164.
Page, Heparin and related drugs: beyond anticoagulant activity, ISRN pharmacology, 2013, 14 pages.
Ober et al, Differences in promiscuity for antibody—FcRn interactions across species: implications for therapeutic antibodies. International immunology. Dec. 1, 2001;13(12)1551-1559.
Nykanen et al., "ATP Requirements and Small Interfering RNA Structure in the RNA Interference Pathway" Cell, vol. 107, Nov. 2, 2001, pp. 309-321.
Napoli et al., "Introduction of a Chimeric Chalcone Synthase Gene Into Petunia Results in Reversible Co-Suppression of Homologous Genes in Trans", 1990, Plant Cell, pp. 279-289.
Morrison et al., Chimeric antibody molecules: mouse antigen-binding domains with human constant region domains. Proceedings of the National Academy of Sciences. Nov. 1, 1984;81(21):6851-6855.
Miller et al., "Low Viscosity Highly Concentrated Injectable Nonaqueous Suspensions of Lysozyme Microparticles", Langmuir, Jan. 19, 2010, pp. 1067-1074.
Miller et al., "A Tale Nuclease Architecture for Efficient Genome Editing" Nature Biotechnol, Feb. 2011, 8 Pages.
Martinez et al., "Single-Stranded Antisense siRNAs Guide Target RNA Cleavage in RNAi" Cell, Sep. 6, 2002, pp. 563-574.
Marks et al., By-passing immunization: human antibodies from V-gene libraries displayed on phage. Journal of molecular biology. Dec. 5, 1991;222(3):581-597.
Mallin, "Properties of Contractile Protein from Bovine Carotid Artery" J. Cell, and Comp. Physiol., Jun. 1965, pp. 355-360.
Li et al., "Functional Domains in Fok I Restriction Endonuclease" Proc., Natl. Acad. Sci. USA, May 1992, pp. 4275-4279.
Li et al., "Alteration of the Cleavage Distance of Fok I Restriction Endonuclease by Insertion Mutagenesis" Proc. Natl. Acad. Sci. USA, Apr. 1993, pp. 2764-2768.
Lee, Changing needs in drug delivery in the era of peptide and protein drugs. Peptide and protein drug delivery. 1991;1:1-56.
Larson, "Bulky Polar Additives That Greatly Reduce the Viscosity of Concentrated Solutions of Therapeutic Monoclonal Antibodies", Journal of Pharmaceutical Sciences, 2017, pp. 1211-1217.
Köhler, Continuous cultures of fused cells secreting antibody of predefined specificity. Nature. Aug. 1975;256(5517):495-497.
Kivitz et al., "Clinical Assessment of Pain, Tolerability, and Preference of an Autoinjection Pen Versus a Prefilled Syringe for Patient Self-Administration of the Fully Human, Monoclonal Antibody Adalimumab: The Touch Trial" Clinical Therapeutics, Nov. 10, 2006, vol. 28, pp. 1619-1629.

(56) References Cited

OTHER PUBLICATIONS

Kim et al., "Insertion and Deletion Mutants of FokI Restriction Endonuclease" J. Biol. Chem. Dec. 16, 1994, pp. 31978-31982.
Kim et al., "Chimeric Restriction Endonuclease", Proc. Natl. Acad. Sci. USA, Feb. 1994, pp. 883-887.
Kerr, The use of cylexin (CY-1503) in prevention of reperfusion lung injury in patients undergoing pulmonary thromboendarterectomy, American journal of respiratory and critical care medicine, Jul. 1, 2000;162(1):14-20.
Jones, Replacing the complementarity-determining regions in a human antibody with those from a mouse. Nature. May 1986;321(6069):522-525.
Jones, Analysis of polypeptides and proteins. Advanced drug delivery reviews. Jan. 1, 1993;10(1):29-90.
Jinek, et al., "A Programmable Dual-RNA-Guided DNA Endonuclease in Adaptive Bacterial Immunity" Science, Aug. 17, 2012, vol. 337, pp. 816-821.
Jezek, et al., "Viscosity of concentrated therapeutic protein compositions", Adv Drug Deliv Rev., 63:1107-1117 (2011).
Jacobsen et al., "1,1-Dicyano-2[6-(Dimethylamino)naphthalen-2-yl]propene(DDNP): A Solvent Polarity and Viscosity Sensitive Fluorophore for Fluorescene Microscopy", J. Am. Chem. Soc., 1996,118, pp. 5572-5579.
International Search Report issued in PCT/US2014/055254, dated Jun. 29 2015, 4 pages.
International Search Report issued in PCT/US15/53313, dated Dec. 23, 2015; 2 pages.
International Search Report for PCT/US2014/055245 dated May 29, 2015.
International Search Report for PCT/US2014/055210 dated Dec. 10, 2014.
International Search Report for PCT/US2014/055203 dated Dec. 10, 2014.
Hoffman, Conjugates of stimuli-responsive polymers and proteins. Progress in Polymer Science. Aug. 1, 2007;32(8-9):922-932.
Hawe et al., "Fluorescent Molecular Rotors as Dyes to Characterize Polysorbate-Containing IgG Formulations" Pharmaceutical Research, vol. 27, No. 2, Feb. 2010, pp. 314-326.
Harada et al., Chemical Structure of Antithrombin-active Rhamnan Sulfate from Monostrom nitidum. Bioscience, Biotechnology, and Biochemistry, 1998, 62(9), pp. 1647-1652.
Hannon, "RNA Interference" Nature, Jul. 11, 2002, vol. 418, pp. 244-251.
Hammond, "An RNA-Directed Nuclease Mediates Post-Transcriptional Gene Silencing in *Drosophila* Cells", Nature, 2000, 404, pp. 293-296.
Guo et al., "Structure-Activity Relationship for Hydrophobic Salts as Viscosity-Lowering Excipients for Concentrated Solutions of Monoclonal Antibodies" Pharm Res, 2012, 29, pp. 3102-3109.
Guideline on Similar Biological Medicinal Products Containing Biotechnology-Derived Proteins as Active Substance: Quality Issues, European Medicines Agency, Feb. 22, 2006, 8 pages.
Guideline on Non-Clinical and Clinical Development of Similar Biological Medicinal Products Containing Low-Molecular-Weight-Heparins, European Medicines Agency, Nov. 10, 2016, 8 pages.
Fire, Potent and Specific Genetic Interference by Double-Stranded RNA in Caenorhabditis Elegans, Nature, 1998, 391, pp. 806-811.
Federici, Analytical lessons learned from selected therapeutic protein drug comparability studies. Biologicals. May 1, 2013;41(3):131-147.
Ernst, "From Carbohydrate Leads to Glycomimetic Drugs" Nature Reviews Drug Discovery, 2009, 8, pp. 661-677.
Elbashir, "RNA Interference is Mediated by 21- and 22-Nucleotide RNAs", Genes Dev., 2001 15, pp. 188-200.
Elbashir, "Duplexes of 21-Nucleotid RNAs Mediate RNA interference in Cultured Mammalian Cells", Nature, 2001, 111, pp. 494-498.
Earle, Ionic liquids green solvents for the future , Pure Appl. Chem., 72(7):1391-1398 (2000).
Du, Hydrophobic salts markedly diminish viscosity of concentrated protein solutions. Biotechnology and bioengineering. Mar. 1, 2011;108(3):632-636.
Daugherty, Formulation and delivery issues for monoclonal antibody therapeutics. Advanced drug delivery reviews. Aug. 7, 2006;58(5-6):686-706.
Cong, "Multiplex Genome Engineering Using CRISPR/Cas Systems", Science, Feb. 15, 2013, pp. 819-823.
Clackson et al, Making antibody fragments using phage display libraries. Nature. Aug. 1991; 352, 624-628.
Chattopadhyay, "Aqueous Behaviour of Chitosan", International Journal of Polymer Science, 2010, pp. 1-7.
Cermak et al., "Efficient Design and Assembly of Custom TALEN and other TAL Effector-Based Constructs for DNA Targeting" Nucleic Acids Research Jul. 2011, 15 Pages.
Carnes et al., "Plasmid DNA Manufacturing Technology", Recent Patents on Biotechnology, 2007, pp. 1-16.
Buss, Monoclonal antibody therapeutics: history and future. Current opinion in pharmacology. Oct. 1, 2012;12(5):615-622.
Braasch, et al., "Locked Nucleic Acid (LNA): Fine-Tuning the Recognition of DNA and RNA" Chem. Biol., Jan. 2001 8(1), pp. 1-7.
Bernstein, et al., "Role for a Bidentate Ribonuclease in the Initiation Step of RNA Interference", Nature, Jan. 2001, 409, pp. 363-366.
Beck, Biosimilar, biobetter and next generation therapeutic antibodies. InMAbs Mar. 1, 2011 (vol. 3, No. 2, pp. 107-110). Taylor & Francis.
Baumann, Early development of therapeutic biologics-pharmacokinetics. Current drug metabolism. Jan. 1, 2006;7(1):15-21.
Baker et al., "Fluorescence Quenching Immunoassay Performed in an Ionic Liquid" Chem. Commun., 2006, pp. 2851-2853.
Arias et al., "Changes in the Flow Properties of Phospholipid Dispersions Induced by Procaine Dydrochloride. Effect of pH and Temperature" II Farmaco, vol. 56, Jul. 1, 2001, pp. 533-539.
Wei Du et al: "Hydrophobic salts markedly diminish viscosity of concentrated protein solutions", Biotechnolog and Bioengineering, vol. 108, No. 3, Nov. 17, 2010 (Nov. 17, 2010), pp. 632-636, XP055154925.
Kyoko Fujita et al: "Solubility and stability of cytochrome c in hydrated ionic liquids: effect of oxo acid residues and kosmotropicity", Biomacromolecules, American Chemical Society, US, vol. 8, Jan. 1, 2007, pp. 2080-2086, XP002667673.
Daugherty Ann L et al: "Chapter 8: Formulation and delivery issues for monoclonal antibody therapeutics", Jan. 1, 2010 (Jan. 1, 2010), Current Trends in Monoclonal Antibody Development and Manufacturing, Springer, US, p. 103-129, XP009180430.
Ayala Rosanne S et al: "The addition of injectable lidocaine to adalimumab results in decreased injection site pain and increased acceptance of therapy", Arthritis & Rheumatism, Wiley Interscience, US, vol. 58, No. 9, Suppl. S, Aug. 31, 2008 (Aug. 31, 2008), p. S858, XP009505904.
Accessdata FDA, ref. 4407872, p. 1-7.
FDA Report, Clinical Pharmacology and Biopharmaceutics Review for Tagamet, p. 1-33, 1998.
Livak-Dahl, E., Droplet- and Bead-Based Microfluidic Technologies for Rheological and Biochemical Analysis, Ph.D. Thesis, 2013, pp. 1-133.
Malvern, Bohlin CVO Rheological Properties, 2010, pp. 1-4.

\* cited by examiner

Fold improvement in viscosity of solutions of biosimilar Avastin as a function of pH Fold Improvement (viscosity phosphate-citrate buffer / viscosity 0.25 M CSAA)

Viscosities of biosimilar Erbitux as a function of pH and protein concentration with 0.25 M CSAA Viscosity (cP)

LIQUID PROTEIN FORMULATIONS CONTAINING THIAMINE

CROSS-REFERENCE TO RELATED APPLICATIONS

This application is a continuation of U.S. application Ser. No. 14/484,160, filed Sep. 11, 2014, which claims the benefit of U.S. Provisional Application No. 62/030,521, filed Jul. 29, 2014; U.S. Provisional Application No. 62/026,497, filed Jul. 18, 2014; U.S. Provisional Application No. 62/008,050, filed Jun. 5, 2014; U.S. Provisional Application No. 61/988,005, filed May 2, 2014; U.S. Provisional Application No. 61/946,436, filed Feb. 28, 2014; U.S. Provisional Application No. 61/943,197, filed Feb. 21, 2014; U.S. Provisional Application No. 61/940,227, filed Feb. 14, 2014; and U.S. Provisional Application No. 61/876,621, filed Sep. 11, 2013. The disclosure of each of these applications is expressly incorporated herein by reference.

FIELD OF THE INVENTION

The invention is generally in the field of injectable low-viscosity pharmaceutical formulations of highly concentrated proteins and methods of making and using thereof.

BACKGROUND OF THE INVENTION

Monoclonal antibodies (mAbs) are important protein-based therapeutics for treating various human diseases such as cancer, infectious diseases, inflammation, and autoimmune diseases. More than 20 mAb products have been approved by the U.S. Food and Drug Administration (FDA), and approximately 20% of all biopharmaceuticals currently being evaluated in clinical trials are mAbs (Daugherty et al., *Adv. Drug Deliv. Rev.* 58:686-706, 2006; and Buss et al., *Curr. Opinion in Pharmacol.* 12:615-622, 2012).

mAb-based therapies are usually administered repeatedly over an extended period of time and require several mg/kg dosing. Antibody solutions or suspensions can be administered via parenteral routes, such as by intravenous (IV) infusions, and subcutaneous (SC) or intramuscular (IM) injections. The SC or IM routes reduce the treatment cost, increase patient compliance, and improve convenience for patients and healthcare providers during administration compared to the IV route. To be effective and pharmaceutically acceptable, parenteral formulations should preferably be sterile, stable, injectable (e.g., via a syringe), and non-irritating at the site of injection, in compliance with FDA guidelines. Because of the small volumes required for subcutaneous (usually under about 2 mL) and intramuscular (usually under about 5 mL) injections, these routes of administration for high-dose protein therapies require concentrated protein solutions. These high concentrations often result in very viscous formulations that are difficult to administer by injection, cause pain at the site of injection, are often imprecise, and/or may have decreased chemical and/or physical stability.

These characteristics result in manufacturing, storage, and usage requirements that can be challenging to achieve, in particular for formulations having high concentrations of high-molecular-weight proteins, such as mAbs. All protein therapeutics to some extent are subject to physical and chemical instability, such as aggregation, denaturation, crosslinking, deamidation, isomerization, oxidation, and clipping (Wang et al., *J. Pharm. Sci.* 96:1-26, 2007). Thus, optimal formulation development is paramount in the development of commercially viable protein pharmaceuticals.

High protein concentrations pose challenges relating to the physical and chemical stability of the protein, as well as difficulty with manufacture, storage, and delivery of the protein formulation. One problem is the tendency of proteins to aggregate and form particulates during processing and/or storage, which makes manipulations during further processing and/or delivery difficult. Concentration-dependent degradation and/or aggregation are major challenges in developing protein formulations at higher concentrations. In addition to the potential for non-native protein aggregation and particulate formation, reversible self-association in aqueous solutions may occur, which contributes to, among other things, increased viscosity that complicates delivery by injection. (See, for example, Steven J. Shire et al., *J. Pharm. Sci.* 93:1390-1402, 2004.) Increased viscosity is one of the key challenges encountered in concentrated protein compositions affecting both production processes and the ability to readily deliver such compositions by conventional means. (See, for example, J. Jezek et al., *Advanced Drug Delivery Reviews* 63:1107-1117, 2011.)

Highly viscous liquid formulations are difficult to manufacture, draw into a syringe, and inject subcutaneously or intramuscularly. The use of force in manipulating the viscous formulations can lead to excessive frothing, which may further denature and inactivate the therapeutically active protein. High viscosity solutions also require larger diameter needles for injection and produce more pain at the injection site.

Currently available commercial mAb products administered by SC or IM injection are usually formulated in aqueous buffers, such as a phosphate or L-histidine buffer, with excipients or surfactants, such as mannitol, sucrose, lactose, trehalose, POLOXAMER® (nonionic triblock copolymers composed of a central hydrophobic chain of polyoxypropylene (poly(propylene oxide)) flanked by two hydrophilic chains of polyoxyethylene (poly(ethylene oxide))) or POLYSORBATE® 80 (PEG(80)sorbitan monolaurate), to prevent aggregation and improve stability. Reported antibody concentrations formulated as described above are typically up to about 100 mg/mL (Wang et al., *J. Pharm. Sci.* 96:1-26, 2007).

U.S. Pat. No. 7,758,860 describes reducing the viscosity in formulations of low-molecular-weight proteins using a buffer and a viscosity-reducing inorganic salt, such as calcium chloride or magnesium chloride. These same salts, however, showed little effect on the viscosity of a high-molecular-weight antibody (IMA-638) formulation. As described in U.S. Pat. No. 7,666,413, the viscosity of aqueous formulations of high-molecular-weight proteins has been reduced by the addition of such salts as arginine hydrochloride, sodium thiocyanate, ammonium thiocyanate, ammonium sulfate, ammonium chloride, calcium chloride, zinc chloride, or sodium acetate in a concentration of greater than about 100 mM or, as described in U.S. Pat. No. 7,740,842, by addition of organic or inorganic acids. However, these salts do not reduce the viscosity to a desired level and in some cases make the formulation so acidic that it is likely to cause pain at the site of injection.

U.S. Pat. No. 7,666,413 describes reduced-viscosity formulations containing specific salts and a reconstituted anti-IgE mAb, but with a maximum antibody concentration of only up to about 140 mg/mL. U.S. Pat. No. 7,740,842 describes E25 anti-IgE mAb formulations containing acetate/acetic acid buffer with antibody concentrations up to 257 mg/mL. The addition of salts such as NaCl, CaCl2, or MgCl2 was demonstrated to decrease the dynamic viscosity under high-shear conditions; however, at low-shear the salts produced an undesirable and dramatic increase in the dynamic viscosity. Additionally, inorganic salts such as NaCl may lower solution viscosity and/or decrease aggregation (EP 1981824).

Non-aqueous antibody or protein formulations have also been described. WO2006/071693 describes a non-aqueous suspension of up to 100 mg/mL mAb in a formulation having a viscosity enhancer (polyvinylpyrrolidone, PVP) and a solvent (benzyl benzoate or PEG 400). WO2004/089335 describes 100 mg/mL non-aqueous lysozyme suspension formulations containing PVP, glycofurol, benzyl benzoate, benzyl alcohol, or PEG 400. US2008/0226689A1 describes 100 mg/mL human growth hormone (hGH) single phase, three vehicle component (polymer, surfactant, and a solvent), non-aqueous, viscous formulations. U.S. Pat. No. 6,730,328 describes non-aqueous, hydrophobic, non-polar vehicles of low reactivity, such as perfluorodecalin, for protein formulations. These formulations are non-optimal and have high viscosities that impair processing, manufacturing and injection; lead to the presence of multiple vehicle components in the formulations; and present potential regulatory challenges associated with using polymers not yet approved by the FDA.

Alternative non-aqueous protein or antibody formulations have been described using organic solvents, such as benzyl benzoate (Miller et al., *Langmuir* 26:1067-1074, 2010), benzyl acetate, ethanol, or methyl ethyl ketone (Srinivasan et al., *Pharm. Res.* 30:1749-1757, 2013). In both instances, viscosities of less than 50 centipoise (cP) were achieved upon formulation at protein concentrations of at least about 200 mg/mL. U.S. Pat. No. 6,252,055 describes mAb formulations with concentrations ranging from 100 mg/mL up to 257 mg/mL. Formulations with concentrations greater than about 189 mg/mL demonstrated dramatically increased viscosities, low recovery rates, and difficulty in processing. U.S. Patent Application Publication No. 2012/0230982 describes antibody formulations with concentrations of 100 mg/mL to 200 mg/mL. None of these formulations are low enough viscosity for ease of injection.

Du and Klibanov (Biotechnology and Bioengineering 108:632-636, 2011) described reduced viscosity of concentrated aqueous solutions of bovine serum albumin with a maximum concentration up to 400 mg/mL and bovine gamma globulin with a maximum concentration up to 300 mg/mL. Guo et al. (*Pharmaceutical Research* 29:3102-3109, 2012) described low-viscosity aqueous solutions of four model mAbs achieved using hydrophobic salts. The mAb formulation employed by Guo had an initial viscosity, prior to adding salts, no greater than 73 cP. The viscosities of many pharmaceutically important mAbs, on the other hand, can exceed 1,000 cP at therapeutically relevant concentrations.

It is not a trivial matter to control aggregation and viscosity in high-concentration mAb solutions (EP 2538973). This is evidenced by the few mAb products currently on the market as high-concentration formulations (>100 mg/mL) (EP 2538973).

The references cited above demonstrate that while many groups have attempted to prepare low-viscosity formulations of mAbs and other therapeutically important proteins, a truly useful formulation for many proteins has not yet been achieved. Notably, many of the above reports employ agents for which safety and toxicity profiles have not been fully established. These formulations would therefore face a higher regulatory burden prior to approval than formulations containing compounds known to be safe. Indeed, even if a compound were to be shown to substantially reduce viscosity, the compound may ultimately be unsuitable for use in a formulation intended for injection into a human.

Many pharmaceutically important high-molecular-weight proteins, such as mAbs, are currently administered via IV infusions in order to deliver therapeutically effective amounts of protein due to problems with high viscosity and other properties of concentrated solutions of large proteins. For example, to provide a therapeutically effective amount of many high-molecular-weight proteins, such as mAbs, in volumes less than about 2 mL, protein concentrations greater than 150 mg/mL are often required.

It is, therefore, an object of the present invention to provide concentrated, low-viscosity liquid formulations of pharmaceutically important proteins, especially high-molecular-weight proteins, such as mAbs.

It is a further object of the present invention to provide concentrated low-viscosity liquid formulations of proteins, especially high-molecular-weight proteins, such as mAbs, capable of delivering therapeutically effective amounts of these proteins in volumes useful for SC and IM injections.

It is a further object of the present invention to provide the concentrated liquid formulations of proteins, especially high-molecular-weight proteins, such as mAbs, with low viscosities that can improve injectability and/or patient compliance, convenience, and comfort.

It is also an object of the present invention to provide methods for making and storing concentrated, low-viscosity formulations of proteins, especially high-molecular-weight proteins, such as mAbs.

It is an additional object of the present invention to provide methods of administering low-viscosity, concentrated liquid formulations of proteins, especially high-molecular-weight proteins, such as mAbs. It is an additional object of the present invention to provide methods for processing reduced-viscosity, high-concentration biologics with concentration and filtration techniques known to those skilled in the art.

SUMMARY OF THE INVENTION

Concentrated, low-viscosity, low-volume liquid pharmaceutical formulations of proteins have been developed. Such formulations can be rapidly and conveniently administered by subcutaneous (SC) or intramuscular (IM) injection, rather than by lengthy intravenous infusion. These formulations include low-molecular-weight and/or high-molecular-weight proteins, such as mAbs, and viscosity-lowering agents that are typically bulky polar organic compounds, such as many of the GRAS (US Food and Drug Administration's list of compounds generally regarded as safe), inactive injectable ingredients and FDA-approved therapeutics.

The concentration of proteins is between about 10 mg/mL and about 5,000 mg/mL, more preferably from about 100 mg/mL to about 2,000 mg/mL. In some embodiments, the concentration of proteins is between about 100 mg/mL to about 500 mg/mL, more preferably from about 300 mg/mL to about 500 mg/mL. Formulations containing proteins and viscosity-lowering agents are stable when stored at a temperature of 4° C., for a period of at least one month, preferably at least two months, and most preferably at least three months. The viscosity of the formulation is less than about 75 cP, preferably below 50 cP, and most preferably below 20 cP at about 25° C. In some embodiments, the viscosity is less than about 15 cP or even less than or about 10 cP at about 25° C. In certain embodiments, the viscosity of the formulation is about 10 cP. Formulations containing proteins and viscosity-lowering agents typically are measured at shear rates from about 0.6 $s^{-1}$ to about 450 $s^{-1}$, and preferably from about 2 $s^{-1}$ to about 400 $s^{-1}$, when measured using a cone and plate viscometer. Formulations containing proteins and viscosity-lowering agents typically are measured at shear rates from about 3 $s^{-1}$ to about 55,000 $s^{-1}$, and preferably from about 20 $s^{-1}$ to about 2,000 $s^{-1}$, when measured using a microfluidic viscometer.

The viscosity of the protein formulation is reduced by the presence of one or more viscosity-lowering agents. Unless specifically stated otherwise, the term "viscosity-lowering agent" includes both single compounds and mixtures of two or more compounds. It is preferred that the viscosity-lowering agent is present in the formulation at a concentration less than about 1.0 M, preferably less than about 0.50 M, more preferably less than about 0.30 M, and most preferably less than about 0.15 M. In some embodiments, the viscosity-lowering agent is present in the formulation in concentrations as low as 0.01 M. The formulations can have a viscosity that is at least about 30% less, preferably at least about 50% less, most preferably at least about 75% less, than the viscosity of the corresponding formulation under the same conditions except for replacement of the viscosity-lowering agent with an appropriate buffer or salt of about the same concentration. In some embodiments, a low-viscosity formulation is provided where the viscosity of the corresponding formulation without the viscosity-lowering agent is greater than about 200 cP, greater than about 500 cP, or even above about 1,000 cP. In a preferred embodiment, the shear rate of the formulation is at least about 0.5 $s^{-1}$, when measured using a cone and plate viscometer or at least about 1.0 $s^{-1}$, when measured using a microfluidic viscometer.

For embodiments in which the protein is a "high-molecular-weight protein", the high molecular weight protein may have a molecular weight between about 100 kDa and about 1,000 kDa, preferably between about 120 kDa and about 500 kDa, and most preferably between about 120 kDa and about 250 kDa. The high-molecular-weight protein can be an antibody, such as a mAb, or a PEGylated, or otherwise a derivatized form thereof. Preferred mAbs include natalizumab (TYSABRI®), cetuximab (ERBITUX®), bevacizumab (AVASTIN®), trastuzumab (HERCEPTIN®), infliximab (REMICADE®), rituximab (RITUXAN®), panitumumab (VECTIBIX®), ofatumumab (ARZERRA®), and biosimilars thereof. The high-molecular-weight protein, optionally PEGylated, can be an enzyme. Other proteins and mixtures of proteins may also be formulated to reduce their viscosity.

In some embodiments, the protein and viscosity-lowering agent are provided in a lyophilized dosage unit, sized for reconstitution with a sterile aqueous pharmaceutically acceptable vehicle, to yield the concentrated low-viscosity liquid formulations. The presence of the viscosity-lowering agent(s) facilitates and/or accelerates the reconstitution of the lyophilized dosage unit compared to a lyophilized dosage unit not containing a viscosity-lowering agent.

Methods are provided herein for preparing concentrated, low-viscosity liquid formulations of high-molecular-weight proteins such as mAbs, as well as methods for storing the low-viscosity, high-concentration protein formulations, and for administration thereof to patients. In another embodiment, the viscosity-lowering agent is added to facilitate processing (e.g., pumping, concentration, and/or filtration) by reducing the viscosity of the protein solutions.

BRIEF DESCRIPTION OF THE DRAWINGS

FIG. 4 is a bar graph comparing the fold reduction in viscosity as a function of pH for aqueous solutions containing biosimilar bevacizumab (AVASTIN®; at approximately 200 mg/mL or 226 mg/mL) and 0.25 M camphorsulfonic acid arginine (CSAA). The fold reduction is computed as the ratio of the viscosity (cP) in phosphate-citrate buffer to the viscosity (cP) in the 0.25 M CSAA solution.

FIG. 5 is a graph of the viscosity (cP) of aqueous solutions of biosimilar cetuximab (ERBITUX®; at 202±5 mg/mL, 229±5 mg/mL, or 253±4 mg/mL) containing 0.25 M CSAA as a function of pH along the x-axis at 25° C.

DETAILED DESCRIPTION OF THE INVENTION

I. Definitions

Figure 1A:
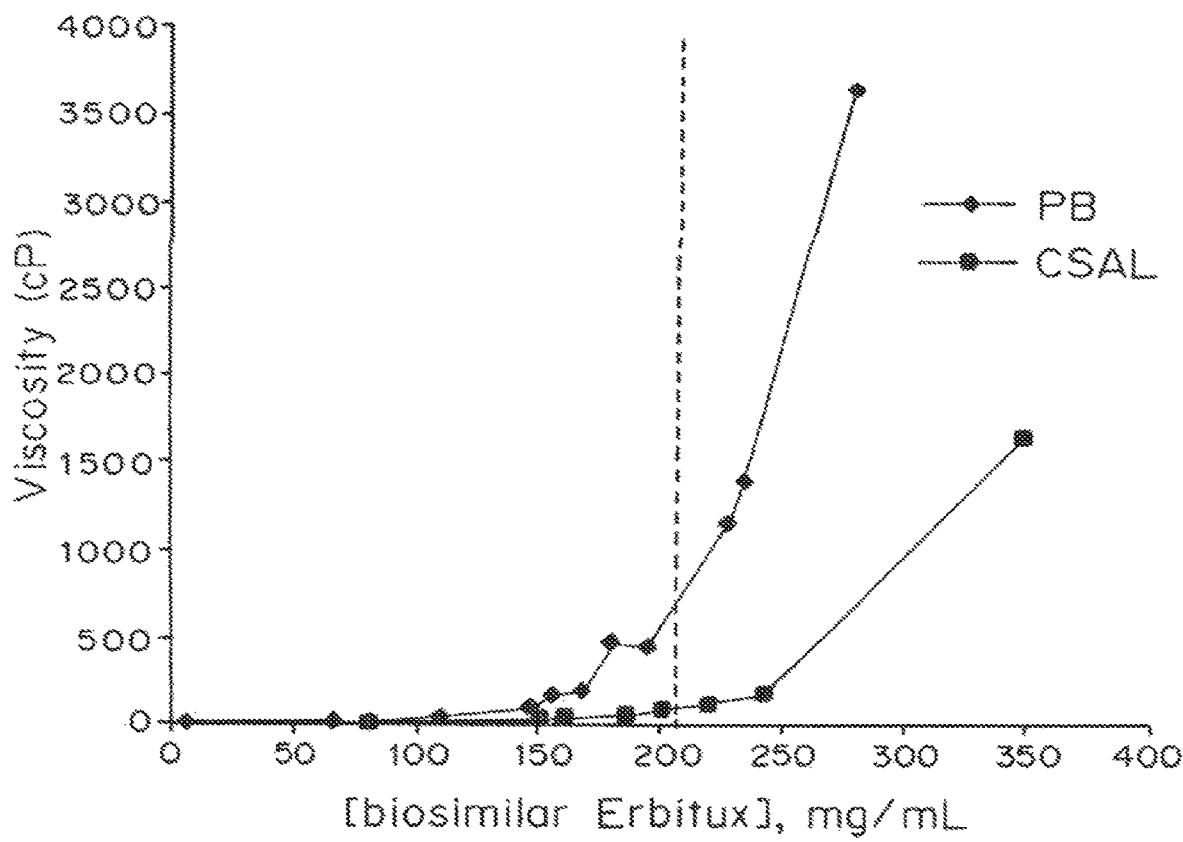
FIG. 1A and FIG. 1B depict the viscosity in cP as a function of the protein concentration (in mg/mL) for solutions of biosimilar cetuximab (ERBITUX®) in 0.25 M phosphate buffer (PB; diamonds) and a solution containing 0.25 M camphorsulfonic acid L-lysine (CSAL; squares) at 25° C. and final pH of 7.0. The data points incorporate standard deviations which, however, are often smaller than the symbols.

The term "protein," as generally used herein, refers to a polymer of amino acids linked to each other by peptide bonds to form a polypeptide for which the chain length is sufficient to produce at least a detectable tertiary structure. Proteins having a molecular weight (expressed in kDa wherein "Da" stands for "Daltons" and 1 kDa=1,000 Da) greater than about 100 kDa may be designated "high-molecular-weight proteins," whereas proteins having a molecular weight less than about 100 kDa may be designated "low-molecular-weight proteins." The term "low-molecular-weight protein" excludes small peptides lacking the requisite of at least tertiary structure necessary to be considered a protein. Protein molecular weight may be determined using standard methods known to one skilled in the art, including, but not limited to, mass spectrometry (e.g., ESI, MALDI) or calculation from known amino acid sequences and glycosylation. Proteins can be naturally occurring or non-naturally occurring, synthetic, or semi-synthetic.

"Essentially pure protein(s)" and "substantially pure protein(s)" are used interchangeably herein and refer to a composition comprising at least about 90% by weight pure protein, preferably at least about 95% pure protein by weight. "Essentially homogeneous" and "substantially homogeneous" are used interchangeably herein and refer to a composition wherein at least about 90% by weight of the protein present is a combination of the monomer and reversible di- and oligo-meric associates (not irreversible aggregates), preferably at least about 95%.

The term "antibody," as generally used herein, broadly covers mAbs (including full-length antibodies which have an immunoglobulin Fc region), antibody compositions with polyepitopic specificity, bispecific antibodies, diabodies, and single-chain antibody molecules, as well as antibody fragments (e.g., Fab, Fab', F(ab')2, and Fv), single domain antibodies, multivalent single domain antibodies, Fab fusion proteins, and fusions thereof.

The term "monoclonal antibody" or "mAb," as generally used herein, refers to an antibody obtained from a population of substantially homogeneous antibodies, i.e., the individual antibodies comprising the population are identical, except for possible naturally occurring mutations that may be present in minor amounts. Monoclonal antibodies are highly specific, being directed against a single epitope. These are typically synthesized by culturing hybridoma cells, as described by Kohler et al. (*Nature* 256: 495, 1975), or may be made by recombinant DNA methods (see, e.g., U.S. Pat. No. 4,816,567), or isolated from phage antibody libraries using the techniques described in Clackson et al. (*Nature* 352: 624-628, 1991) and Marks et al. (*J. Mol. Biol.* 222: 581-597, 1991), for example. As used herein, "mAbs" specifically include derivatized antibodies, antibody-drug conjugates, and "chimeric" antibodies in which a portion of the heavy and/or light chain is identical with or homologous to corresponding sequences in antibodies derived from a particular species or belonging to a particular antibody class or subclass, while the remainder of the chain(s) is (are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA* 81:6851-6855, 1984).

An "antibody fragment" comprises a portion of an intact antibody, including the antigen binding and/or the variable region of the intact antibody. Examples of antibody fragments include Fab, Fab', F(ab')2, and Fv fragments; diabodies; linear antibodies (see U.S. Pat. No. 5,641,870; Zapata et al., *Protein Eng.* 8:1057-1062, 1995); single-chain antibody molecules; multivalent single domain antibodies; and multispecific antibodies formed from antibody fragments.

"Humanized" forms of non-human (e.g., murine) antibodies are chimeric immunoglobulins, immunoglobulin chains, or fragments thereof (such as Fv, Fab, Fab', F(ab')2, or other antigen-binding subsequences of antibodies) of mostly human sequences, which contain minimal sequences derived from non-human immunoglobulin. (See, e.g., Jones et al., *Nature* 321:522-525, 1986; Reichmann et al., *Nature* 332:323-329, 1988; and Presta, *Curr. Op. Struct. Biol.* 2:593-596, 1992.)

"Rheology" refers to the study of the deformation and flow of matter.

"Viscosity" refers to the resistance of a substance (typically a liquid) to flow. Viscosity is related to the concept of shear force; it can be understood as the effect of different layers of the fluid exerting shearing force on each other, or on other surfaces, as they move against each other. There are several measures of viscosity. The units of viscosity are $Ns/m^2$, known as Pascal-seconds (Pa-s). Viscosity can be "kinematic" or "absolute". Kinematic viscosity is a measure of the rate at which momentum is transferred through a fluid. It is measured in Stokes (St). The kinematic viscosity is a measure of the resistive flow of a fluid under the influence of gravity. When two fluids of equal volume and differing viscosity are placed in identical capillary viscometers and allowed to flow by gravity, the more viscous fluid takes longer than the less viscous fluid to flow through the capillary. If, for example, one fluid takes 200 seconds (s) to complete its flow and another fluid takes 400 s, the second fluid is called twice as viscous as the first on a kinematic viscosity scale. The dimension of kinematic viscosity is $length^2/time$. Commonly, kinematic viscosity is expressed in centiStokes (cSt). The SI unit of kinematic viscosity is $mm^2/s$, which is equal to 1 cSt. The "absolute viscosity," sometimes called "dynamic viscosity" or "simple viscosity," is the product of kinematic viscosity and fluid density. Absolute viscosity is expressed in units of centipoise (cP). The SI unit of absolute viscosity is the milliPascal-second (mPa-s), where 1 cP=1 mPa-s. Viscosity may be measured by using, for example, a viscometer at a given shear rate or multiple shear rates. An "extrapolated zero-shear" viscosity can be determined by creating a best fit line of the four highest-shear points on a plot of absolute viscosity versus shear rate, and linearly extrapolating viscosity back to zero-shear. Alternatively, for a Newtonian fluid, viscosity can be determined by averaging viscosity values at multiple shear rates. Viscosity can also be measured using a microfluidic viscometer at single or multiple shear rates (also called flow rates), wherein absolute viscosity is derived from a change in pressure as a liquid flows through a channel. Viscosity equals shear stress over shear rate. Viscosities measured with microfluidic viscometers can, in some embodiments, be directly compared to extrapolated zero-shear viscosities, for example those extrapolated from viscosities measured at multiple shear rates using a cone and plate viscometer.

"Shear rate" refers to the rate of change of velocity at which one layer of fluid passes over an adjacent layer. The velocity gradient is the rate of change of velocity with distance from the plates. This simple case shows the uniform velocity gradient with shear rate $(v_1-v_2)/h$ in units of (cm/sec)/(cm)=1/sec. Hence, shear rate units are reciprocal seconds or, in general, reciprocal time. For a microfluidic viscometer, change in pressure and flow rate are related to shear rate. "Shear rate" is to the speed with which a material is deformed. Formulations containing proteins and viscosity-lowering agents are typically measured at shear rates ranging from about $0.5\ s^{-1}$ to about $200\ s^{-1}$ when measured using a cone and plate viscometer and a spindle appropriately chosen by one skilled in the art to accurately measure viscosities in the viscosity range of the sample of interest (i.e., a sample of 20 cP is most accurately measured on a CPE40 spindle affixed to a DV2T viscometer (Brookfield)); greater than about 20 $s^{-1}$ to about 3,000 $s^{-1}$ when measured using a microfluidic viscometer.

For classical "Newtonian" fluids, as generally used herein, viscosity is essentially independent of shear rate. For "non-Newtonian fluids," however, viscosity either decreases or increases with increasing shear rate, e.g., the fluids are "shear thinning" or "shear thickening", respectively. In the case of concentrated (i.e., high-concentration) protein solutions, this may manifest as pseudoplastic shear-thinning behavior, i.e., a decrease in viscosity with shear rate.

The term "chemical stability," as generally used herein, refers to the ability of the protein components in a formulation to resist degradation via chemical pathways, such as oxidation, deamidation, or hydrolysis. A protein formulation is typically considered chemically stable if less than about 5% of the components are degraded after 24 months at 4° C.

The term "physical stability," as generally used herein, refers to the ability of a protein formulation to resist physical deterioration, such as aggregation. A formulation that is physically stable forms only an acceptable percentage of irreversible aggregates (e.g., dimers, trimers, or other aggregates) of the bioactive protein agent. The presence of aggregates may be assessed in a number of ways, including by measuring the average particle size of the proteins in the formulation by means of dynamic light scattering. A formulation is considered physically stable if less than about 5% irreversible aggregates are formed after 24 months at 4° C. Acceptable levels of aggregated contaminants ideally would be less than about 2%. Levels as low as about 0.2% are achievable, although approximately 1% is more typical.

The term "stable formulation," as generally used herein, means that a formulation is both chemically stable and physically stable. A stable formulation may be one in which more than about 95% of the bioactive protein molecules retain bioactivity in a formulation after 24 months of storage at 4° C., or equivalent solution conditions at an elevated temperature, such as one month storage at 40° C. Various analytical techniques for measuring protein stability are available in the art and are reviewed, for example, in Peptide and Protein Drug Delivery, 247-301, Vincent Lee, Ed., Marcel Dekker, Inc., New York, N.Y. (1991) and Jones, A., *Adv. Drug Delivery Revs.* 10:29-90, 1993. Stability can be measured at a selected temperature for a certain time period. For rapid screening, for example, the formulation may be kept at 40° C., for 2 weeks to one month, at which time residual biological activity is measured and compared to the initial condition to assess stability. When the formulation is to be stored at 2° C.-8° C., generally the formulation should be stable at 30° C. or 40° C. for at least one month and/or stable at 2° C.-8° C. for at least 2 years. When the formulation is to be stored at room temperature, about 25° C., generally the formulation should be stable for at least 2 years at about 25° C. and/or stable at 40° C. for at least about 6 months. The extent of aggregation following lyophilization and storage can be used as an indicator of protein stability. In some embodiments, the stability is assessed by measuring the particle size of the proteins in the formulation. In some embodiments, stability may be assessed by measuring the activity of a formulation using standard biological activity or binding assays well within the abilities of one ordinarily skilled in the art.

The term protein "particle size," as generally used herein, means the average diameter of the predominant population of bioactive molecule particulates, or particle size distributions thereof, in a formulation as determined by using well known particle sizing instruments, for example, dynamic light scattering, SEC (size exclusion chromatography), or other methods known to one ordinarily skilled in the art.

The term "concentrated" or "high-concentration", as generally used herein, describes liquid formulations having a final concentration of protein greater than about 10 mg/mL, preferably greater than about 50 mg/mL, more preferably greater than about 100 mg/mL, still more preferably greater than about 200 mg/mL, or most preferably greater than about 250 mg/mL.

A "reconstituted formulation," as generally used herein, refers to a formulation which has been prepared by dissolving a dry powder, lyophilized, spray-dried or solvent-precipitated protein in a diluent, such that the protein is dissolved or dispersed in aqueous solution for administration.

A "lyoprotectant" is a substance which, when combined with a protein, significantly reduces chemical and/or physical instability of the protein upon lyophilization and/or subsequent storage. Exemplary lyoprotectants include sugars and their corresponding sugar alcohols, such as sucrose, lactose, trehalose, dextran, erythritol, arabitol, xylitol, sorbitol, and mannitol; amino acids, such as arginine or histidine; lyotropic salts, such as magnesium sulfate; polyols, such as propylene glycol, glycerol, poly(ethylene glycol), or poly(propylene glycol); and combinations thereof. Additional exemplary lyoprotectants include gelatin, dextrins, modified starch, and carboxymethyl cellulose. Preferred sugar alcohols are those compounds obtained by reduction of mono- and di-saccharides, such as lactose, trehalose, maltose, lactulose, and maltulose. Additional examples of sugar alcohols are glucitol, maltitol, lactitol and isomaltulose. The lyoprotectant is generally added to the pre-lyophilized formulation in a "lyoprotecting amount." This means that, following lyophilization of the protein in the presence of the lyoprotecting amount of the lyoprotectant, the protein essentially retains its physical and chemical stability and integrity.

A "diluent" or "carrier," as generally used herein, is a pharmaceutically acceptable (i.e., safe and non-toxic for administration to a human or another mammal) and useful ingredient for the preparation of a liquid formulation, such as an aqueous formulation reconstituted after lyophilization. Exemplary diluents include sterile water, bacteriostatic water for injection (BWFI), a pH buffered solution (e.g., phosphate-buffered saline), sterile saline solution, Ringer's solution or dextrose solution, and combinations thereof.

A "preservative" is a compound which can be added to the formulations herein to reduce contamination by and/or action of bacteria, fungi, or another infectious agent. The addition of a preservative may, for example, facilitate the production of a multi-use (multiple-dose) formulation. Examples of potential preservatives include octadecyldimethylbenzylammonium chloride, hexamethonium chloride, benzalkonium chloride (a mixture of alkylbenzyldimethylammonium chlorides in which the alkyl groups are long-chained), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol.

A "bulking agent," as generally used herein, is a compound which adds mass to a lyophilized mixture and contributes to the physical structure of the lyophilized cake (e.g.

facilitates the production of an essentially uniform lyophilized cake which maintains an open pore structure). Exemplary bulking agents include mannitol, glycine, lactose, modified starch, poly(ethylene glycol), and sorbitol.

A "therapeutically effective amount" is the least concentration required to effect a measurable improvement or prevention of any symptom or a particular condition or disorder, to effect a measurable enhancement of life expectancy, or to generally improve patient quality of life. The therapeutically effective amount is dependent upon the specific biologically active molecule and the specific condition or disorder to be treated. Therapeutically effective amounts of many proteins, such as the mAbs described herein, are well known in the art. The therapeutically effective amounts of proteins not yet established or for treating specific disorders with known proteins, such as mAbs, to be clinically applied to treat additional disorders may be determined by standard techniques which are well within the craft of a skilled artisan, such as a physician.

The term "injectability" or "syringeability," as generally used herein, refers to the injection performance of a pharmaceutical formulation through a syringe equipped with an 18-32 gauge needle, optionally thin walled. Injectability depends upon factors such as pressure or force required for injection, evenness of flow, aspiration qualities, and freedom from clogging. Injectability of the liquid pharmaceutical formulations may be assessed by comparing the injection force of a reduced-viscosity formulation to a standard formulation without added viscosity-lowering agents. The reduction in the injection force of the formulation containing a viscosity-lowering agent reflects improved injectability of that formulation. The reduced viscosity formulations have improved injectability when the injection force is reduced by at least 10%, preferably by at least 30%, more preferably by at least 50%, and most preferably by at least 75% when compared to a standard formulation having the same concentration of protein under otherwise the same conditions, except for replacement of the viscosity-lowering agent with an appropriate buffer of about the same concentration. Alternatively, injectability of the liquid pharmaceutical formulations may be assessed by comparing the time required to inject the same volume, such as 0.5 mL, or more preferably about 1 mL, of different liquid protein formulations when the syringe is depressed with the same force.

The term "injection force," as generally used herein, refers to the force required to push a given liquid formulation through a given syringe equipped with a given needle gauge at a given injection speed. The injection force is typically reported in Newtons. For example, the injection force may be measured as the force required to push a liquid formulation through a 1 mL plastic syringe having a 0.25 inch inside diameter, equipped with a 0.50 inch 27 gauge needle at a 250 mm/min injection speed. Testing equipment can be used to measure the injection force. When measured under the same conditions, a formulation with lower viscosity will generally require an overall lower injection force.

The "viscosity gradient," as used herein, refers to the rate of change of the viscosity of a protein solution as protein concentration increases. The viscosity gradient can be approximated from a plot of the viscosity as a function of the protein concentration for a series of formulations that are otherwise the same but have different protein concentrations. The viscosity increases approximately exponentially with increasing protein concentration. The viscosity gradient at a specific protein concentration can be approximated from the slope of a line tangent to the plot of viscosity as a function of protein concentration. The viscosity gradient can be approximated from a linear approximation to the plot of viscosity as a function of any protein concentration or over a narrow window of protein concentrations. In some embodiments a formulation is said to have a decreased viscosity gradient if, when the viscosity as a function of protein concentration is approximated as an exponential function, the exponent of the exponential function is smaller than the exponent obtained for the otherwise same formulation without the viscosity-lowering agent. In a similar manner, a formulation can be said to have a lower/higher viscosity gradient when compared to a second formulation if the exponent for the formulation is lower/higher than the exponent for the second formulation. The viscosity gradient can be numerically approximated from a plot of the viscosity as a function of protein concentration by other methods known to the skilled formulation researchers.

The term "reduced-viscosity formulation," as generally used herein, refers to a liquid formulation having a high concentration of a high-molecular-weight protein, such as a mAb, or a low-molecular-weight protein that is modified by the presence of one or more additives to lower the viscosity, as compared to a corresponding formulation that does not contain the viscosity-lowering additive(s).

The term "osmolarity," as generally used herein, refers to the total number of dissolved components per liter. Osmolarity is similar to molarity but includes the total number of moles of dissolved species in solution. An osmolarity of 1 Osm/L means there is 1 mole of dissolved components per L of solution. Some solutes, such as ionic solutes that dissociate in solution, will contribute more than 1 mole of dissolved components per mole of solute in the solution. For example, NaCl dissociates into $Na^+$ and $Cl^-$ in solution and thus provides 2 moles of dissolved components per 1 mole of dissolved NaCl in solution. Physiological osmolarity is typically in the range of about 280 mOsm/L to about 310 mOsm/L.

The term "tonicity," as generally used herein, refers to the osmotic pressure gradient resulting from the separation of two solutions by a semi-permeable membrane. In particular, tonicity is used to describe the osmotic pressure created across a cell membrane when a cell is exposed to an external solution. Solutes that can cross the cellular membrane do not contribute to the final osmotic pressure gradient. Only those dissolved species that do not cross the cell membrane will contribute to osmotic pressure differences and thus tonicity.

The term "hypertonic," as generally used herein, refers to a solution with a higher concentration of solutes than is present on the inside of the cell. When a cell is immersed into a hypertonic solution, the tendency is for water to flow out of the cell in order to balance the concentration of the solutes.

The term "hypotonic," as generally used herein, refers to a solution with a lower concentration of solutes than is present on the inside of the cell. When a cell is immersed into a hypotonic solution, water flows into the cell in order to balance the concentration of the solutes.

The term "isotonic," as generally used herein, refers to a solution wherein the osmotic pressure gradient across the cell membrane is essentially balanced. An isotonic formulation is one which has essentially the same osmotic pressure as human blood. Isotonic formulations will generally have an osmotic pressure from about 250 mOsm/kg to 350 mOsm/kg.

The term "liquid formulation," as used herein, is a protein that is either supplied in an acceptable pharmaceutical diluent or one that is reconstituted in an acceptable pharmaceutical diluent prior to administration to the patient.

The terms "branded" and "reference," when used to refer to a protein or biologic, are used interchangeably herein to mean the single biological product licensed under section 351(a) of the U.S. Public Health Service Act (42 U.S.C. § 262).

The term "biosimilar," as used herein, is generally used interchangeably with "a generic equivalent" or "follow-on." For example, a "biosimilar mAb" refers to a subsequent version of an innovator's mAb typically made by a different company. "Biosimilar" when used in reference to a branded protein or branded biologic can refer to a biological product evaluated against the branded protein or branded biologic and licensed under section 351(k) of the U.S. Public Health Service Act (42 U.S.C. § 262). A biosimilar mAb can be one that satisfies one or more guidelines adopted May 30, 2012 by the Committee for Medicinal Products for Human Use (CHMP) of the European Medicines Agency and published by the European Union as "Guideline on similar biological medicinal products containing monoclonal antibodies—non-clinical and clinical issues" (Document Reference EMA/CHMP/BMWP/403543/2010).

Biosimilars can be produced by microbial cells (prokaryotic, eukaryotic), cell lines of human or animal origin (e.g., mammalian, avian, insect), or tissues derived from animals or plants. The expression construct for a proposed biosimilar product will generally encode the same primary amino acid sequence as its reference product. Minor modifications, such as N- or C-terminal truncations that will not have an effect on safety, purity, or potency, may be present.

A biosimilar mAb is similar to the reference mAb physiochemically or biologically both in terms of safety and efficacy. The biosimilar mAb can be evaluated against a reference mAb using one or more in vitro studies including assays detailing binding to target antigen(s); binding to isoforms of the Fc gamma receptors (FcγRI, FcγRII, and FcγRIII), FcRn, and complement (C1q); Fab-associated functions (e.g. neutralization of a soluble ligand, receptor activation or blockade); or Fc-associated functions (e.g. antibody-dependent cell-mediated cytotoxicity, complement-dependent cytotoxicity, complement activation). In vitro comparisons may be combined with in vivo data demonstrating similarity of pharmacokinetics, pharmacodynamics, and/or safety. Clinical evaluations of a biosimilar mAb against a reference mAb can include comparisons of pharmacokinetic properties (e.g. $AUC_{0-inf}$, $AUC_{0-t}$, $C_{max}$, $t_{max}$, $C_{trough}$); pharmacodynamic endpoints; or similarity of clinical efficacy (e.g. using randomized, parallel group comparative clinical trials). The quality comparison between a biosimilar mAb and a reference mAb can be evaluated using established procedures, including those described in the "Guideline on similar biological medicinal products containing biotechnology-derived proteins as active substance: Quality issues" (EMEA/CHMP/BWP/49348/2005), and the "Guideline on development, production, characterization and specifications for monoclonal antibodies and related substances" (EMEA/CHMP/BWP/157653/2007).

Differences between a biosimilar mAb and a reference mAb can include post-translational modification, e.g. by attaching to the mAb other biochemical groups such as a phosphate, various lipids and carbohydrates; by proteolytic cleavage following translation; by changing the chemical nature of an amino acid (e.g., formylation); or by many other mechanisms. Other post-translational modifications can be a consequence of manufacturing process operations—for example, glycation may occur with exposure of the product to reducing sugars. In other cases, storage conditions may be permissive for certain degradation pathways such as oxidation, deamidation, or aggregation. As all of these product-related variants may be included in a biosimilar mAb.

The term "viscosity-lowering agent," as used herein, refers to a compound which acts to reduce the viscosity of a solution relative to the viscosity of the solution absent the viscosity-lowering agent. The viscosity-lowering agent may be a single compound, or may be a mixture of one or more compounds. When the viscosity-lowering agent is a mixture of two or more compounds, the listed concentration refers to each individual agent, unless otherwise specified. By way of example, a formulation containing about 0.25 M camphorsulfonic acid arginine as the viscosity-lowering agent is a solution having camphorsulfonic acid at a concentration of 0.25 M, and arginine at a concentration of 0.25 M.

Certain viscosity-lowering agents contain acidic or basic functional groups. Whether or not these functional groups are fully or partially ionized depends on the pH of the formulation they are in. Unless otherwise specified, reference to a formulation containing a viscosity-lowering agent having an ionizable functional group includes both the parent compound and any possible ionized states.

As used herein, the term "hydrogen bond donor" refers to a hydrogen atom connected to a relatively electronegative atom, which creates a partial positive charge on the hydrogen atom.

As used herein, the term "hydrogen bond acceptor" refers to a relatively electronegative atom or functional group capable of interacting with a hydrogen atom bearing a partial positive charge.

As used herein, the term "freely rotating bond" refers to any singly bonded pair of non-hydrogen atoms.

As used herein, the term "molecular polar surface area" refers to the total exposed polar area on the surface of the molecule of interest.

As used herein, the term "molar volume" refers to the total volume that one mole of the molecule of interest occupies in its native state (i.e. solid, liquid).

As used herein, the term "polarizability" refers to the induced dipole moment when the molecule of interest is placed in an electric field of unit strength.

As used herein, the term "pharmaceutically acceptable salts" refers to salts prepared from pharmaceutically acceptable non-toxic acids and bases, including inorganic acids and bases, and organic acids and bases. Suitable non-toxic acids include inorganic and organic acids such as acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic and the like. Suitable positively charged counterions include sodium, potassium, lithium, calcium and magnesium.

As used herein, the term "ionic liquid" refers to a crystalline or amorphous salt, zwitterion, or mixture thereof that is a liquid at or near temperatures where most conventional salts are solids: at less than 200° C., preferably less than 100° C. or more preferably less than 80° C. Some ionic liquids have melting temperatures around room temperature, e.g. between 10° C. and 40° C., or between 15° C. and 35° C. The term "zwitterion" is used herein to describe an overall neutrally charged molecule which carries formal positive and negative charges on different chemical groups in the molecule. Examples of ionic liquids are described in Riduan et al., *Chem. Soc. Rev.*, 42:9055-9070, 2013; Rantwijk et al., *Chem. Rev.*, 107:2757-2785, 2007; Earle et al., *Pure Appl. Chem.*, 72(7):1391-1398, 2000; and Sheldon et al., *Green Chem.*, 4:147-151, 2002.

As used herein, the term "organophosphate" refers to a compound containing one or more phosphoryl groups at least one of which is covalently connected to an organic group through a phosphoester bond.

As used herein, a "water soluble organic dye" is an organic molecule having a molar solubility of at least 0.001 M at 25° C. and pH 7, and that absorbs certain wavelengths of light, preferably in the visible-to-infrared portion of the electromagnetic spectrum, while possibly transmitting or reflecting other wavelengths of light.

As used herein, the term "chalcogen" refers to Group 16 elements, including oxygen, sulfur and selenium, in any oxidation state. For instance, unless specified otherwise, the term "chalcogen" also includes $SO_2$.

As used herein, term "alkyl group" refers to straight-chain, branched-chain and cyclic hydrocarbon groups. Unless specified otherwise, the term alkyl group embraces hydrocarbon groups containing one or more double or triple bonds. An alkyl group containing at least one ring system is a "cycloalkyl" group. An alkyl group containing at least one double bond is an "alkenyl group," and an alkyl group containing at least one triple bond is an "alkynyl group."

The term as used herein, "Aryl" refers to aromatic carbon ring systems, including fused ring systems. In an "aryl" group, each of the atoms that form the ring are carbon atoms.

The term as used herein "Heteroaryl" refers to aromatic ring systems, including fused ring systems, wherein at least one of the atoms that forms the ring is a heteroatom.

The term as used herein "Heterocycle" refers to ring systems that, including fused ring systems, are not aromatic, wherein at least one of the atoms that forms the ring is a heteroatom.

The term as used herein, "heteroatom" is any non-carbon or non-hydrogen atom. Preferred heteroatoms include oxygen, sulfur, and nitrogen. Exemplary heteroaryl and heterocyclyl rings include: benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl.

II. Formulations

Biocompatible, low-viscosity protein solutions, such as those of mAbs, can be used to deliver therapeutically effective amounts of proteins in volumes useful for subcutaneous (SC) and intramuscular (IM) injections, typically less than or about 2 mL for SC and less than or about 5 mL for IM, more preferably less than or about 1 mL for SC and less than or about 3 mL for IM. The proteins can generally have any molecular weight, although in some embodiments high-molecular-weight proteins are preferred. In other embodiments the proteins are low-molecular-weight proteins.

Formulations may have protein concentrations between about 10 mg/mL and about 5,000 mg/mL. The formulations, including mAb formulations, may have a protein concentration greater than 100 mg/mL, preferably greater than 150 mg/mL, more preferably greater than about 175 mg/ml, even more preferably greater than about 200 mg/mL, even more preferably greater than about 225 mg/mL, even more preferably greater than about 250 mg/mL, and most preferably greater than or about 300 mg/mL. In the absence of a viscosity-lowering agent, the viscosity of a protein formulation increases exponentially as the concentration is increased. Such protein formulations, in the absence of a viscosity-lowering agent, may have viscosities greater than 100 cP, greater than 150 cP, greater than 200 cP, greater than 300 cP, greater than 500 cP, or even greater than 1,000 cP, when measured at 25° C. Such formulations are often unsuitable for SC or IM injection. The use of one or more viscosity-lowering agents permits the preparation of formulations having a viscosity less than or about 100 cP, preferably less than or about 75 cP, more preferably less than or about 50 cP, even more preferably less than or about 30 cP, even more preferably less than or about 20 cP, or most preferably less than or about 10 cP, when measured at 25° C.

Although the viscosity-lowering agents may be used to lower the viscosity of concentrated protein formulations, they may be used in less-concentrated formulations as well. In some embodiments, formulations may have protein concentrations between about 10 mg/mL and about 100 mg/mL. The formulations may have a protein concentration greater than about 20 mg/mL, greater than about 40 mg/mL, or greater than about 80 mg/mL.

For certain proteins, formulations not having a viscosity-lowering agent may have viscosities greater than about 20 cP, greater than about 50 cP, or greater than about 80 cP. The use of one or more viscosity-lowering agents permits the preparation of formulations having a viscosity less than or about 80 cP, preferably less than or about 50 cP, even more preferably less than about 20 cP, or most preferably less than or about 10 cP, when measured at 25° C.

In some embodiments, the aqueous protein formulations have a viscosity that is at least about 30% less than the analogous formulation without the viscosity-lowering agent(s), when measured under the same conditions. In other embodiments, the formulations have a viscosity that is 40% less, 50% less, 60% less, 70% less, 80% less, 90% less, or even more than 90% less than the analogous formulation without the viscosity-lowering agent(s). In a preferred embodiment, the formulation contains a therapeutically effective amount of the one or more high-molecular-weight proteins, such as mAbs, in a volume of less than about 2 mL, preferably less than about 1 mL, or more preferably less than about 0.75 mL.

The reduced-viscosity formulations have improved injectability and require less injection force compared to the analogous formulation without the viscosity-lowering agent (e.g., in phosphate buffer) under otherwise the same conditions. In some embodiments, the force of injection is decreased by more than about 20%, more than about 30%, more than about 40%, more than about 50%, or more than about 2 fold, as compared to standard formulations without the viscosity-lowering agent(s) under otherwise the same injection conditions. In some embodiments, the formulations possess "Newtonian flow characteristics," defined as having viscosity which is substantially independent of shear rate. The protein formulations can be readily injected through needles of about 18-32 gauge. Preferred needle gauges for the delivery of the low-viscosity formulations include 27, 29, and 31 gauge, optionally thin walled.

The formulations may contain one or more additional excipients, such as buffers, surfactants, sugars and sugar alcohols, other polyols, preservatives, antioxidants, and chelating agents. The formulations have a pH and osmolarity suitable for administration without causing significant adverse side effects. In some embodiments, the concentrated, low-viscosity formulations have a pH between 5 and 8, between 5.5 and 7.6, between 6.0 and 7.6, between 6.8 and 7.6, or between 5.5 and 6.5.

The low-viscosity protein formulations can allow for greater flexibility in formulation development. The low-viscosity formulations can exhibit changes in viscosity that are less dependent upon the protein concentration as compared to the otherwise same formulation without the viscosity-lowering agent. The low-viscosity protein formulations can allow for increased concentrations and decreased dosage frequencies of the protein. In some embodiments the low-viscosity protein formulations contain 2 or more, 3 or more, or 4 or more different proteins. For example, combinations of 2 or more mAbs can be provided in a single low-viscosity protein formulation.

Because protein (such as mAb) formulations may be administered to patients at higher protein concentrations than otherwise similar protein formulations not containing a viscosity-lowering agent, the dosing frequency of the protein can be reduced. For instance, proteins previously requiring once daily administration may be administered once every two days, every three days, or even less frequently when the proteins are formulated with viscosity-lowering agents. Proteins which currently require multiple administrations on the same day (either at the same time or at different times of the day) may be administered in fewer injections per day. In some instances, the frequency may be reduced to a single injection once a day. By increasing the dosage administered per injection multiple-fold the dosing frequency can be decreased, for example from once every 2 weeks to once every 6 weeks.

In some embodiments, the liquid formulations have a physiological osmolarity, for example, between about 280 mOsm/L to about 310 mOsm/L. In some embodiments, the liquid formulations have an osmolarity greater than about 250 mOsm/L, greater than about 300 mOsm/L, greater than about 350 mOsm/L, greater than about 400 mOsm/L, or greater than about 500 mOsm/L. In some embodiments, the formulations have an osmolarity of about 200 mOsm/L to about 2,000 mOsm/L or about 300 mOsm/L to about 1,000 mOsm/L. In some embodiments, the liquid formulations are essentially isotonic to human blood. The liquid formulations can in some cases be hypertonic.

The additives, including the viscosity-lowering agents, can be included in any amount to achieve the desired viscosity levels of the liquid formulation, as long as the amounts are not toxic or otherwise harmful, and do not substantially interfere with the chemical and/or physical stability of the formulation. The viscosity-lowering agent(s) in some embodiments can be independently present in a concentration less than about 1.0 M, preferably less than about 0.50 M, less than or equal to about 0.30 M or less than or equal to 0.15 M. Especially preferred concentrations include about 0.15 M and about 0.30 M. For some embodiments having two or more viscosity-lowering agents, the agents are preferably, but not necessarily, present at the same concentration.

The viscosity-lowering agents permit faster reconstitution of a lyophilized dosage unit. The dosage unit is a lyophilized cake of protein, viscosity-lowering agent and other excipients, to which water, saline or another pharmaceutically acceptable fluid is added. In the absence of viscosity-lowering agents, periods of 10 minutes or more are often required in order to completely dissolve the lyophilized cake at high protein concentration. When the lyophilized cake contains one or more viscosity-lowering agents, the period required to completely dissolve the cake is often reduced by a factor of two, five or even ten. In certain embodiments, less than one minute is required to completely dissolve a lyophilized cake containing greater than or about 150, 200 or even 300 mg/mL of protein.

The low-viscosity protein formulations allow for greater flexibility in formulation development. The low-viscosity formulations exhibit a viscosity that changes less with increasing protein concentrations as compared to the otherwise same formulation without the viscosity-lowering agent(s). The low-viscosity protein formulations exhibit a decreased viscosity gradient as compared to the otherwise same formulation without the viscosity-lowering agent.

The viscosity gradient of the protein formulation may be 2-fold less, 3-fold less, or even more than 3-fold less than the viscosity gradient of the otherwise same protein formulation without the viscosity-lowering agent(s). The viscosity gradient of the protein formulation may be less than 2.0 cP mL/mg, less than 1.5 cP mL/mg, less than 1.0 cP mL/mg, less than 0.8 cP mL/mg, less than 0.6 cP mL/mg, or less than 0.2 cP mL/mg for a protein formulation having a protein concentration between 10 mg/mL and 2,000 mg/mL. By reducing the viscosity gradient of the formulation, the protein concentration can be increased to a greater degree before an exponential increase in viscosity is observed.

A. Proteins

Any protein can be formulated, including recombinant, isolated, or synthetic proteins, glycoproteins, or lipoproteins. These may be antibodies (including antibody fragments and recombinant antibodies), enzymes, growth factors or hormones, immunomodifiers, antiinfectives, antiproliferatives, vaccines, or other therapeutic, prophylactic, or diagnostic proteins. In certain embodiments, the protein has a molecular weight greater than about 150 kDa, greater than 160 kDa, greater than 170 kDa, greater than 180 kDa, greater than 190 kDa or even greater than 200 kDa.

In certain embodiments, the protein can be a PEGylated protein. The term "PEGylated protein," as used herein, refers to a protein having one or more poly(ethylene glycol) or other stealth polymer groups covalently attached thereto, optionally through a chemical linker that may be different from the one or more polymer groups. PEGylated proteins are characterized by their typically reduced renal filtration, decreased uptake by the reticuloendothelial system, and diminished enzymatic degradation leading to, for example, prolonged half-lives and enhanced bioavailability. Stealth polymers include poly(ethylene glycol); poly(propylene glycol); poly(amino acid) polymers such as poly(glutamic acid), poly(hydroxyethyl-L-asparagine), and poly(hydroxyethyl-L-glutamine); poly(glycerol); poly(-oxazoline) polymers such as poly(-methyl-2-oxazoline) and poly(-ethyl-2-oxazoline); poly(acrylamide); poly(vinylpyrrolidone); poly (N-(2-hydroxypropyl)methacrylamide); and copolymers and mixtures thereof. In preferred embodiments the stealth polymer in a PEGylated protein is poly(ethylene glycol) or a copolymer thereof. PEGylated proteins can be randomly PEGylated, i.e. having one or more stealth polymers covalently attached at non-specific site(s) on the protein, or can be PEGylated in a site-specific manner by covalently attaching the stealth polymer to specific site(s) on the protein. Site-specific PEGylation can be accomplished, for example, using activated stealth polymers having one or more reactive functional groups. Examples are described, for instance, in Hoffman et al., *Progress in Polymer Science,* 32:922-932, 2007.

In the preferred embodiment, the protein is high-molecular-weight and an antibody, most preferably a mAb, and has a high viscosity in aqueous buffered solution when concentrated sufficiently to inject a therapeutically effective amount in a volume not exceeding 1.0 to 2.0 mL for SC and 3.0 to 5.0 mL for IM administration. High-molecular-weight proteins can include those described in Scolnik, *mAbs* 1:179-184, 2009; Beck, *mAbs* 3:107-110, 2011; Baumann, *Curr. Drug Meth.* 7:15-21, 2006; or Federici, *Biologicals* 41:131-147, 2013. The proteins for use in the formulations described herein are preferably essentially pure and essentially homogeneous (i.e., substantially free from contaminating proteins and/or irreversible aggregates thereof).

Preferred mAbs herein include natalizumab (TYSABRI®), cetuximab (ERBITUX®), bevacizumab (AVASTIN®), trastuzumab (HERCEPTIN®), infliximab (REMICADE®), rituximab (RITUXAN®), panitumumab (VECTIBIX®), ofatumumab (ARZERRA®), and biosimilars thereof. Exemplary high-molecular-weight proteins can include tocilizumab (ACTEMRA®), alemtuzumab (marketed under several trade names), brodalumab (developed by Amgen, Inc ("Amgen")), denosumab (PROLIX® and XGEVA®), and biosimilars thereof.

Exemplary molecular targets for antibodies described herein include CD proteins, such as CD3, CD4, CD8, CD19, CD20 and CD34; members of the HER receptor family such as the EGF receptor, HER2, HER3 or HER4 receptor; cell adhesion molecules, such as LFA-1, Mol, p150,95, VLA-4, ICAM-1, VCAM, and αv/β3 integrin, including either α or β subunits thereof (e.g., anti-CD11a, anti-CD18, or anti-CD11b antibodies); growth factors, such as VEGF; IgE; blood group antigens; flk2/flt3 receptor; obesity (OB) receptor; protein C; PCSK9; etc.

Antibody Therapeutics Currently on the Market

Many protein therapeutics currently on the market, especially antibodies as defined herein, are administered via IV infusions due to high dosing requirements. Formulations can include one of the antibody therapeutics currently on the market or a biosimilar thereof. Some protein therapeutics currently on the market are not high-molecular-weight, but are still administered via IV infusion because high doses are needed for therapeutic efficacy. In some embodiments, liquid formulations are provided of these low-molecular-weight proteins as defined herein with concentrations to deliver therapeutically effective amounts for SC or IM injections.

Antibody therapeutics currently on the market include belimumab (BENLYSTA®), golimumab (SIMPONI ARIA®), abciximab (REOPRO®), the combination of tositumomab and iodine-131 tositumomab, marketed as BEXXAR®, alemtuzumab (CAMPATH®), palivizumab (SYNAGIS®), basiliximab (SIMULECT®), ado-trastuzumab emtansine (KADCYLA®), pertuzumab (PERJETA®), capromab pendetide (PROSTASCINT KIT®), caclizumab (ZENAPAX®), ibritumomab tiuxetan (ZEVALIN®), eculizumab (SOLIRIS®), ipilimumab (YERVOY®), muromonab-CD3 (ORTHOCLONE OKT3®), raxibacumab, nimotuzumab (THERACIM®), brentuximab vedotin (ADCETRIS®), adalimumab (HUMIRA®), golimumab (SIMPONI®), palivizumab (SYNAGIS®), omalizumab (XOLAIR®), and ustekinumab (STELARA®).

Natalizumab, a humanized mAb against the cell adhesion molecule α4-integrin, is used in the treatment of multiple sclerosis and Crohn's disease. Previously marketed under the trade name ANTEGREN®, natalizumab is currently co-marketed as TYSABRI® by Biogen Idec ("Biogen") and Elan Corp. ("Elan") TYSABRI® is produced in murine myeloma cells. Each 15 mL dose contains 300 mg natalizumab; 123 mg sodium chloride, USP; 17.0 mg sodium phosphate, monobasic, monohydrate, USP; 7.24 mg sodium phosphate, dibasic, heptahydrate, USP; 3.0 mg polysorbate 80, USP/NF, in water for IV injection, USP at pH 6.1. Natalizumab is typically administered by monthly intravenous (IV) infusions and has been proven effective in treating the symptoms of both multiple sclerosis and Crohn's disease, as well as for preventing relapse, vision loss, cognitive decline, and significantly improving patient's quality of life.

As used herein, the term "natalizumab" includes the mAb against the cell adhesion molecule α4-integrin known under the International Nonproprietary Name "NATALIZUMAB" or an antigen binding portion thereof. Natalizumab includes antibodies described in U.S. Pat. Nos. 5,840,299, 6,033,665, 6,602,503, 5,168,062, 5,385,839, and 5,730,978. Natalizumab includes the active agent in products marketed under the trade name TYSABRI® by Biogen Idec and Elan Corporation or a biosimilar product thereof.

Cetuximab is an epidermal growth factor receptor (EGFR) inhibitor used for the treatment of metastatic colorectal cancer and head and neck cancer. Cetuximab is a chimeric (mouse/human) mAb typically given by IV infusion. Cetuximab is marketed for IV use only under the trade name ERBITUX® by Bristol-Myers Squibb Company (North America; "Bristol-Myers Squibb"), Eli Lilly and Company (North America; "Eli Lilly"), and Merck KGaA. ERBITUX® is produced in mammalian (murine myeloma) cell culture. Each single-use, 50-mL vial of ERBITUX® contains 100 mg of cetuximab at a concentration of 2 mg/mL and is formulated in a preservative-free solution containing 8.48 mg/mL sodium chloride, 1.88 mg/mL sodium phosphate dibasic heptahydrate, 0.42 mg/mL sodium phosphate monobasic monohydrate, and water for IV Injection, USP.

Cetuximab is indicated for the treatment of patients with epidermal growth factor receptor (EGFR)-expressing, KRAS wild-type metastatic colorectal cancer (mCRC), in combination with chemotherapy, and as a single agent in patients who have failed oxaliplatin- and irinotecan-based therapy or who are intolerant to irinotecan. Cetuximab is indicated for the treatment of patients with squamous cell carcinoma of the head and neck in combination with platinum-based chemotherapy for the first-line treatment of recurrent and/or metastatic disease and in combination with radiation therapy for locally advanced disease. Approximately 75% of patients with metastatic colorectal cancer have an EGFR-expressing tumor and are, therefore, considered eligible for treatment with cetuximab or panitumumab, according to FDA guidelines.

As used herein, the term "cetuximab" includes the mAb known under the International Nonproprietary Name "CETUXIMAB" or an antigen binding portion thereof. Cetuximab includes antibodies described in U.S. Pat. No. 6,217,866. Cetuximab includes the active agent in products marketed under the trade name ERBITUX® and biosimilar products thereof. Biosimilars of ERBITUX® can include those currently being developed by Amgen, AlphaMab Co., Ltd. ("AlphaMab"), and Actavis plc ("Actavis").

Bevacizumab, a humanized mAb that inhibits vascular endothelial growth factor A (VEGF-A), acts as an anti-angiogenic agent. It is marketed under the trade name AVASTIN® by Genentech, Inc. ("Genentech") and F. Hoffmann-La Roche, LTD ("Roche"). It is licensed to treat various cancers, including colorectal, lung, breast (outside the U.S.A.), glioblastoma (U.S.A. only), kidney and ovarian. AVASTIN® was approved by the FDA in 2004 for use in metastatic colorectal cancer when used with standard chemotherapy treatment (as first-line treatment) and with 5-fluorouracil-based therapy for second-line metastatic colorectal cancer. In 2006, the FDA approved AVASTIN® for use in first-line advanced non-squamous non-small cell lung cancer in combination with carboplatin/paclitaxel chemotherapy. AVASTIN® is given as an IV infusion every three weeks at the dose of either 15 mg/kg or 7.5 mg/kg. The higher dose is usually given with carboplatin-based chemotherapy, whereas the lower dose is given with cisplatin-based chemotherapy. In 2009, the FDA approved AVASTIN® for use in metastatic renal cell carcinoma (a form of kidney cancer). The FDA also granted accelerated approval of AVASTIN® for the treatment of recurrent glioblastoma multiforme in 2009. Treatment for initial growth is still in phase III clinical trial.

The National Comprehensive Cancer Network ("NCCN") recommends bevacizumab as standard first-line treatment in combination with any platinum-based chemotherapy, followed by maintenance bevacizumab until disease progression. The NCCN updated its Clinical Practice Guidelines for Oncology (NCCN Guidelines) for Breast Cancer in 2010 to affirm the recommendation regarding the use of bevacizumab (AVASTIN®, Genentech/Roche) in the treatment of metastatic breast cancer.

As used herein, the term "bevacizumab" includes the mAb that inhibits vascular endothelial growth factor A (VEGF-A) known under the International Nonproprietary Name/Common Name "BEVACIZUMAB" or an antigen binding portion thereof. Bevacizumab is described in U.S. Pat. No. 6,054,297. Bevacizumab includes the active agent in products marketed under the trade name AVASTIN® and biosimilar products thereof. Biosimilars of AVASTIN® can include those currently being developed by Amgen, Actavis, AlphaMab, and Pfizer, Inc ("Pfizer"). Biosimilars of AVASTIN® can include the biosimilar known as BCD-021 produced by Biocad and currently in clinical trials in the U.S.

Trastuzumab is a mAb that interferes with the HER2/neu receptor. Trastuzumab is marketed under the trade name HERCEPTIN® by Genentech, Inc. HERCEPTIN® is produced by a mammalian cell (Chinese Hamster Ovary (CHO)) line. HERCEPTIN® is a sterile, white to pale-yellow, preservative-free lyophilized powder for IV administration. Each HERCEPTIN® vial contains 440 mg trastuzumab, 9.9 mg L-histidine HCl, 6.4 mg L-histidine, 400 mg a,a-trehalose dihydrate, and 1.8 mg polysorbate 20, USP. Reconstitution with 20 mL water yields a multi-dose solution containing 21 mg/mL trastuzumab. HERCEPTIN® is currently administered via IV infusion as often as weekly and at a dosage ranging from about 2 mg/kg to about 8 mg/kg.

Trastuzumab is mainly used to treat certain breast cancers. The HER2 gene is amplified in 20-30% of early-stage breast cancers, which makes it overexpress epidermal growth factor (EGF) receptors in the cell membrane. Trastuzumab is generally administered as a maintenance therapy for patients with HER2-positive breast cancer, typically for one year post-chemotherapy. Trastuzumab is currently administered via IV infusion as often as weekly and at a dosage ranging from about 2 mg/kg to about 8 mg/kg.

As used herein, the term "trastuzumab" includes the mAb that interferes with the HER2/neu receptor known under the International Nonproprietary Name/Common Name "TRASTUZUMAB" or an antigen binding portion thereof. Trastuzumab is described in U.S. Pat. No. 5,821,337. Trastuzumab includes the active agent in products marketed under the trade name HERCEPTIN® and biosimilars thereof. The term "trastuzumab" includes the active agent in biosimilar HERCEPTIN® products marketed under the trade names HERTRAZ® by Mylan, Inc. ("Mylan") and CANMAB® by Biocon, Ltd. ("Biocon"). Trastuzumab can include the active agent in biosimilar HERCEPTIN® products being developed by Amgen and by PlantForm Corporation, Canada.

Infliximab is a mAb against tumor necrosis factor alpha (TNF-α) used to treat autoimmune diseases. It is marketed under the trade name REMICADE® by Janssen Global Services, LLC ("Janssen") in the U.S., Mitsubishi Tanabe Pharma in Japan, Xian Janssen in China, and Merck & Co ("Merck"); elsewhere. Infliximab is a chimeric mouse/human monoclonal antibody with a high molecular weight of approximately 144 kDa. In some embodiments, the formulations contain a biosimilar of REMICADE®, such as REMSIMA™ or INFLECTRA™. Both REMSIMA™, developed by Celltrion, Inc. ("Celltrion"), and INFLECTRA™, developed by Hospira Inc, UK, have been recommended for regulatory approval in Europe. Celltrion has submitted a filing for REMSIMA™ to the FDA. Infliximab is currently administered via IV infusion at doses ranging from about 3 mg/kg to about 10 mg/kg.

Infliximab contains approximately 30% murine variable region amino acid sequence, which confers antigen-binding specificity to human TNFα. The remaining 70% correspond to a human IgG1 heavy chain constant region and a human kappa light chain constant region. Infliximab has high affinity for human TNFα, which is a cytokine with multiple biologic actions including mediation of inflammatory responses and modulation of the immune system.

Infliximab is a recombinant antibody generally produced and secreted from mouse myeloma cells (SP2/0 cells). The antibody is currently manufactured by continuous perfusion cell culture. The infliximab monoclonal antibody is expressed using chimeric antibody genes consisting of the variable region sequences cloned from the murine anti-TNFα hybridoma A2, and human antibody constant region sequences supplied by the plasmid expression vectors. Generation of the murine anti-TNF a hybridoma is performed by immunization of BALB/c mice with purified recombinant human TNFα. The heavy and light chain vector constructs are linearized and transfected into the Sp2/0 cells by electroporation. Standard purification steps can include chromatographic purification, viral inactivation, nanofiltration, and ultrafiltration/diafiltration.

As used herein, the term "infliximab" includes the chimeric mouse/human monoclonal antibody known under the International Nonproprietary Name "INFLIXIMAB" or an antigen binding portion thereof. Infliximab neutralizes the biological activity of TNFα by binding with high affinity to the soluble and transmembrane forms of TNFα and inhibits binding of TNFα with its receptors. Infliximab is described in U.S. Pat. No. 5,698,195. The term "Infliximab" includes the active agent in products marketed or proposed to be marketed under the trade names REMICADE® by multiple entities; REMSIMA™ by Celltrion and INFLECTRA™ by Hospira, Inc ("Hospira"). Infliximab is supplied as a sterile lyophilized cake for reconstitution and dilution. Each vial of infliximab contains 100 mg infliximab and excipients such as monobasic sodium phosphate monohydrate, dibasic sodium phosphate dihydrate, sucrose, and polysorbate 80.

Denosumab (PROLIA® and XGEVA®) is a human mAb—and the first RANKL inhibitor—approved for use in postmenopausal women with risk of osteoporosis and patients with bone metastases from solid tumors. Denosumab is in Phase II trials for the treatment of rheumatoid arthritis.

Panitumumab is a fully human mAb approved by the FDA for treatment of EGFR-expressing metastatic cancer with disease progression. Panitumumab is marketed under the trade name VECTIBIX® by Amgen. VECTIBIX® is packaged as a 20 mg/ml panitumumab concentrate in 5 ml, 10 ml, and 15 ml vials for IV infusion. When prepared according to the packaging instructions, the final panitumumab concentration does not exceed 10 mg/ml. VECTIBIX® is administered at a dosage of 6 mg/kg every 14 days as an intravenous infusion. As used herein, the term "panitumumab" includes the anti-human epidermal growth factor receptor known by the International Nonproprietary Name "PANITUMUMAB." The term "panitumumab" includes the active agent in products marketed under the trade name VECTIBIX® by Amgen and biosimilars thereof. The term "panitumumab" includes monoclonal antibodies described in U.S. Pat. No. 6,235,883. The term "panitumumab" includes the active agent in biosimilar VECTIBIX® products, including biosimilar VECTIBIX® being developed by BioXpress, SA ("BioXpress").

Belimumab (BENLYSTA®) is a human mAb with a molecular weight of about 151.8 kDa that inhibits B-cell activating factor (BAFF). Belimumab is approved in the United States, Canada, and Europe for treatment of systemic lupus erythematosus. Belimumab is currently administered to lupus patients by IV infusion at a 10 mg/kg dosage. A high-molecular-weight, low-viscosity protein formulation can include Belimumab, preferably in a concentration of about 400 mg/mL to about 1,000 mg/mL. The preferred ranges are calculated based upon body weight of 40-100 kg (approximately 80-220 lbs) in a 1 mL volume.

Abciximab (REOPRO®) is manufactured by Janssen Biologics BV and distributed by Eli Lilly & Company ("Eli Lilly"). Abciximab is a Fab fragment of the chimeric human-murine monoclonal antibody 7E3. Abciximab binds to the glycoprotein (GP) IIb/IIIa receptor of human platelets and inhibits platelet aggregation by preventing the binding of fibrinogen, von Willebrand factor, and other adhesive molecules. It also binds to vitronectin ($\alpha v\beta 3$) receptor found on platelets and vessel wall endothelial and smooth muscle cells. Abciximab is a platelet aggregation inhibitor mainly used during and after coronary artery procedures. Abciximab is administered via IV infusion, first in a bolus of 0.25 mg/kg and followed by continuous IV infusion of 0.125 mcg/kg/minute for 12 hours.

Tositumomab (BEXXAR®) is a drug for the treatment of follicular lymphoma. It is an IgG2a anti-CD20 mAb derived from immortalized mouse cells. Tositumomab is administered in sequential infusions: cold mAb followed by iodine (131I) tositumomab, the same antibody covalently bound to the radionuclide iodine-131. Clinical trials have established the efficacy of the tositumomab/iodine tositumomab regimen in patients with relapsed refractory follicular lymphoma. BEXXAR® is currently administered at a dose of 450 mg via IV infusion.

Alemtuzumab (marketed as CAMPATH®, MABCAMPATH®, or CAMPATH-1H® and currently under further development as LEMTRADA®) is a mAb used in the treatment of chronic lymphocytic leukemia (CLL), cutaneous T-cell lymphoma (CTCL), and T-cell lymphoma. It is also used under clinical trial protocols for treatment of some autoimmune diseases, such as multiple sclerosis. Alemtuzumab has a weight of approximately 145.5 kDa. It is administered in daily IV infusions of 30 mg for patients with B-cell chronic lymphocytic leukemia.

Palivizumab (SYNAGIS®) is a humanized mAb directed against an epitope in the A antigenic site of the F protein of respiratory syncytial virus. In two Phase III clinical trials in the pediatric population, palivizumab reduced the risk of hospitalization due to respiratory syncytial virus infection by 55% and 45%. Palivizumab is dosed once a month via IM injection of 15 mg/kg.

Ofatumumab is a human anti-CD20 mAb which appears to inhibit early-stage B lymphocyte activation. Ofatumumab is marketed under the trade name ARZERRA® by GlaxoSmithKline, plc ("GlaxoSmithKline"). ARZERRA® is distributed in single-use vials containing 100 mg/5 mL and 1,000 mg/50 mL ofatumumab for IV infusion. Ofatumumab is FDA-approved for treating chronic lymphocytic leukemia and has also shown potential in treating Follicular non-Hodgkin's lymphoma, Diffuse large B cell lymphoma, rheumatoid arthritis, and relapsing remitting multiple sclerosis. Ofatumumab has a molecular weight of about 149 kDa. It is currently administered by IV infusion at an initial dose of 300 mg, followed by weekly infusions of 2,000 mg. As used herein, the term "ofatumumab" includes the anti-CD20 mAb known by the International Nonproprietary Name "OFATUMUMAB." The term "ofatumumab" includes the active agent in products marketed under the trade name ARZERRA® and biosimilars thereof. The term "ofatumumab" includes the active agent in biosimilar ARZERRA® products being developed by BioExpress. High-molecular-weight, low-viscosity liquid protein formulations can include ofatumumab, preferably in a concentration of about 300 mg/mL to about 2,000 mg/mL.

Trastuzumab emtansine (in the U.S., ado-trastuzumab emtansine, marketed as KADCYLA®) is an antibody-drug conjugate consisting of the mAb trastuzumab linked to the cytotoxic agent mertansine (DM1®). Trastuzumab, described above, stops growth of cancer cells by binding to the HER2/neu receptor, whereas mertansine enters cells and destroys them by binding to tubulin. In the United States, trastuzumab emtansine was approved specifically for treatment of recurring HER2-positive metastatic breast cancer. Multiple Phase III trials of trastuzumab emtansine are planned or ongoing in 2014. Trastuzumab emtansine is currently administered by IV infusion of 3.6 mg/kg. High-molecular-weight, low-viscosity liquid formulations can include trastuzumab emtansine, preferably in a concentration of about 144 mg/mL to about 360 mg/mL.

Pertuzumab (PERJETA®) is a mAb that inhibits HER2 dimerization. Pertuzumab received FDA approval for the treatment of HER2-positive metastatic breast cancer in 2012. The currently recommended dosage of Pertuzumab is 420 mg to 840 mg by IV infusion. High-molecular-weight, low-viscosity liquid formulations can include pertuzumab, preferably in a concentration of about 420 mg/mL to about 840 mg/mL.

Daclizumab is a humanized anti-CD25 mAb and is used to prevent rejection in organ transplantation, especially in kidney transplants. The drug is also under investigation for the treatment of multiple sclerosis. Daclizumab has a molecular weight of about 143 kDa. Daclizumab was marketed in the U.S. by Hoffmann-La Roche, Ltd. ("Roche") as ZENAPAX® and administered by IV infusion of 1 mg/kg. Daclizumab High-Yield Process (DAC HYP; BIIB019; Biogen Idec ("Biogen") and AbbVie, Inc. ("AbbVie")) is in phase III clinical trials as a 150 mg, once-monthly subcutaneous injection to treat relapsing, remitting multiple-sclerosis. High-molecular-weight, low-viscosity liquid formulations can include daclizumab, preferably in a concentration of about 40 mg/mL to about 300 mg/mL.

Eculizumab (SOLIRIS®) is a humanized mAb approved for the treatment of rare blood diseases, such as paroxysmal nocturnal hemoglobinuria and atypical hemolytic uremic syndrome. Eculizumab, with a molecular weight of about 148 kDa, is being developed by Alexion Pharmaceuticals, Inc ("Alexion"). It is administered by IV infusion in the amount of about 600 mg to about 1,200 mg. High-molecular-weight, low-viscosity liquid formulations can include eculizumab, preferably in a concentration of about 500 mg/mL to about 1,200 mg/mL.

Tocilizumab (ACTEMRA®) is a humanized mAb against the interleukin-6 receptor. It is an immunosuppressive drug, mainly for the treatment of rheumatoid arthritis (RA) and systemic juvenile idiopathic arthritis, a severe form of RA in children. Tocilizumab is commonly administered by IV infusion in doses of about 6 mg/kg to about 8 mg/kg. High-molecular-weight, low-viscosity liquid formulations can include tocilizumab, preferably in a concentration of about 240 mg/mL to about 800 mg/mL.

Rituximab (RITUXAN®) is a chimeric anti-CD20 mAb used to treat a variety of diseases characterized by excessive numbers of B cells, overactive B cells, or dysfunctional B cells. Rituximab is used to treat cancers of the white blood system, such as leukemias and lymphomas, including Hodgkin's lymphoma and its lymphocyte-predominant subtype. It has been shown to be an effective rheumatoid arthritis treatment. Rituximab is widely used off-label to treat difficult cases of multiple sclerosis, systemic lupus erythematosus, and autoimmune anemias.

Rituximab is jointly marketed in the U.S. under the trade name RITUXAN® by Biogen and Genentech and outside the U.S. under the trade name MABTHERA® by Roche. RITUXAN® is distributed in single-use vials containing 100 mg/10 mL and 500 mg/50 mL. RITUXAN® is typically administered by IV infusion of about 375 mg/m². The term "rituximab," as used herein, includes the anti-CD20 mAb known under the International Nonproprietary Name/Common Name "RITUXIMAB." Rituximab includes mAbs described in U.S. Pat. No. 5,736,137. Rituximab includes the active agent in products marketed under the trade name RITUXAN® and MABTHERA® and biosimilars thereof.

High-molecular-weight, low-viscosity liquid formulations can include rituximab, preferably in a concentration of about 475 mg/mL to about 875 mg/mL (approximated using a body surface area range of 1.3 to 2.3 square meters, derived from the Mosteller formula for persons ranging from 5 ft, 40 kg to 6 ft, 100 kg). Concentrations are calculated for a 1 mL formulation.

Ipilimumab is a human mAb developed by Bristol-Myers Squibb Company ("Bristol-Myers Squibb"). Marketed as YERVOY®, it is used for the treatment of melanoma and is also undergoing clinical trials for the treatment of non-small cell lung carcinoma (NSCLC), small cell lung cancer (SCLC), and metastatic hormone-refractory prostate cancer. Ipilimumab is currently administered by IV infusion of 3 mg/kg. High-molecular-weight, low-viscosity liquid formulations can include ipilimumab, preferably in a concentration of about 120 mg/mL to about 300 mg/mL.

Raxibacumab (ABthrax®) is a human mAb intended for the prophylaxis and treatment of inhaled anthrax. It is currently administered by IV infusion. The suggested dosage in adults and children over 50 kg is 40 mg/kg. High-molecular-weight, low-viscosity liquid formulations can include raxibacumab, preferably in a concentration of about 1,000 mg/mL to about 4,000 mg/mL.

Nimotuzumab (THERACIM®, BIOMAB EGFR®, THERALOC®, CIMAher®) is a humanized mAb with a molecular weight of about 151 kDa used to treat squamous cell carcinomas of the head and neck, recurrent or refractory high-grade malignant glioma, anaplastic astrocytomas, glioblastomas, and diffuse intrinsic pontine glioma. Nimotuzumab is typically administered by IV infusion of about 200 mg weekly. High-molecular-weight, low-viscosity liquid formulations can include nimotuzumab, preferably in a concentration of about 200 mg/mL.

Brentuximab vedotin (ADCETRIS®) is an antibody-drug conjugate directed to the protein CD30, expressed in classical Hodgkin's lymphoma and systemic anaplastic large cell lymphoma. It is administered by IV infusion of about 1.8 mg/kg. High-molecular-weight, low-viscosity liquid formulations can include brentuximab vedotin, preferably in a concentration of about 80 mg/mL to about 200 mg/mL.

Itolizumab (ALZUMAB®) is a humanized IgG1 mAb developed by Biocon. Itolizumab completed successful Phase III studies in patients with moderate to severe psoriasis. Itolizumab has received marketing approval in India; an application for FDA approval has not been submitted.

Obinutuzumab (GAZYVA®), originally developed by Roche and being further developed under a collaboration agreement with Biogen is a humanized anti-CD20 mAb approved for treatment of chronic lymphocytic leukemia. It is also being investigated in Phase III clinical trials for patients with various lymphomas. Dosages of about 1,000 mg are being administered via IV infusion.

Certolizumab pegol (CIMZIA®) is a recombinant, humanized antibody Fab' fragment, with specificity for human tumor necrosis factor alpha (TNFα), conjugated to an approximately 40 kDa polyethylene glycol (PEG2MAL40K). The molecular weight of certolizumab pegol is approximately 91 kDa.

Other antibody therapeutics that can be formulated with viscosity-lowering agents include CT-P6 from Celltrion, Inc. (Celltrion).

Antibody Therapeutics in Late-Stage Trials and Development

The progression of antibody therapeutics to late-stage clinical development and regulatory review are proceeding at a rapid pace. In 2014, there are more than 300 mAbs in clinical trials and 30 commercially-sponsored antibody therapeutics undergoing evaluation in late-stage studies. First marketing applications for two mAbs (vedolizumab and ramucirumab) were recently submitted to the FDA. Amgen is currently sponsoring multiple ongoing Phase III trials on the use of brodalumab in patients with plaque psoriasis, with additional trials planned or recruiting patients. XBiotech, Inc. has sponsored two Phase I clinical trials of MABp1 (Xilonix) for patients with advanced cancer or type-2 diabetes. Additional trials of MABp1 are recruiting patients. Multiple trials are sponsored by Medlmmune, LLC ("Medlmmune") and underway or recruiting patients for the treatment of leukemia with moxetumomab pasudotox. Long-term safety and efficacy studies are underway for the use of tildrakizumab for the treatment of chronic plaque psoriasis. Multiple phase II trials have recently completed for the use of rilotumumab for the treatment of various cancers.

At least 28 mAbs are high-molecular-weight proteins currently in or having recently completed Phase III studies for the treatment of inflammatory or immunological disorders, cancers, high cholesterol, osteoporosis, Alzheimer's disease, and infectious diseases. The mAbs in or having recently completed Phase III trials include AMG 145, elotuzumab, epratuzumab, farletuzumab (MORAb-003), gantenerumab (RG1450), gevokizumab, inotuzumab ozogamicin, itolizumab, ixekizumab, lebrikizumab, mepolizumab, naptumomab estafenatox, necitumumab, nivolumab, ocrelizumab, onartuzumab, racotumomab, ramucirumab, reslizumab, romosozumab, sarilumab, secukinumab, sirukumab, solanezumab, tabalumab, and vedolizumab. A mAb mixture (actoxumab and bezlotoxumab) is also being evaluated in Phase III trials. See, e.g., Reichert, MAbs 5:1-4, 2013.

Vedolizumab is a mAb being developed by Millennium Pharmaceuticals, Inc ("Millennium"; a subsidiary of Takeda Pharmaceuticals Company, Ltd. ("Takeda")). Vedolizumab was found safe and highly effective for inducing and maintaining clinical remission in patients with moderate to severe ulcerative colitis. Phase III clinical trials showed it to meet the objectives of inducing a clinical response and maintaining remission in Crohn's and ulcerative colitis patients. Studies evaluating long-term clinical outcomes show close to 60% of patients achieving clinical remission. A common dose of vedolizumab are 6 mg/kg by IV infusion.

Ramucirumab is a human mAb being developed for the treatment of solid tumors. Phase III clinical trials are ongoing for the treatment of breast cancer, metastatic gastric adenocarcinoma, non-small cell lung cancer, and other types of cancer. Ramucirumab, in some Phase III trials, is administered at about 8 mg/kg via IV infusion.

Rilotumumab is a human mAb that inhibits the action of hepatocyte growth factor/scatter factor. Developed by Amgen, it is in Phase III trials as a treatment for solid tumors. An open Phase III study of rilotumumab treatment in patients with advanced or metastatic esophageal cancer will administer rilotumumab at about 15 mg/kg via IV infusion.

Evolocumab (AMG 145), also developed by Amgen, is a mAb that binds to PCSK9. Evolocumab is indicated for hypercholesterolemia and hyperlipidemia.

Alirocumab (REGN727) is a human mAb from Regeneron Pharmaceuticals, Inc. ("Regeneron") and Sanofi-Aventis U.S. LLC ("Sanofi"), indicated for hypercholesterolemia and acute coronary syndrome.

Naptumomab estafenatox, ABR-217620 from Active Biotech AB ("Active Biotech") is a mAb indicated for renal cell carcinoma.

Racotumomab from CIMAB, SA ("CIMAB"); Laboratorio Elea S.A.C.I.F.y A. is a mAb indicated for non-small cell lung cancer.

Other antibodies which may be formulated with viscosity-lowering agents include bococizumab (PF-04950615) and tanezumab; ganitumab, blinatumomab, trebananib from Amgen; Anthrax immune globulin from Cangene Corporation; teplizumab from MacroGenics, Inc.; MK-3222, MK-6072 from Merck & Co ("Merck"); girentuximab from Wilex AG; RIGScan from Navidea Biopharmaceuticals ("Navidea"); PF-05280014 from Pfizer; SA237 from Chugai Pharmaceutical Co. Ltd. ("Chugai"); guselkumab from Janssen/Johnson and Johnson Services, Inc. ("J&J"); Antithrombin Gamma (KW-3357) from Kyowa; and CT-P10 from Celltrion.

Antibodies in Early-Stage Clinical Trials

Many mAbs have recently entered, or are entering, clinical trials. They can include proteins currently administered via IV infusion, preferably those having a molecular weight greater than about 120 kDa, typically from about 140 kDa to about 180 kDa. They can also include such high-molecular-weight proteins such as Albumin-conjugated drugs or peptides that are also entering clinical trials or have been approved by the FDA. Many mAbs from Amgen are currently in clinical trials. These can be high-molecular-weight proteins, for example, AMG 557, which is a human monoclonal antibody developed jointly by Amgen and AstraZeneca and currently in Phase I trials for treatment of lupus. Likewise, AMG 729 is a humanized mAb developed by Amgen and currently in Phase I trials for the treatment of lupus and rheumatoid arthritis. In addition, AMG 110 is a mAb for epithelial cell adhesion molecule; AMG 157, jointly developed by Amgen and AstraZeneca, is a human mAb currently in Phase I for the treatment of asthma; AMG 167 is a humanized mAb that has been evaluated in multiple Phase I trials for the treatment of osteopenia; AMG 334, having completed Phase I dosing studies and currently in in Phase II studies for the treatment of migraines and hot flashes, is a human mAb that inhibits Calcitonin Gene-Related Peptide; AMG 780 is a human anti-angiopoietin mAb that inhibits the interaction between the endothelial cell-selective Tie2 receptor and its ligands Ang1 and Ang2, and recently completed Phase I trials as a cancer treatment; AMG 811 is a human monoclonal antibody that inhibits interferon gamma being investigated as a treatment for systemic lupus erythematosus; AMG 820 is a human mAb that inhibits c-fms and decreases tumor associated macrophage (TAM) function and is being investigated as a cancer treatment; AMG 181, jointly developed by Amgen and AstraZeneca, is a human mAb that inhibits the action of alpha4/beta7 and is in Phase II trials as a treatment for ulcerative colitis and Crohn's disease.

Many mAbs are currently in clinical trials for the treatment of autoimmune disorders. These mAbs can be included in low-viscosity, high-molecular-weight liquid formulations. RG7624 is a fully human mAb designed to specifically and selectively bind to the human interleukin-17 family of cytokines. A Phase I clinical trial evaluating RG7624 for autoimmune disease is ongoing. BIIB033 is an anti-LINGO-1 mAb by Biogen currently in Phase II trials for treating multiple sclerosis.

High-molecular-weight proteins also can include AGS-009, a mAb targeting IFN-alpha developed by Argos Therapeutics, Inc. that recently completed phase I trials for the treatment of lupus. Patients are administered up to 30 mg/kg of AGS-009 via IV infusion. BT-061, developed by AbbVie, is in Phase II trials for patients with rheumatoid arthritis. Certolizumab pegol (CIMZIA®) is a mAb in Phase II trials for ankylosing spondylitis and juvenile rheumatoid arthritis. Clazakizumab, an anti-IL6 mAb, is in Phase II trials by Bristol-Myers Squibb.

CNTO-136 (sirukumab) and CNTO-1959 are mABs having recently completed Phase II and Phase III trials by Janssen. Daclizumab (previously marketed as ZENAPAX® by Roche) is currently in or has recently completed multiple Phase III trials by AbbVie for the treatment of multiple sclerosis. Epratuzumab is a humanized mAb in Phase III trials for the treatment of lupus. Canakinumab (ILARIS®) is a human mAb targeted at interleukin-1 beta. It was approved for the treatment of cryopyrin-associated periodic syndromes. Canakinumab is in Phase I trials as a possible treatment for chronic obstructive pulmonary disease, gout and coronary artery disease. Mavrilimumab is a human mAb designed for the treatment of rheumatoid arthritis. Discovered as CAM-3001 by Cambridge Antibody Technology, mavrilimumab is being developed by MedImmune.

MEDI-546 are MEDI-570 are mAbs currently in Phase I and Phase II trials by AstraZeneca for the treatment of lupus. MEDI-546 is administered in the Phase II study by regular IV infusions of 300-1,000 mg. MEDI-551, another mAb being developed by AstraZeneca for numerous indications, is also currently administered by IV infusion. NN8209, a mAb blocking the C5aR receptor being developed by Novo Nordisk A/S("Novo Nordisk"), has completed a Phase II dosing study for treatment of rheumatoid arthritis. NN8210 is another antiC5aR mAb being developed by Novo Nordisk and currently is in Phase I trials. IPH2201 (NN8765) is a humanized mAb targeting NKG2A being developed by Novo Nordisk to treat patients with inflammatory conditions and autoimmune diseases. NN8765 recently completed Phase I trials.

Olokizumab is a humanized mAb that potently targets the cytokine IL-6. IL-6 is involved in several autoimmune and inflammatory pathways. Olokizumab has completed Phase II trials for the treatment of rheumatoid arthritis. Otelixizumab, also known as TRX4, is a mAb, which is being developed for the treatment of type 1 diabetes, rheumatoid arthritis, and other autoimmune diseases. Ozoralizumab is a humanized mAb that has completed Phase II trials.

Pfizer currently has Phase I trials for the mAbs PD-360324 and PF-04236921 for the treatment of lupus. A rituximab biosimilar, PF-05280586, has been developed by Pfizer and is in Phase I/Phase II trials for rheumatoid arthritis.

Rontalizumab is a humanized mAb being developed by Genentech. It recently completed Phase II trials for the treatment of lupus. SAR113244 (anti-CXCR5) is a mAb by Sanofi in Phase I trials. Sifalimumab (anti-IFN-alpha mAb) is a mAb in Phase II trials for the treatment of lupus.

A high-molecular-weight low-viscosity liquid formulation can include one of the mAbs in early stage clinical development for treating various blood disorders. For example, Belimumab (BENLYSTA®) has recently completed Phase I trials for patients with vasculitis. Other mAbs in early-stage trials for blood disorders include BI-655075 from Boehringer Ingelheim GmbH "Boehringer Ingelheim", ferroportin mAb and hepcidin mAb from Eli Lily, and SelG1 from Selexys Pharmaceuticals, Corp. ("Selexys").

One or more mAbs in early-stage development for treating various cancers and related conditions can be included in a low-viscosity, high-molecular-weight liquid formulation. United Therapeutics, Corporation has two mAbs in Phase I trials, 8H9 mAb and ch14.18 mAb. The mAbs ABT-806, enavatuzumab, and volociximab from AbbVie are in early-stage development. Actinium Pharmaceuticals, Inc has conducted early-stage trials for the mAbs Actimab-A (M195 mAb), anti-CD45 mAb, and Iomab-B. Seattle Genetics, Inc. ("Seattle Genetics") has several mAbs in early-stage trials for cancer and related conditions, including anti-CD22 ADC (RG7593; pinatuzumab vedotin), anti-CD79b ADC (RG7596), anti-STEAP1 ADC (RG7450), ASG-5ME and ASG-22ME from Agensys, Inc. ("Agensys") the antibody-drug conjugate RG7458, and vorsetuzumab mafodotin. The early-stage cancer therapeutics from Genentech can be included in low-viscosity formulations, including ALT-836, the antibody-drug conjugates RG7600 and DEDN6526A, anti-CD22 ADC (RG7593), anti-EGFL7 mAb (RG7414), anti-HER3/EGFR DAF mAb (RG7597), anti-PD-L1 mAb (RG7446), DFRF4539A, an MINT1526A. Bristol-Myers Squibb is developing early-stage mAbs for cancer therapeutics, including those identified as anti-CXCR4, anti-PD-L1, IL-21 (BMS-982470), lirilumab, and urelumab (anti-CD137). Other mAbs in early-stage trials as cancer therapeutics include APN301(hu14.18-IL2) from Apeiron Biologics AG, AV-203 from AVEO Pharmaceuticals, Inc. ("AVEO"), AVX701 and AVX901 from AlphaVax, BAX-69 from Baxter International, Inc. ("Baxter"), BAY 79-4620 and BAY 20-10112 from Bayer HealthCare AG, BHQ880 from Novartis AG, 212-Pb-TCMCtrastuzumab from AREVA Med, AbGn-7 from AbGenomics International Inc, and ABIO-0501 (TALL-104) from Abiogen Pharma S.p.A.

Other antibody therapeutics that can be formulated with viscosity-lowering agents include alzumab, GA101, daratumumab, siltuximab, ALX-0061, ALX-0962, ALX-0761, bimagumab (BYM338), CT-011 (pidilizumab), actoxumab/bezlotoxumab (MK-3515A), MK-3475 (pembrolizumab), dalotuzumab (MK-0646), icrucumab (IMC-18F1, LY3012212), AMG 139 (MEDI2070), SAR339658, dupilumab (REGN668), SAR156597, SAR256212, SAR279356, SAR3419, SAR153192 (REGN421, enoticumab), SAR307746 (nesvacumab), SAR650984, SAR566658, SAR391786, SAR228810, SAR252067, SGN-CD19A, SGN-CD33A, SGN-LIV1A, ASG 15ME, Anti-LINGO, BIIB037, ALXN1007, teprotumumab, concizumab, anrukinzumab (IMA-638), ponezumab (PF-04360365), PF-03446962, PF-06252616, etrolizumab (RG7413), quilizumab, ranibizumab, lampalizumab, onclacumab, gentenerumab, crenezumab (RG7412), IMC-RON8 (narnatumab), tremelimumab, vantictumab, eemcizumab, ozanezumab, mapatumumab, tralokinumab, XmAb5871, XmAb7195, cixutumumab (LY3012217), LY2541546 (blosozumab), olaratumab (LY3012207), MEDI4893, MEDI573, MEDI0639, MEDI3617, MEDI4736, MEDI6469, MEDI0680, MEDI5872, PF-05236812 (AAB-003), PF-05082566, BI 1034020, RG7116, RG7356, RG7155, RG7212, RG7599, RG7636, RG7221, RG7652 (MPSK3169A), RG7686, HuMaxTFADC, MOR103, BT061, MOR208, OMP59R5 (anti-notch 2/3), VAY736, MOR202, BAY94-9343, LJM716, OMP52M51, GSK933776, GSK249320, GSK1070806, NN8828, CEP-37250/KHK2804 AGS-16M8F, AGS-16C3F, LY3016859, LY2495655, LY2875358, and LY2812176.

Other early stage mAbs that can be formulated with viscosity-lowering agents include benralizumab, MEDI-8968, anifrolumab, MEDI7183, sifalimumab, MEDI-575, tralokinumab from AstraZeneca and MedImmune; BAN2401 from Biogen Idec/Eisai Co. LTD ("Eisai")/Bio-Arctic Neuroscience AB; CDP7657 an anti-CD40L monovalent pegylated Fab antibody fragment, STX-100 an anti-αvB6 mAb, BIIB059, Anti-TWEAK (BIIB023), and BIIB022 from Biogen; fulranumab from Janssen and Amgen; BI-204/RG7418 from BioInvent International/Genentech; BT-062 (indatuximab ravtansine) from Biotest Pharmaceuticals Corporation; XmAb from Boehringer Ingelheim/Xencor; anti-IP10 from Bristol-Myers Squibb; J 591 Lu-177 from BZL Biologics LLC; CDX-011 (glembatumumab vedotin), CDX-0401 from Celldex Therapeutics; foravirumab from Crucell; tigatuzumab from Daiichi Sankyo Company Limited; MORAb-004, MORAb-009 (ama-tuximab) from Eisai; LY2382770 from Eli Lilly; DI17E6 from EMD Serono Inc; zanolimumab from Emergent Bio-Solutions, Inc.; FG-3019 from FibroGen, Inc.; catumaxomab from Fresenius SE & Co. KGaA; pateclizumab, rontalizumab from Genentech; fresolimumab from Genzyme & Sanofi; GS-6624 (simtuzumab) from Gilead; CNTO-328, bapineuzumab (AAB-001), carlumab, CNTO-136 from Janssen; KB003 from KaloBios Pharmaceuticals, Inc.; ASKP1240 from Kyowa; RN-307 from Labrys Biologics Inc.; ecromeximab from Life Science Pharmaceuticals; LY2495655, LY2928057, LY3015014, LY2951742 from Eli Lilly; MBL-HCV1 from MassBiologics; AME-133v from MENTRIK Biotech, LLC; abituzumab from Merck KGaA; MM-121 from Merrimack Pharmaceuticals, Inc.; MCS110, QAX576, QBX258, QGE031 from Novartis AG; HCD122 from Novartis AG and XOMA Corporation ("XOMA"); NN8555 from Novo Nordisk; bavituximab, cotara from Peregrine Pharmaceuticals, Inc.; PSMA-ADC from Progenics Pharmaceuticals, Inc.; oregovomab from Quest Pharmatech, Inc.; fasinumab (REGN475), REGN1033, SAR231893, REGN846 from Regeneron; RG7160, CIM331, RG7745 from Roche; ibalizumab (TMB-355) from TaiMed Biologics Inc.; TCN-032 from Theraclone Sciences; TRC105 from TRACON Pharmaceuticals, Inc.; UB-421 from United Biomedical Inc.; VB4-845 from Viventia Bio, Inc.; ABT-110 from AbbVie; Caplacizumab, Ozoralizumab from Ablynx; PRO 140 from CytoDyn, Inc.; GS-CDA1, MDX-1388 from Medarex, Inc.; AMG 827, AMG 888 from Amgen; ublituximab from TG Therapeutics Inc.; TOL101 from Tolera Therapeutics, Inc.; huN901-DM1 (lorvotuzumab mertansine) from ImmunoGen Inc.; epratuzumab Y-90/veltuzumab combination (IMMU-102) from Immunomedics, Inc.; anti-fibrin mAb/3B6/22 Tc-99m from Agenix, Limited; ALD403 from Alder Biopharmaceuticals, Inc.; RN6G/PF-04382923 from Pfizer; CG201 from CG Therapeutics, Inc.; KB001-A from KaloBios Pharmaceuticals/Sanofi; KRN-23 from Kyowa.; Y-90 hPAM 4 from Immunomedics, Inc.; Tarextumab from Morphosys AG & OncoMed Pharmacetuicals, Inc.; LFG316 from Morphosys AG & Novartis AG; CNTO3157, CNTO6785 from Morphosys AG & Jannsen; RG6013 from Roche & Chugai; MM-111 from Merrimack Pharmaceuticals, Inc. ("Merrimack"); GSK2862277 from GlaxoSmithKline; AMG 282, AMG 172, AMG 595, AMG 745, AMG 761 from Amgen; BVX-20 from Biocon; CT-P19, CT-P24, CT-P25, CT-P26, CT-P27, CT-P4 from Celltrion; GSK284933, GSK2398852, GSK2618960, GSK1223249, GSK933776A from GlaxoSmithKline; anetumab ravtansine from Morphosys AG & Bayer AG; BI-836845 from Morphosys AG & Boehringer Ingelheim; NOV-7, NOV-8 from Morphosys AG & Novartis AG; MM-302, MM-310, MM-141, MM-131, MM-151 from Merrimack, RG7882 from Roche & Seattle Genetics; RG7841 from Roche/Genentech; PF-06410293, PF-06438179, PF-06439535, PF-04605412, PF-05280586 from Pfizer; RG7716, RG7936, gentenerumab, RG7444 from Roche; MEDI-547, MEDI-565, MEDI1814, MEDI4920, MEDI8897, MEDI-4212, MEDI-5117, MEDI-7814 from Astrazeneca; ulocuplumab, PCSK9 adnectin from Bristol-Myers Squibb; FPA009, FPA145 from FivePrime Therapeutics, Inc.; GS-5745 from Gilead; BIW-8962, KHK4083, KHK6640 from Kyowa Hakko Kirin; MM-141 from Merck KGaA; REGN1154, REGN1193, REGN1400, REGN1500, REGN1908-1909, REGN2009, REGN2176-3, REGN728 from Regeneron; SAR307746 from Sanofi; SGN-CD70A from Seattle Genetics; ALX-0141, ALX-0171 from Ablynx; milatuzumab-DOX, milatuzumab, TF2, from Immunomedics, Inc.; MLN0264 from Millennium; ABT-981 from AbbVie; AbGn-168H from AbGenomics International Inc.; ficlatuzumab from AVEO; BI-505 from BioInvent International; CDX-1127, CDX-301 from Celldex Therapeutics; CLT-008 from Cellerant Therapeutics Inc.; VGX-100 from Circadian; U3-1565 from Daiichi Sankyo Company Limited; DKN-01 from Dekkun Corp.; flanvotumab (TYRP1 protein), IL-1β antibody, IMC-CS4 from Eli Lilly; VEGFR3 mAb, IMC-TR1 (LY3022859) from Eli Lilly and ImClone, LLC; Anthim from Elusys Therapeutics Inc.; HuL2G7 from Galaxy Biotech LLC; IMGB853, IMGN529 from ImmunoGen Inc.; CNTO-5, CNTO-5825 from Janssen; KD-247 from Kaketsuken; KB004 from Kalo-Bios Pharmaceuticals; MGA271, MGAH22 from MacroGenics, Inc.; XmAb5574 from MorphoSys AG/Xencor; ensituximab (NPC-1C) from Neogenix Oncology, Inc.; LFA102 from Novartis AG and XOMA; ATI355 from Novartis AG; SAN-300 from Santarus Inc.; SelG1 from Selexys; HuM195/rGel from Targa Therapeutics, Corp.; VX15 from Teva Pharmaceuticals, Industries Ltd. ("Teva") and Vaccinex Inc.; TCN-202 from Theraclone Sciences; XmAb2513, XmAb5872 from Xencor; XOMA 3AB from XOMA and National Institute for Allergy and Infectious Diseases; neuroblastoma antibody vaccine from MabVax Therapeutics; Cytolin from CytoDyn, Inc.; Thravixa from Emergent BioSolutions Inc.; and FB 301 from Cytovance Biologics; rabies mAb from Janssen and Sanofi; flu mAb from Janssen and partly funded by National Institutes of Health; MB-003 and ZMapp from Mapp Biopharmaceutical, Inc.; and ZMAb from Defyrus Inc.

Other Protein Therapeutics

The protein can be an enzyme, a fusion protein, a stealth or pegylated protein, vaccine or otherwise a biologically active protein (or protein mixture). The term "enzyme," as used herein, refers to the protein or functional fragment thereof that catalyzes a biochemical transformation of a target molecule to a desired product.

Enzymes as drugs have at least two important features, namely i) often bind and act on their targets with high affinity and specificity, and ii) are catalytic and convert multiple target molecules to the desired products. In certain embodiments, the protein can be PEGylated, as defined herein.

The term "fusion protein," as used herein, refers to a protein that is created from two different genes encoding for two separate proteins. Fusion proteins are generally produced through recombinant DNA techniques known to those skilled in the art. Two proteins (or protein fragments) are fused together covalently and exhibit properties from both parent proteins.

There are a number of fusion proteins that are on the market.

ENBREL® (Etanercept), is a fusion protein marketed by Amgen that competitively inhibits TNF.

ELOCTATE®, Antihemophilic Factor (Recombinant), Fc Fusion Protein, is a recombinant DNA derived, antihemophilic factor indicated in adults and children with Hemophilia A (congenital Factor VIII deficiency) for control and prevention of bleeding episodes, perioperative management, routine prophylaxis to prevent or reduce the frequency of bleeding episodes.

EYLEA® (aflibercept) is a recombinant fusion protein consisting of portions of human VEGF receptors 1 and 2 extracellular domains fused to the Fc portion of human IgG1 formulated as an iso-osmotic solution for intravitreal administration. EYLEA (aflibercept) is a recombinant fusion protein consisting of portions of human VEGF receptors 1 and 2 extracellular domains fused to the Fc portion of human IgG1 formulated as an iso-osmotic solution for intravitreal administration. Aflibercept is a dimeric glycoprotein with a protein molecular weight of 97 kilodaltons (kDa) and contains glycosylation, constituting an additional 15% of the total molecular mass, resulting in a total molecular weight of 115 kDa. Aflibercept is produced in recombinant Chinese hamster ovary (CHO) cells, marketed by Regeneron.

ALPROLIX™, Coagulation Factor IX (Recombinant), Fc Fusion Protein, is a recombinant DNA derived, coagulation Factor IX concentrate is indicated in adults and children with hemophilia B for control and prevention of bleeding episodes, perioperative management, routine prophylaxis to prevent or reduce the frequency of bleeding episodes.

Pegloticase (KRYSTEXXA®) is a drug for the treatment of severe, treatment-refractory, chronic gout, developed by Savient Pharmaceuticals, Inc. and is the first drug approved for this indication. Pegloticase is a pegylated recombinant porcine-like uricase with a molecular weight of about 497 kDa. Pegloticase is currently administered by IV infusions of about 8 mg/kg. High-molecular-weight, low-viscosity liquid formulations can include pegloticase, preferably in a concentration of about 300 mg/mL to about 800 mg/mL.

Alteplase (ACTIVASE®) is a tissue plasminogen activator produced by recombinant DNA technology. It is a purified glycoprotein comprising 527 amino acids and synthesized using the complementary DNA (cDNA) for natural human tissue-type plasminogen activator obtained from a human melanoma cell line. Alteplase is administered via IV infusion of about 100 mg immediately following symptoms of a stroke. In some embodiments, low-viscosity formulations are provided containing alteplase, preferably in a concentration of about 100 mg/mL.

Glucarpidase (VORAXAZE®) is a FDA-approved drug for the treatment of elevated levels of methotrexate (defined as at least 1 micromol/L) during treatment of cancer patients who have impaired kidney function. Glucarpidase is administered via IV in a single dose of about 50 IU/kg. In some embodiments, low-viscosity formulations are provided containing glucarpidase.

Alglucosidase alfa (LUMIZYME®) is an enzyme replacement therapy orphan drug for treatment of Pompe disease (glycogen storage disease type II), a rare lysosomal storage disorder. It has a molecular weight of about 106 kDa and is currently administered by IV infusions of about 20 mg/kg. In some embodiments, a low-viscosity pharmaceutical formulation of alglucosidase alfa is provided, preferably with a concentration of about 100 mg/mL to about 2,000 mg/mL.

Pegdamase bovine (ADAGEN®) is a modified enzyme used for enzyme replacement therapy for the treatment of severe combined immunodeficiency disease (SCID) associated with a deficiency of adenosine deaminase. Pegdamase bovine is a conjugate of numerous strands of monomethoxy-polyethylene glycol (PEG), molecular weight 5,000 Da, covalently attached to adenosine deaminase enzyme that has been derived from bovine intestine.

α-Galactosidase is a lysosomal enzyme that catalyses the hydrolysis of the glycolipid, globotriaosylceramide (GL-3), to galactose and ceramide dihexoside. Fabry disease is a rare inheritable lysosomal storage disease characterized by subnormal enzymatic activity of α-Galactosidase and resultant accumulation of GL-3. Agalsidase alfa (REPLAGAL®) is a human α-galactosidase A enzyme produced by a human cell line. Agalsidase beta (FABRAZYME®) is a recombinant human α-galactosidase expressed in a CHO cell line. Replagal is administered at a dose of 0.2 mg/kg every other week by intravenous infusion for the treatment of Fabry disease and, off label, for the treatment of Gaucher disease. FABRAZYME® is administered at a dose of 1.0 mg/kg body weight every other week by IV infusion. Other lysosomal enzymes can also be used. For example, the protein can be a lysosomal enzyme as described in US 2012/0148556.

Rasburicase (ELITEK®) is a recombinant urate-oxidase indicated for initial management of plasma uric acid levels in pediatric and adult patients with leukemia, lymphoma, and solid tumor malignancies who are receiving anti-cancer therapy expected to result in tumor lysis and subsequent elevation of plasma uric acid. ELITEK® is administered by daily IV infusion at a dosage of 0.2 mg/kg.

Imiglucerase (CEREZYME®) is a recombinant analogue of human β-glucocerebrosidase. Initial dosages range from 2.5 U/kg body weight 3 times a week to 60 U/kg once every 2 weeks. CEREZYME® is administered by IV infusion.

Abraxane, paclitaxel-conjugated albumin, is approved for metastatic breast cancer, non-small cell lung cancer, and late stage pancreatic cancer.

Taliglucerase alfa (ELEYSO®) is a hydrolytic lysosomal glucocerebroside-specific enzyme indicated for long-term enzyme replacement therapy for Type 1 Gaucher disease. The recommended dose is 60 U/kg of body weight administered once every 2 weeks via intravenous infusion.

Laronidase (ALDURAZYME®) is a polymorphic variant of the human enzyme α-L-iduronidase that is produced via CHO cell line. The recommended dosage regimen of ALDURAZYME® is 0.58 mg/kg administered once weekly as an intravenous infusion.

Elosufase alfa (VIMIZIM®) is a human N-acetylgalactosamine-6-sulfatase produced by CHO cell line by BioMarin Pharmaceuticals Inc ("BioMarin"). It was approved by the FDA on Feb. 14, 2014 for the treatment of Mucopolysaccharidosis Type IVA. It is administered weekly via intravenous infusion at a dosage of 2 mg/kg.

Other biologics which may be formulated with viscosity-lowering agents include asparaginase *Erwinia chrysanthemi* (ERWINAZE®), incobotulinumtoxin A (XEOMIN®), EPOGEN® (epoetin Alfa), PROCRIT® (epoetin Alfa), ARANESP® (darbepoetin alfa), ORENCIA® (abatacept), BATASERON® (interferon beta-1b), NAGLAZYME® (galsulfase); ELAPRASE® (Idursulfase); MYOZYME® (LUMIZYME®, alguosidase alfa); VPRIV® (velaglucerase), abobotulinumtoxin A (DYSPORT®); BAX-326, Octocog alfa from Baxter; Syncria from GlaxoSmithKline; liprotamase from Eli Lilly; Xiaflex (collagenase *clostridium histolyticum*) from Auxilium and BioSpecifics Technologies Corp.; anakinra from Swedish Orphan Biovitrum AB; metreleptin from Bristol-Myers Squibb; Avonex, Plegridy (BIIB017) from Biogen; NN1841, NN7008 from Novo Nordisk; KRN321 (darbepoetin alfa), AMG531 (romiplostim), KRN125 (pegfilgrastim), KW-0761 (mogamulizumab) from Kyowa; IB1001 from Inspiration Biopharmaceuticals; Iprivask from Canyon Pharmaceuticals Group.

Protein Therapeutics in Development

Versartis, Inc.'s VRS-317 is a recombinant human growth hormone (hGH) fusion protein utilizing the XTEN half-life extension technology. It aims to reduce the frequency of hGH injections necessary for patients with hGH deficiency. VRS-317 has completed a Phase II study, comparing its efficacy to daily injections of non-derivatized hGH, with positive results. Phase III studies are planned.

Vibriolysin is a proteolytic enzyme secreted by the Gram-negative marine microorganism, *Vibrio proteolyticus*. This endoprotease has specific affinity for the hydrophobic regions of proteins and is capable of cleaving proteins adjacent to hydrophobic amino acids. Vibriolysin is currently being investigated by Biomarin for the cleaning and/or treatment of burns. Vibriolysin formulations are described in patent WO 02/092014.

PEG-PAL (PEGylated recombinant phenylalanine ammonia lyase or "PAL") is an investigational enzyme substitution therapy for the treatment of phenylketonuria (PKU), an inherited metabolic disease caused by a deficiency of the enzyme phenylalanine hydroxylase (PAH). PEG-PAL is being developed as a potential treatment for patients whose blood phenylalanine (Phe) levels are not adequately controlled by KUVAN®. PEG-PAL is now in Phase 2 clinical development to treat patients who do not adequately respond to KUVAN®.

Other protein therapeutics which may be formulated with viscosity-lowering agents include Alprolix/rFIXFc, Eloctate/rFVIIIFc, BMN-190; BMN-250; Lamazyme; Galazyme; ZA-011; Sebelipase alfa; SBC-103; and HGT-1110. Additionally, fusion-proteins containing the XTEN half-life extension technology including, but not limited to: VRS-317 GH-XTEN; Factor VIIa, Factor VIII, Factor IX; PF05280602, VRS-859; Exenatide-XTEN; AMX-256; GLP2-2G/XTEN; and AMX-179 Folate-XTEN-DM1 can be formulated with viscosity-lowering agents.

Other late-stage protein therapeutics which can be formulated with viscosity-lowering agents include CM-AT from CureMark LLC; NN7999, NN7088, Liraglutide (NN8022), NN9211, Semaglutide (NN9535) from Novo Nordisk; AMG 386, Filgrastim from Amgen; CSL-654, Factor VIII from CSL Behring; LA-EP2006 (pegfilgrastim biosimilar) from Novartis AG; Multikine (leukocyte interleukin) from CEL-SCI Corporation; LY2605541, Teriparatide (recombinant PTH 1-34) from Eli Lilly; NU-100 from Nuron Biotech, Inc.; Calaspargase Pegol from Sigma-Tau Pharmaceuticals, Inc.; ADI-PEG-20 from Polaris Pharmaceuticals, Inc.; BMN-110, BMN-702 from BioMarin; NGR-TNF from Molmed S.p.A.; recombinant human C1 esterase inhibitor from Pharming Group/Santarus Inc.; Somatropin biosimilar from LG Life Sciences LTD; Natpara from NPS Pharmaceuticals, Inc.; ART123 from Asahi Kasei Corporation; BAX-111 from Baxter; OBI-1 from Inspiration Biopharmaceuticals; Wilate from Octapharma AG; Talactoferrin alfa from Agennix AG; Desmoteplase from Lundbeck; Cinryze from Shire; RG7421 and Roche and Exelixis, Inc.; Midostaurin (PKC412) from Novartis AG; Damoctocog alfa pegol, BAY 86-6150, BAY 94-9027 from Bayer AG; Peginterferon lambda-1a, Nulojix (Belatacept) from Bristol-Myers Squibb; Pergoveris, Corifollitropin alfa (MK-8962) from Merck KGaA; recombinant coagulation Factor IX Fc fusion protein (rFIXFc; BIIB029) and recombinant coagulation Factor VIII Fc fusion protein (rFVIIIFc; BIIB031) from Biogen; and Myalept from AstraZeneca.

Other early stage protein biologics which can be formulated with viscosity-lowering agents include Alferon LDO from Hemispherx BioPharma, Inc.; SL-401 from Stemline Therapeutics, Inc.; PRX-102 from Protalix Biotherapeutics, Inc.; KTP-001 from Kaketsuken/Teijin Pharma Limited; Vericiguat from Bayer AG; BMN-111 from BioMarin; ACC-001 (PF-05236806) from Janssen; LY2510924, LY2944876 from Eli Lilly; NN9924 from Novo Nordisk; INGAP peptide from Exsulin; ABT-122 from Abbvie; AZD9412 from AstraZeneca; NEUBLASTIN (BG00010) from Biogen; Luspatercept (ACE-536), Sotatercept (ACE-011) from Celgene Corporation; PRAME immunotherapeutic from GlaxoSmithKline; Plovamer acetate (PI-2301) from Merck KGaA; PREMIPLEX (607) from Shire; BMN-701 from BioMarin; Ontak from Eisai; rHuPH20/insulin from Halozyme, Inc.; PB-1023 from PhaseBio Pharmaceuticals, Inc.; ALV-003 from Alvine Pharmaceuticals Inc. and Abbvie; NN8717 from Novo Nordisk; PRT-201 from Proteon Therapeutics Inc.; PEGPH20 from Halozyme, Inc.; Amevive® alefacept from Astellas Pharma Inc.; F-627 from Regeneron; AGN-214868 (senrebotase) from Allergan, Inc.; BAX-817 from Baxter; PRT4445 from Portola Pharmaceuticals, Inc.; VEN100 from Ventria Bioscience; Onconase/ranpimase from Tamir Biotechnology Inc.; interferon alpha-2b infusion from Medtronic, Inc; sebelipase alfa from Synageva BioPharma; IRX-2 from IRX Therapeutics, Inc; GSK2586881 from GlaxoSmithKline; SI-6603 from Seikagaku Corporation; ALXN1101, asfotase alfa from Alexion; SHP611, SHP609 (Elaprase, idursulfase) from Shire; PF-04856884, PF-05280602 from Pfizer; ACE-031, Dalantercept from Acceleron Pharma; ALT-801 from Altor BioScience Corp.; BA-210 from BioAxone Biosciences, Inc.; WT1 immunotherapeutic from GlaxoSmithKline; GZ402666 from Sanofi; MSB0010445, Atacicept from Merck KGaA; Leukine (sargramostim) from Bayer AG; KUR-211 from Baxter; fibroblast growth factor-1 from CardioVascular BioTherapeutics Inc.; SPI-2012 from Hanmi Pharmaceuticals Co., LTD/Spectrum Pharmaceuticals; FGF-18 (sprifermin) from Merck KGaA; MK-1293 from Merck; interferon-alpha-2b from HanAll Biopharma; CYT107 from Cytheris SA; RT001 from Revance Therapeutics, Inc.; MEDI6012 from AztraZeneca; E2609 from Biogen; BMN-190, BMN-270 from BioMarin; ACE-661 from Acceleron Pharma; AMG 876 from Amgen; GSK3052230 from GlaxoSmithKline; RG7813 from Roche; SAR342434, Lantus from Sanofi; AZO1 from Allozyne Inc.; ARX424 from Ambrx, Inc.; FP-1040, FP-1039 from FivePrime Therapeutics, Inc.; ATX-MS-1467 from Merck KGaA; XTEN fusion proteins from Amunix Operating Inc.; entolimod (CBLB502) from Cleveland BioLabs, Inc.; HGT2310 from Shire; HM10760A from Hanmi Pharmaceuticals Co., LTD; ALXN1102/ALXN1103 from Alexion; CSL-689, CSL-627 from CSL Behring; glial growth factor 2 from Acorda Therapeutics, Inc.; NX001 from Nephrx Corporation; NN8640, NN1436, NN1953, NN9926, NN9927, NN9928 from Novo Nordisk; NHS-IL 12 from EMD Serono; 3K3A-APC from ZZ Biotech LLC; PB-1046 from PhaseBio Pharmaceuticals, Inc.; RU-101 from R-Tech Ueno, Ltd.; insulin lispro/BC106 from Adocia; hl-con1 from Iconic Therapeutics, Inc.; PRT-105 from Protalix BioTherapeutics, Inc.; PF-04856883, CVX-096 from Pfizer; ACP-501 from AlphaCore Pharma LLC; BAX-855 from Baxter; CDX-1135 from Celldex Therapeutics; PRM-151 from Promedior, Inc.; TS01 from Thrombolytic Science International; TT-173 from Thrombotargets Corp.; QBI-139 from Quintessence Biosciences, Inc.; Vatelizumab, GBR500, GBR600, GBR830, and GBR900 from Glenmark Pharmaceuticals; and CYT-6091 from Cytimmune Sciences, Inc.

Other Biologic Agents

Other biologic drugs that can be formulated with viscosity-lowering agents include PF-05285401, PF-05231023, RN317 (PF-05335810), PF-06263507, PF-05230907, Dekavil, PF-06342674, PF06252616, RG7598, RG7842, RG7624d, OMP54F28, GSK1995057, BAY1179470, IMC-3G3, IMC-18F1, IMC-35C, IMC-20D7S, PF-06480605, PF-06647263, PF-06650808, PF-05335810 (RN317) PD-0360324, PF-00547659 from Pfizer; MK-8237 from Merck; BI033 from Biogen; GZ402665, SAR438584/REGN2222 from Sanofi; IMC-18F1; and Icrucumab, IMC-3G3 from ImClone LLC; Ryzodeg, Tresiba, Xultophy from Novo Nordisk; Toujeo (U300), LixiLan, Lyxumia (lixisenatide) from Sanofi; MAGE-A3 immunotherapeutic from GlaxoSmithKline; Tecemotide from Merck KGaA; Sereleaxin (RLX030) from Novartis AG; Erythropoietin; Pegfilgrastim; LY2963016, Dulaglutide (LY2182965) from Eli Lilly; and Insulin Glargine from Boehringer Ingelheim.

B. Viscosity-Lowering Agents

The viscosity of liquid protein formulations, including low-molecular-weight and/or high-molecular-weight proteins, is reduced by the addition of one or more viscosity-lowering agents. The pharmaceutical formulations may be converted from non-Newtonian to Newtonian fluids by the addition of an effective amount of one or more viscosity-lowering agents.

When employed in a formulation intended for administration to a human or other mammal, the viscosity-lowering agents, like the formulation itself, must be pharmaceutically acceptable. The viscosity-lowering agents are typically organic compounds containing at least one non-carbon, non-hydrogen atom. Preferably, the viscosity-lowering agents contain hydrogen, carbon, oxygen and at least one other type of atom. In certain embodiments, the viscosity-lowering agents are characterized by at least one of the following:

1) organic compounds having at least four carbon and four hydrogen atoms, and at least one sulfur, oxygen, nitrogen, or phosphorus atom;
2) a molecular weight between about 85 and 1,000 Da;
3) the presence of at least one charged, or other hydrophilic, moiety;
4) the presence of at least one, preferably two, and more preferably three, freely rotating bonds;
5) the presence of at least one substituted ring;
6) a molecular polar surface area of at least 24 Å$^2$, preferably at least 50 Å$^2$, and more preferably at least 80 Å$^2$;
7) a molar volume of at least 75 cm$^3$, preferably at least 85 cm$^3$, more preferably at least 100 cm$^3$, and most preferably at least 120 cm$^3$;
8) a polarizability of at least 10 cm$^3$, preferably at least 15 cm$^3$, more preferably at least 20 cm$^3$, and most preferably at least 25 cm$^3$; and
9) the presence of at least one, preferably two, and more preferably three hydrogen bond donors and/or acceptors.

In certain embodiments, the viscosity-lowering agent is characterized by at least two, three, four, five, six, seven, eight or all nine of the above listed attributes. In certain embodiments, the viscosity-lowering agent is further characterized in that it does not contain an aldehyde or carbon-carbon triple bond functional group.

In other embodiments, the viscosity-lowering agent is a combination of two or more compounds, each of which is characterized by at least two, three, four, five, six, seven, eight or all nine of the above listed attributes.

In some embodiments, the viscosity-lowering agents are listed as GRAS by the U.S. Food and Drug Administration ("the FDA"), as of Sep. 11, 2014. "GRAS" is an acronym for the phrase Generally Recognized As Safe. Under sections 201(s) and 409 of the Federal Food, Drug, and Cosmetic Act (the Act), any substance that is intentionally added to food is a food additive and is subject to premarket review and approval by FDA unless the substance is generally recognized, among qualified experts, as having been adequately shown to be safe under the conditions of its intended use, or unless the use of the substance is otherwise excluded from the definition of a food additive. Another source of compounds is the Inactive Ingredient Guide of the FDA (IIG), and equivalents listed by the International Pharmaceutical Excipients Council (IPEC) and the European Medicines Agency (EMA), as of Sep. 11, 2014. The substances used in formulations must be safe for injection. Preferably, the GRAS-listed viscosity-lowering agent is characterized by at least two, three, four, five, six, seven, eight or all nine of the above listed attributes.

In other embodiments, the viscosity-lowering agent is an FDA- or EMA-approved drug product as of Sep. 11, 2014. Like compounds drawn from the GRAS and IIG lists, the toxicity and safety profiles of FDA- and EMA-approved drug products are well established. In addition to lowering the viscosity of the protein solution, the use of an FDA- or EMA-approved drug product provides the opportunity for combination therapies. Preferably a FDA- or EMA-approved drug product viscosity-lowering agent is characterized by at least two, three, four, five, six, seven, eight or all nine of the above listed attributes.

In some embodiments, the viscosity-lowering agent includes at least one compound of Formula (I):

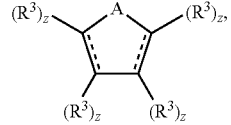

Formula (1)

or a pharmaceutically acceptable salt thereof;
wherein

represents either a single or double bond, A is a selected from O, S, SO$_2$, NR$^3$, C(R$^3$)$_2$ or:

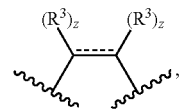

wherein R$^3$ is independently selected from hydrogen, R$^2$, —OH, NH$_2$, —F, —Cl, —Br, —I, —NO$_2$, —CN, —C(=O)R$^{4a}$, —C(=NR$^{4a}$)R$^4$, —C(=O)OH, —C(=O)OR$^4$, —OC(=O)R$^4$, —OC(=O)OR$^4$, —SO$_3$H, —SO$_2$N(R$^{4a}$)$_2$, —SO$_2$R$^4$, —SO$_2$NR$^{4a}$C(=O)R$^4$, —PO$_3$H$_2$, —R$^{4a}$C(=NR$^{4a}$)N(R$^{4a}$)$_2$, —NHC(=NR$^{4a}$)NH—CN, —NR$^{4a}$C(=O)R$^4$, —NR$^{4a}$SO$_2$R$^4$, —NR$^{4a}$C(=NR$^{4a}$)NR$^{4a}$C(=NR$^{4a}$)N(R$^{4a}$)$_2$, —NR$^{4a}$C(=O)N(R$^{4a}$)$_2$, —C(=O)NH$_2$, —C(=O)N(R$^{4a}$)$_2$, —OR$^4$, —SR$^{4a}$, and —N(R$^{4a}$)$_2$;

wherein R$^2$ is independently selected from C$_{1-12}$alkyl, C$_{3-12}$cycloalkyl, C$_{6-12}$aryl, C$_{1-12}$heteroaryl and C$_{2-12}$heterocyclyl;

wherein each C$_{1-12}$alkyl may be substituted one or more times with C$_{3-12}$cycloalkyl, C$_{6-12}$aryl, C$_{1-12}$heteroaryl, C$_{2-12}$heterocyclyl, —OH, NH$_2$, (=O), (=NR$^{4a}$), —F, —Cl, —Br, —I, —NO$_2$, —CN, —C(=O)R$^{4a}$, —C(=NR$^{4a}$)R$^4$, —C(=O)OH, —C(=O)OR$^4$, —OC(=O)R$^4$, —OC(=O)OR$^4$, —SO$_3$H, —SO$_2$N(R$^{4a}$)$_2$, —SO$_2$R$^4$, —SO$_2$NR$^{4a}$C(=O)R$^4$, —PO$_3$H$_2$, —R$^{4a}$C(=NR$^{4a}$)N(R$^{4a}$)$_2$, —NHC(=NR$^{4a}$)NH—CN, —NR$^{4a}$C(=O)R$^4$, —NR$^{4a}$SO$_2$R$^4$, —NR$^{4a}$C(=NR$^{4a}$)NR$^{4a}$C(=NR$^{4a}$)N(R$^{4a}$)$_2$, —NR$^{4a}$C(=O)N(R$^{4a}$)$_2$, —C(=O)NH$_2$, —C(=O)N(R$^{4a}$)$_2$, —SR$^{4a}$, or —N(R$^{4a}$)$_2$;

wherein each C$_{3-12}$cycloalkyl may be substituted one or more times with C$_{1-12}$alkyl, C$_{6-12}$aryl, C$_{1-12}$heteroaryl, $C_{2-12}$heterocyclyl, —OH, $NH_2$, —F, —Cl, —Br, —I, —$NO_2$, —CN, —C(=O)$R^{4a}$, —C(=$NR^{4a}$)$R^4$, —C(=O)OH, —C(=O)O$R^4$, —OC(=O)$R^4$, —OC(=O)O$R^4$, —$SO_3H$, —$SO_2N(R^{4a})_2$, —$SO_2R^4$, —$SO_2NR^{4a}$C(=O)$R^4$, —$PO_3H_2$, —$R^{4a}$C(=$NR^{4a}$)N($R^{4a}$)$_2$, —NHC(=$NR^{4a}$)NH—CN, —$NR^{4a}$C(=O)$R^4$, —$NR^{4a}SO_2R^4$, —$NR^{4a}$C(=$NR^{4a}$)$NR^{4a}$C(=$NR^{4a}$)N($R^{4a}$)$_2$, —$NR^{4a}$C(=O)N($R^{4a}$)$_2$, —C(=O)$NH_2$, —C(=O)N($R^{4a}$)$_2$, —S$R^{4a}$, or —N($R^{4a}$)$_2$;

wherein each $C_{6-12}$aryl may be substituted one or more times with $C_{1-12}$alkyl, $C_{3-12}$cycloalkyl, $C_{1-12}$heteroaryl, $C_{2-12}$heterocyclyl, —OH, $NH_2$, —F, —Cl, —Br, —I, —$NO_2$, —CN, —C(=O)$R^{4a}$, —C(=$NR^{4a}$)$R^4$, —C(=O)OH, —C(=O)O$R^4$, —OC(=O)$R^4$, —OC(=O)O$R^4$, —$SO_3H$, —$SO_2N(R^{4a})_2$, —$SO_2R^4$, —$SO_2NR^{4a}$C(=O)$R^4$, —$PO_3H_2$, —$R^{4a}$C(=$NR^{4a}$)N($R^{4a}$)$_2$, —NHC(=$NR^{4a}$)NH—CN, —$NR^{4a}$C(=O)$R^4$, —$NR^{4a}SO_2R^4$, —$NR^{4a}$C(=$NR^{4a}$)$NR^{4a}$C(=$NR^{4a}$)N($R^{4a}$)$_2$, —$NR^{4a}$C(=O)N($R^{4a}$)$_2$, —C(=O)$NH_2$, —C(=O)N($R^{4a}$)$_2$, —S$R^{4a}$, or —N($R^{4a}$)$_2$;

wherein each $C_{1-12}$heteroaryl may be substituted one or more times with $C_{1-12}$alkyl, $C_3$-12cycloalkyl, $C_{6-12}$aryl, $C_{2-12}$heterocyclyl, —OH, $NH_2$, —F, —Cl, —Br, —I, —$NO_2$, —CN, —C(=O)$R^{4a}$, —C(=$NR^{4a}$)$R^4$, —C(=O)OH, —C(=O)O$R^4$, —OC(=O)$R^4$, —OC(=O)O$R^4$, —$SO_3H$, —$SO_2N(R^{4a})_2$, —$SO_2R^4$, —$SO_2NR^{4a}$C(=O)$R^4$, —$PO_3H_2$, —$R^{4a}$C(=$NR^{4a}$)N($R^{4a}$)$_2$, —NHC(=$NR^{4a}$)NH—CN, —$NR^{4a}$C(=O)$R^4$, —$NR^{4a}SO_2R^4$, —$NR^{4a}$C(=$NR^{4a}$)$NR^{4a}$C(=$NR^{4a}$)N($R^{4a}$)$_2$, —$NR^{4a}$C(=O)N($R^{4a}$)$_2$, —C(=O)$NH_2$, —C(=O)N($R^{4a}$)$_2$, —O$R^4$, —S$R^{4a}$, or —N($R^{4a}$)$_2$;

wherein each $C_{2-12}$heterocyclyl may be substituted one or more times with $C_{1-12}$alkyl, $C_{3-12}$cycloalkyl, $C_{6-12}$aryl, $C_{1-12}$heteroaryl, —OH, $NH_2$, —F, —Cl, —Br, —I, —$NO_2$, —CN, —C(=O)$R^{4a}$, —C(=$NR^{4a}$)$R^4$, —C(=O)OH, —C(=O)O$R^4$, —OC(=O)$R^4$, —OC(=O)O$R^4$, —$SO_3H$, —$SO_2N(R^{4a})_2$, —$SO_2R^4$, —$SO_2NR^{4a}$C(=O)$R^4$, —$PO_3H_2$, —$R^{4a}$C(=$NR^{4a}$)N($R^{4a}$)$_2$, —NHC(=$NR^{4a}$)NH—CN, —$NR^{4a}$C(=O)$R^4$, —$NR^{4a}SO_2R^4$, —$NR^{4a}$C(=$NR^{4a}$)$NR^{4a}$C(=$NR^{4a}$)N($R^{4a}$)$_2$, —$NR^{4a}$C(=O)N($R^{4a}$)$_2$, —C(=O)$NH_2$, —C(=O)N($R^{4a}$)$_2$, —O$R^4$, —S$R^{4a}$, or —N($R^{4a}$)$_2$;

wherein $R^4$ is independently selected from $C_{1-12}$alkyl, $C_{3-12}$cycloalkyl, $C_{6-12}$aryl, $C_{1-12}$heteroaryl and $C_{2-12}$heterocyclyl, each of which may be substituted one or more times by —OH, —$NH_2$, —F, —Cl, —Br, —I, —$NO_2$, —CN, —C(=O)OH, —$SO_3H$, —$PO_3H_2$, or —C(=O)$NH_2$;

wherein $R^{4a}$ may be $R^4$ or hydrogen;

wherein any two or more of $R^2$, $R^3$, $R^4$ and $R^{4a}$ groups may together form a ring;

wherein when two $R^3$ groups are bonded to the same carbon atom, the two $R^3$ groups may together form an (=O), (=$NR^{4a}$), or (=C($R^{4a}$)$_2$);

wherein z is in each case independently selected from 1 or 2, provided that when the ($R^3$)$_z$ substituent is connected to an sp$^2$ hybridized carbon, z is 1, and when the ($R^3$)$_z$ substituent is connected to an sp$^3$ hybridized carbon, z is 2.

When the substituent —$NR^{4a}$C(=$NR^{4a}$)$NR^{4a}$C(=$NR^{4a}$)N($R^{4a}$)$_2$ is present, it is preferred that $R^{4a}$ is selected so as to give —NHC(=NH)NHC(=NH)$NH_2$.

In certain embodiments, the compound of Formula (1) contains at least one substituent selected from —C(=O)OH, —$SO_3H$, —$SO_2$NHC(=O)$R^4$, and —$PO_3H_2$. In some embodiments, the compound of Formula (1) contains at least one —$SO_3H$ group.

In certain embodiments, one or more of the $R^3$ substituents may be:

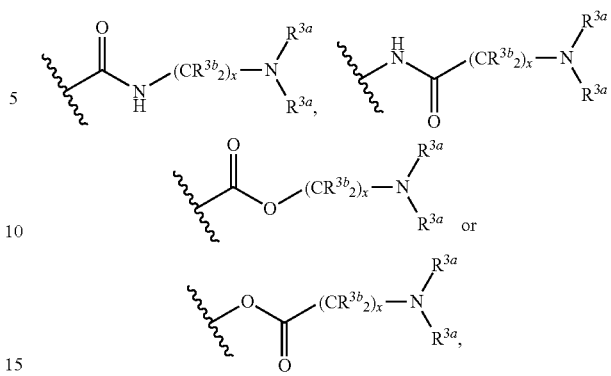

wherein $R^{3a}$ and $R^{3b}$ are independently selected from hydrogen, $C_{1-12}$alkyl, $C_{3-12}$cycloalkyl, $C_{6-12}$aryl, $C_{1-12}$heteroaryl and $C_{2-12}$heterocyclyl, C(=O)$R^{4a}$, —C(=O)OH, —C(=O)O$R^4$, —$SO_3H$, —$SO_2N(R^{4a})_2$, —$SO_2R^4$, —$SO_2$NHC(=O)$R^4$, C(=O)$NH_2$, —C(=O)N($R^{4a}$)$_2$, —S$R^4$, and —N($R^{4a}$)$_2$, and when any two $R^{3b}$ are bonded to the same carbon atom, the two $R^{3b}$ groups may together form an (=O), (=$NR^{4a}$), or (=C($R^{4a}$)$_2$);

wherein each $C_{1-12}$alkyl, $C_{3-12}$cycloalkyl, $C_{6-12}$aryl, $C_{1-12}$heteroaryl and $C_2$-12heterocyclyl may be substituted one or more times with —OH, $NH_2$, —F, —Cl, —Br, —I, —$NO_2$, —CN, —C(=O)$R^{4a}$, —C(=$NR^{4a}$)$R^4$, —C(=O)OH, —C(=O)O$R^4$, —OC(=O)$R^4$, —OC(=O)O$R^4$, —$SO_3H$, —$SO_2N(R^{4a})_2$, —$SO_2R^4$, —$SO_2NR^{4a}$C(=O)$R^4$, —$PO_3H_2$, —$R^{4a}$C(=$NR^{4a}$)N($R^{4a}$)$_2$, —NHC(=$NR^{4a}$)NH—CN, —$NR^{4a}$C(=O)$R^4$, —$NR^{4a}SO_2R^4$, —$NR^{4a}$C(=$NR^{4a}$)$NR^{4a}$C(=$NR^{4a}$)N($R^{4a}$)$_2$, —$NR^{4a}$C(=O)N($R^{4a}$)$_2$, —C(=O)$NH_2$, —C(=O)N($R^{4a}$)$_2$, —O$R^4$, —S$R^{4a}$, or —N($R^{4a}$)$_2$;

wherein $R^4$ and $R^{4a}$ are as defined above;

wherein x is selected from 1, 2, 3, 4, 5, 7, 8, 9 or 10; and wherein any two or more of $R^3$, $R^{3a}$, $R^4$ and $R^{4a}$ groups may together form a ring.

In certain embodiments, the compound of Formula (1) may be represented by either the compound of Formula (1a) or (1b):

Formula (1a)

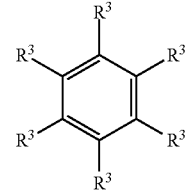

Formula (1b)

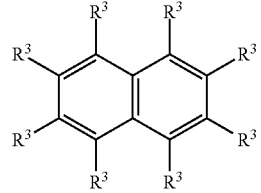

wherein $R^3$ has the meanings given above.

In certain embodiments, the compound of Formula (1a) may be represented by the compounds of Formulas (1a-i-iv):

Formula (1a-i)

[Chemical structure: benzamide with R³ substituents, -NH-(CR³ᵇ₂)ₓ-N(R³ᵃ)₂]

Formula (1a-ii)

[Chemical structure: benzoate ester with R³ substituents, -O-(CR³ᵇ₂)ₓ-N(R³ᵃ)₂]

Formula (1a-iii)

[Chemical structure: anilide with R³ substituents, -NH-C(=O)-(CR³ᵇ₂)ₓ-N(R³ᵃ)₂]

Formula (1a-iv)

[Chemical structure: aryl carbonate/ester with R³ substituents, -O-C(=O)-(CR³ᵇ₂)ₓ-N(R³ᵃ)₂]

wherein R³ is independently selected from hydrogen, NH₂, CH₃, Cl, OR⁴ and NHR⁴;

wherein x is 1 or 2;

wherein R³ᵃ and R³ᵇ are independently selected from hydrogen and C₁₋₁₂ alkyl;

wherein said C₁₋₁₂alkyl may be substituted one or more times by C₃₋₁₂cycloalkyl, C₆₋₁₂aryl, C₁₋₁₂heteroaryl, C₂₋₁₂heterocyclyl, —OH, NH₂, —F, —Cl, —Br, —I, —NO₂, —CN, —C(=O)R⁴ᵃ, —C(=NR⁴ᵃ)R⁴, —C(=O) OH, —C(=O)OR⁴, —OC(=O)R⁴, —OC(=O)OR⁴, —SO₃H, —SO₂N(R⁴ᵃ)₂, —SO₂R⁴, —SO₂NR⁴ᵃC(=O)R⁴, —PO₃H₂, —R⁴ᵃC(=NR⁴ᵃ)N(R⁴ᵃ)₂, —NHC(=NR⁴ᵃ) NH—CN, —NR⁴ᵃC(=O)R⁴, —NR⁴ᵃSO₂R⁴, —NR⁴ᵃC (=NR⁴ᵃ)NR⁴ᵃC(=NR⁴ᵃ)N(R⁴ᵃ)₂, —NR⁴ᵃC(=O)N(R⁴ᵃ)₂, —C(=O)NH₂, —C(=O)N(R⁴ᵃ)₂, —OR⁴, —SR⁴ᵃ, or —N(R⁴ᵃ)₂;

R⁴ and R⁴ᵃ are as defined above; and wherein any two or more R³ᵃ, R³ᵇ, R⁴, R⁴ᵃ may together form a ring.

The compound of Formula (1) may be represented by the compound of Formula (1a-v, vi or vii):

(1a-v)

[Chemical structure: benzene ring with R³ and R³ᶠ substituents]

(1a-vi)

[Chemical structure: naphthalene with R³ and R³ᶠ substituents]

(vii)

[Chemical structure: naphthalene with R³ and R³ᶠ substituents]

wherein R³ᶠ is selected from —C(=O)OH, —SO₃H, —SO₂NHC(=O)R⁴, and —PO₃H₂, and R³ is as defined above. In certain preferred embodiments, R³ is independently selected from hydrogen, OH, NH₂, C₁₋₆alkyl and COOH.

In other embodiments, the compound of Formula (1) may be represented by any of the compounds of Formulae (1c), (1d), (1e) or (1f):

Formula (1c)

[Chemical structure: bicyclic cage with R³ substituents]

Formula (1d)

[Chemical structure: cyclohexane with R³ substituents]

Formula (1e)

[Chemical structure: cyclopentane with R³ substituents]

Formula (1f)

[Chemical structure: polycyclic cage with R³ substituents]

wherein R³ has the meanings given above.

In other embodiments, the compound of Formula (1) may be represented by a compound of Formula (1g):

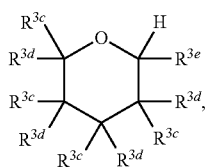

Formula (1g)

wherein $R^{3c}$ is independently selected from hydrogen and $R^2$, wherein $R^2$ has the meanings given above;

wherein $R^{3d}$ is independently selected from hydrogen, OH, $NH_2$, $NH(C_{1-6}alkyl)$, $N(C_{1-6}alkyl)_2$; $NHC(=O)$ $(C_{1-6}alkyl)$, COOH and $CH_2OH$;

or any two $R^{3c}$ and $R^{3d}$ groups connected to the same carbon may together form an oxo (=O), imino (=$NR^{4a}$), or an olefin (=$C(R^{4a})_2$), wherein $R^{4a}$ has the meanings given above;

wherein $R^{3e}$ is selected from hydrogen, —OH or $OR^4$; and wherein $R^4$ has the meanings given above.

In certain embodiments, the viscosity-lowering agent includes a compound of Formula (1g-i):

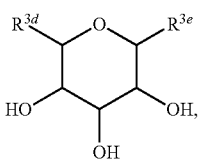

Formula (1g-i)

wherein $R^{3e}$ is selected from OH and —$OC_{1-12}$alkyl, which is further substituted with at least one OH and at least one COOH; and wherein $R^{3d}$ is selected from COOH and $CH_2OH$.

In some embodiments, the viscosity-lowering agent includes a compound of Formula (2):

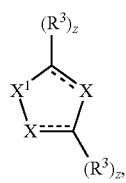

Formula (2)

or a pharmaceutically acceptable salt thereof;
wherein

⫶ represents a single or double bond;

X is independently selected from chalcogen, $N(R^3)_z$ and $C(R^3)_z$;

$X^1$ is absent, or is chalcogen, $N(R^3)_z$, $C(R^3)_z$ or:

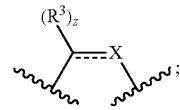

wherein $R^3$ has the meanings given for the compound of Formula (1);

provided that when the $(R^3)_z$ substituent is connected to an $sp^2$ hybridized nitrogen, z is 0 or 1, when the $(R^3)_z$ substituent is connected to an $sp^2$ hybridized carbon or an $sp^3$ hybridized nitrogen, z is 1, and when the $(R^3)_z$ substituent is connected to an $sp^3$ hybridized carbon, z is 2;

wherein at least one of X or $X^1$ is chalcogen or $N(R^3)_z$.

In certain embodiments, the compound may be an aromatic ring. Exemplary aromatic rings include the compounds of Formulas (2a-e):

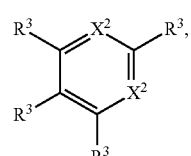

Formula (2a)

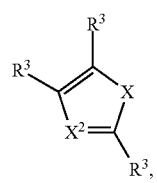

Formula (2b)

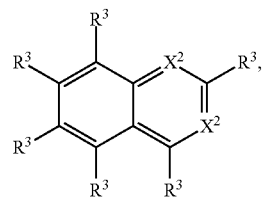

Formula (2c)

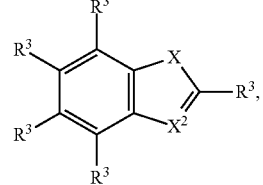

Formula (2d)

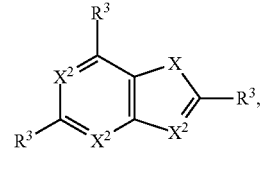

Formula (2e)

wherein $R^3$ and X have the meanings above, and $X^2$ is selected from $N(R^3)_z$ and $C(R^3)_z$.

In certain embodiments, the viscosity-lowering agent is a compound of Formula (2a-i):

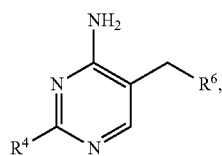
(Formula 2a-i)

wherein $R^4$ is as defined above and is preferably hydrogen or $CH_3$;

wherein $R^6$ is $C_{1-12}$heteroaryl, which may be substituted one or more times by $C_{1-6}$alkyl;

wherein said $C_{1-6}$alkyl may be substituted one or more times by OH, —$NH_2$, —F, —Cl, —Br, —I, —$NO_2$, —CN, —C(=O)$R^4$, —C(=$NR^{4a}$)$R^4$, —C(=O)OH, —C(=O)O$R^4$, —$SO_3H$, —$SO_2NR^4$—, —$SO_2R_4$, —$PO_3H_2$, —NHC(=O)$R^4$, —NHC(=O)N($R^4$)$_2$, —C(=O)$NH_2$, —C(=O)N($R^4$)$_2$, —$OR^{4b}$, —$SR^{4b}$, —N($R^{4b}$)$_2$, wherein $R^4$ has the meanings given above; or

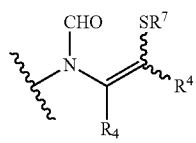

wherein $R^4$ is as defined above, and $R^7$ is selected from $SR^4$ and —C(=O)$R^4$. The double bond in the group above may be in either the E or Z geometry.

In preferred embodiments, $R^6$ is a heterocycle having the structure:

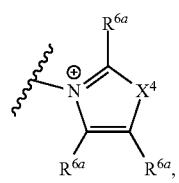

wherein $X^4$ is a chalcogen and $R^{6a}$ is hydrogen or $C_{1-6}$alkyl, wherein the $C_{1-6}$alkyl may be substituted one or more times by —OH, —$NH_2$, —F, —Cl, —Br, —I, —$NO_2$, —CN, —C(=O)OH. In an even more preferred embodiment, $R^6$ is a heterocycle having the structure:

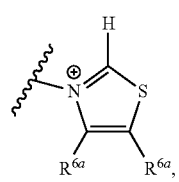

wherein $R^{6a}$ is selected from unsubstituted $C_{1-6}$alkyl and $C_{1-6}$alkyl substituted one or more times with —OH.

The viscosity-lowering agent may be an imidazole of Formula (2b-i)

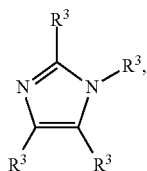
Formula (2b-i)

wherein $R^3$ is as defined above. In certain embodiments, $R^3$ is independently selected from hydrogen, $NO_2$, and $R^4$. In certain preferred embodiments, the compound of Formula (2b-i) has the structure:

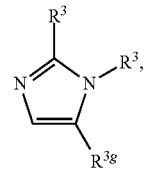

wherein $R^3$ is independently selected from $C_{1-6}$ alkyl, which may be unsubstituted or substituted one or more times with a group selected from OH, $NH_2$, $SR^4$, F, Cl, Br and I; and $R^{3g}$ is either hydrogen or $NO_2$.

In other embodiments, the viscosity-lowering agent has the structure of Formula (2a-ii) or Formula (2c-i):

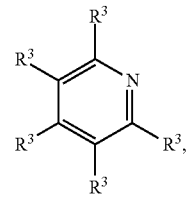
Formula (2a-ii)

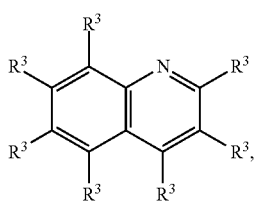
Formula (2c-i)

wherein $R^3$ is independently selected from OH, Cl, Br, F, I, N($R^{4a}$)$_2$, C(=O)OH, C(=O)$NH_2$.

In further embodiments, at least one $R^3$ substituent is $NHR^4$, wherein $R^4$ is a $C_{1-6}$alkyl, optionally substituted by one or more groups selected from Cl, Br, F, I, OH, C(=O)OH, $NH_2$, NH($C_{1-6}$alkyl) and N($C_{1-6}$alkyl)$_2$.

In other embodiments, the viscosity-lowering agent is a pyridinium salt of Formula (2a-iii):

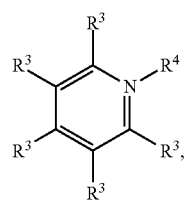

wherein $R^3$ and $R^4$ are as defined above.

In other embodiments, the heterocyclic ring is not a heteroaryl ring. Exemplary non-aromatic rings include the compounds of Formulas (2f-k):

Formula (2f)
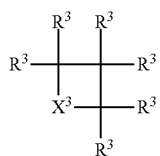

Formula (2g)
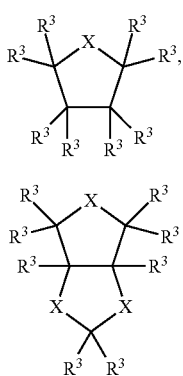

Formula (2h)

Formula (2i)
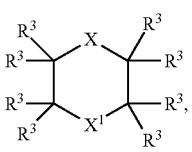

Formula (2j)
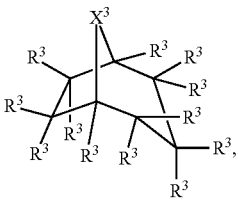

Formula (2k)
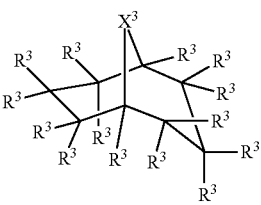

wherein $R^5$ and X have the meanings above, and $X^3$ is chalcogen or $N(R^3)_z$.

In certain embodiments, the compound of Formula (20 is a beta-lactam of Formula (2f-i), Formula (2f-i)
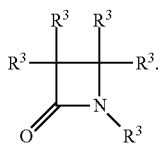

The beta lactam of Formula (2f-i) includes penicillin-type compounds, as well cephalosporin-type and cephamycin-type compounds of the Formula (2f-ii) and (2f-iii):

Formula (2f-ii)
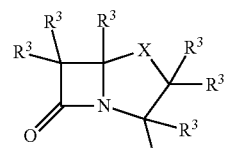

Formula (2f-iii)
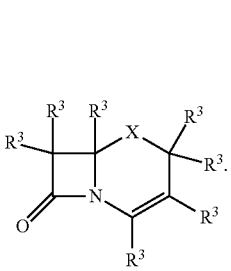

wherein X and $R_3$ are as defined above. In preferred embodiments, X is sulfur.

In certain embodiments, the compound of Formula (2i) is a compound of Formula (2i-i):

Formula (2i-i)
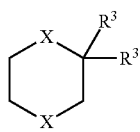

wherein X and $R^3$ are as defined above. In certain embodiments, X is in both cases $NR^4$, wherein $R^4$ has the meanings given above, and $R^3$ is in both cases hydrogen.

In other embodiments, the compound of Formula (2) is represented by a compound of Formula (2i-ii):

Formula (2i-ii)
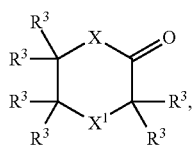

wherein X, $X^1$ and $R^3$ are as defined above.

The compound of Formula (2j) may be represented by the compound of Formula (2j-i):

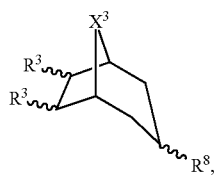

(Formula (2j-i))

wherein $X^3$ and $R^3$ are as defined above, and $R^8$ is selected from the NHC(=O)$R^2$ and OC(=O)$R^2$. In preferred embodiments, $X^3$ is $N^+(CH_3)_2$, $R^3$ are both hydrogen, or $R^3$ together form an epoxide or double bond.

The compound of Formula (2k) may be represented by the compound of Formula (2k-i):

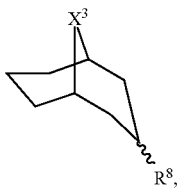

Formula (2k-i)

wherein $X^3$ and $R^8$ are as defined above.

In other embodiments, the viscosity-lowering agent includes a compound of the structure of Formula (3):

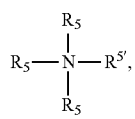

Formula (3)

or a pharmaceutically acceptable salt thereof;
wherein $R^5$ is in each case independently selected from hydrogen, and $R^2$,
$R^{5'}$ is either $R^5$ or absent;
providing that at least one $R^5$ substituent is not hydrogen, wherein $R^2$ has the same meanings given for the compound or Formula (1).

In certain embodiments, the viscosity-lowering agent is a mixture of two or more compounds selected from compounds of Formula (1), Formula (2) and Formula (3).

In preferred embodiments, the viscosity-lowering agent is camphorsulfonic acid (CSA), or a pharmaceutically acceptable salts thereof, such as an alkaline or alkaline earth metal salt. The camphorsulfonic acid or salt thereof is combined with one or more compounds of Formula (1), (2) or (3) to give mixtures such as CSA-piperazine, CSA-TRIS, CSA-4-amino pyridine, CSA-1-(o-tolyl)biguanide, CSA-procaine, CSA-Na-aminocyclohexane carboxylic acid, CSA-Na-creatinine and CSA-Na-ornidazole. Other preferred viscosity-lowering agents include thiamine, procaine, biotin, creatinine, metoclopramide, scopolamine, cimetidine, chloroquine phosphate, mepivacaine, graniseteron, sucralose, HEPES-tris, nicotinamide, lactobionic acid-TRIS, glucuronic acid-TRIS, sulfacetamide, CSA-4-aminopyridine, CSA-piperazine and cefazolin. Any two or more of the viscosity-lowering agents listed above may further be combined in the same formulation.

In other embodiments, the viscosity-lowering agent is an organosulfonic acid. Exemplary organosulfonic acids include, but are not limited to, camphorsulfonic acid, naphthalene-2-sulfonic acid, benzenesulfonic acid, toluenesulfonic acid, cyclohexylsuflonic acid, xylenesulfonic acids (including p-xylene-2-sulfonic acid, m-xylene-2-sulfonic acid, m-xylene-4-sulfonic acid and o-xylene-3-sulfonic acid), methanesulfonic acid, 1,2 ethane disulfonic acid, 4-(2-hydroxyethyl)-1-piperazine ethane sulfonic acid, 2-hydroxyethane-1-sulfonic acid, 3-hydroxypropane-1-sulfonic acid, cymenesulfonic acid, 4-hydroxybutane-1-sulfonic acid and pharmaceutically acceptable salts thereof. The organosulfonic acid may be in the form of an alkaline or alkaline earth metal salt, such as lithium, sodium, potassium, magnesium, and calcium salt. The organosulfonic acid (or salt thereof) may be combined with one or more compounds of Formula (2) or Formula (3).

In certain embodiments, the viscosity-lowering agent contains at least one carboxylic acid. The carboxylic acid may be in the form of an alkaline or alkaline earth metal salt, such as lithium, sodium, potassium, magnesium, and calcium salt. Exemplary carboxylic acid compounds include lactobionic acid, glucuronic acid, 1-aminocyclohexane carboxylic acid, biotin, brocrinat, cyclopentane propionic acid, hydroxynaphthoic acid, phenylpropionic acid, gentisic acid, salicylic acid, camphoric acid, mandelic acid, sulfosalicyclic acid, hydroxybenzoyl benzoic acid, phenyl acetic acid, acetyl salicylic acid, cinnamic acid, t-butyl acetic acid, phthalic acid, trimethylacetic acid, anthrallic acid and pharmaceutically acceptable salts thereof. The carboxylic acid (or salt thereof) may be combined with one or more compounds of Formula (2) or Formula (3).

The following compounds may also be used as viscosity-lowering agents: colistin, articaine, tetracaine, proxymetacaine, metoclopramide, procaine, lidocaine, cyclomethylcaine, piperocaine, chloroprocaine, etidocaine, benzocaine, phenylephrine, bupivacaine, mepivacaine, cinchocaine, mixtures thereof and and pharmaceutically acceptable salts thereof.

Other agents which may be employed as viscosity-lowering agents include 1-aminocyclohexane carboxylic acid, 1-(o-tolyl)biguanide, benzethonium chloride, benzoic acid, brocrinat, calcium carrageenan, calcium cyclamate, calcobutrol, caloxetic acid, camphorsulfonic acid, creatinine, dalfampridine, dehydroacetic acid, diazolidinyl urea, dichlorobenzyl alcohol, dimethyl isosorbide, epitetracycline, ethyl maltol, ethyl vanillin, ornidazole, gentisic acid ethanolamide, HEPES (4-(2-hydroxyethyl)-1-piperazine ethane sulfonic acid), gentisic acid, glucuronic acid, iodoxamic acid, menthol, galactose, medronic acid, m-cresol, glutathione, lactobionic acid, maltitol, octisalate, oxyquinoline, pentetic acid, piperazine, propenyl guaethol, propyl gallate, propylene carbonate, propylparaben, protamine sulfate, QUATERNIUM-15, QUATERNIUM-52, satialgine H, sodium 1,2-ethanedisulfonate, sodium cocoyl sarcosinate, sodium lauroyl sarcosinate, sodium polymetaphosphate, sodium pyrophosphate, pyroglutamic acid, sodium trimetaphosphate, sodium tripolyphosphate, sorbitan, tartaric acid, lactic acid, iofetamine, sucralose, 1-(4-pyridyl)pyridinium chloride, aminobenzoic acid, sulfacetamide sodium, naphthalene-2-sulfonic acid, tert-butylhydroquinone, thimerosal, trolamine, tromantadine, vanillin, versetamide, nioxime, niacinamide, methylisothiazolinone, mannose D, maltose, lidofenin, lactose, lactitol, isomalt, imidurea, gluconolactone, methanesulfonic acid, xylenesulfonic acid, sulfobutylether β-cyclodextrin and pharmaceutically acceptable salts thereof.

In certain embodiments, the viscosity-lowering agent includes an organic base. Exemplary organic bases include N-methylglucamine, morpholine, piperidine, and primary, secondary, tertiary, and quaternary amines, substituted amines, and cyclic amines. For example, they can be isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, lidocaine, hydrabamine, cholines, betaines, choline, betaine, ethylenediamine, theobromine, purines, piperazine, N-ethylpiperidine, N-methylpiperidine-polyamine. Particularly preferred organic bases are arginine, histidine, lysine, ethanolamine, thiamine, 2-amino-2-hydroxymethyl-propane-1,3-diol (TRIS), 4-aminopyridine, aminocyclohexane carboxylic acid, 1-o-tolybiguanide, ornidazole, urea, nictoinamide, benzethonium chloride, 5-amino-1-pentanol, 2-(2-aminoethoxy)ethanol, trans-cyclohexane-1,4-diamine, trans-cyclohexane-1R, 2R-diamine, ethylenediamine, propane-1,3-diamine, butane-1,4-diamine, pentane-1,5-diamine, hexane-1,6-diamine, octane-1,8-diamine, 5-amino-1-pentanol, 2-(2-aminoethoxy)ethanamine, 2-(2-(2-aminoethoxy)-ethoxy)ethanamine, 3-(4-(3-aminopropoxy)-butoxy)propan-1-amine, 3-(2-(3-aminopropoxy)-ethoxy)-ethoxy)propan-1-amine, N-(2-(2-aminoethylamino)ethyl)ethane-1,2-diamine, N-(2-aminoethyl)ethane-1,2-diamine, N-1-(2-(2-(2-aminoethylamino)ethylamino)-ethyl)ethane-1,2-diamine, N,N-dimethylhexane-1,6-diamine, N,N,N,N-tetramethylbutane-1,4-diamine, phenyltrimethylammonium salts, isopropylamine, diethylamine, ethanolamine, trimethamine, choline, 1-(3-aminopropyl)-2-methyl-1H-imidazole, piperazine, 1-(2-aminoethyl)piperazine, 1-[3-(dimethylamino)propyl]piperazine, 1-(2-aminoethyl)piperidine, 2-(2-aminoethyl-1-methylpyrrolidine, mixtures thereof, and pharmaceutically acceptable salts thereof.

Exemplary beta-lactams include benzylpenicillin (penicillin G), phenoxymethylpenicillin (penicillin V), cloxacillin, dicloxacillin, flucloxacillin, methicillin, nafcillin, oxacillin, temocillin, amoxicillin, ampicillin, mecillinam, carbenicillin, ticarcillin, azlocillin, mezlocillin, piperacillin, cefoxitin, cefazolin, cephalexin, cephalosporin C, cephalothin, cefaclor, cefamandole, cefuroxime, cefotetan, cefixime, cefotaxime, cefpodoxime, ceftazidime, ceftriaxone, cefepime, cefpirome, ceftobiprole, biapenem, doripenem, ertapenem faropenem, imipenem, meropenem, panipenem, razupenem, tebipenem, thienamycin, aztreonam, tigemonam, nocardicin a, tabtoxinine, clavulanic acid, clavulanic acid, tazobactam, sulbactam and pharmaceutically acceptable salts thereof.

Other viscosity-lowering agents include tropane N-heterocycles, such as atropine, hyoscyamine, scopolamine, and salts thereof, as well as tiotropium and ipratropium salts, thiamine, allithiamine, prosultiamine, fursultiamine, benfotiamine, sulbutiamine, quaternium 15; 1-(3-aminopropyl)-2-methyl-1H-imidazole dihydrochloride; creatinine; biotin, cimetidine, piperocaine, cyclomethylcaine, granisetron, moxifloxacin, chloroquine, mepivacaine, levetriacetam, bupivacaine, cinchocaine, clindamycin and pharmaceutically acceptable salts thereof. Thiamine is an especially preferred viscosity-lowering agent.

In certain formulations, the following compounds are not preferred: creatinine, cadaverine, lidocaine, arginine and lysine, and are excluded from the scope of the foregoing formulas and definitions of useful viscosity-lowering agents.

C. Excipients

A wide variety of pharmaceutical excipients useful for liquid protein formulations are known to those skilled in the art. They include one or more additives, such as liquid solvents or co-solvents; sugars or sugar alcohols such as mannitol, trehalose, sucrose, sorbitol, fructose, maltose, lactose, or dextrans; surfactants such as TWEEN® 20, 60, or 80 (polysorbate 20, 60, or 80); buffering agents; preservatives such as benzalkonium chloride, benzethonium chloride, tertiary ammonium salts, and chlorhexidinediacetate; carriers such as poly(ethylene glycol) (PEG); antioxidants such as ascorbic acid, sodium metabisulfite, and methionine; chelating agents such as EDTA or citric acid; or biodegradable polymers such as water soluble polyesters; cryoprotectants; lyoprotectants; bulking agents; and stabilizing agents.

Other pharmaceutically acceptable carriers, excipients, or stabilizers, such as those described in Remington: "The Science and Practice of Pharmacy", 20th edition, Alfonso R. Gennaro, Ed., Lippincott Williams & Wilkins (2000) may also be included in a protein formulation described herein, provided that they do not adversely affect the desired characteristics of the formulation.

The viscosity-lowering agents described herein can be combined with one or more other types of viscosity-lowering agents, for example, organophosphates described in co-filed PCT application entitled "LIQUID PROTEIN FORMULATIONS CONTAINING ORGANOPHOSPHATES" by Arsia Therapeutics; water soluble dyes described in co-filed PCT application entitled "LIQUID PROTEIN FORMULATIONS CONTAINING WATER SOLUBLE ORGANIC DYES" by Arsia Therapeutics; ionic liquids described in co-filed PCT application entitled "LIQUID PROTEIN FORMULATIONS CONTAINING IONIC LIQUIDS" by Arsia Therapeutics.

III. Methods of Making

The protein, such as a mAb, to be formulated may be produced by any known technique, such as by culturing cells transformed or transfected with a vector containing one or more nucleic acid sequences encoding the protein, as is well known in the art, or through synthetic techniques (such as recombinant techniques and peptide synthesis or a combination of these techniques), or may be isolated from an endogenous source of the protein.

Purification of the protein to be formulated may be conducted by any suitable technique known in the art, such as, for example, ethanol or ammonium sulfate precipitation, reverse phase HPLC, chromatography on silica or cation-exchange resin (e.g., DEAE-cellulose), dialysis, chromatofocusing, gel filtration using protein A SEPHAROSE® columns (e.g., SEPHADEX® G-75) to remove contaminants, metal chelating columns to bind epitope-tagged forms, and ultrafiltration/diafiltration (non-limiting examples include centrifugal filtration and tangential flow filtration (TFF)).

Inclusion of viscosity-lowering agents at viscosity-reducing concentrations such as 0.010 M to 1.0 M, preferably 0.050 M to 0.50 M, most preferably 0.10 M to 0.30 M, allows a solution of the pharmaceutically active mAb to be purified and/or concentrated at higher mAb concentrations using common methods known to those skilled in the art, including but not limited to tangential flow filtration, centrifugal concentration, and dialysis.

In some embodiments, lyophilized formulations of the proteins are provided and/or are used in the preparation and manufacture of the low-viscosity, concentrated protein formulations. In some embodiments, the pre-lyophilized protein in a powder form is reconstituted by dissolution in an aqueous solution. In this embodiment, the liquid formulation is filled into a specific dosage unit container such as a vial or pre-filled mixing syringe, lyophilized, optionally with lyoprotectants, preservatives, antioxidants, and other typical pharmaceutically acceptable excipients, then stored under sterile storage conditions until shortly before use, at which time it is reconstituted with a defined volume of diluent, to bring the liquid to the desired concentration and viscosity.

The formulations described herein may be stored by any suitable method known to one skilled in the art. Non-limiting examples of methods for preparing the protein formulations for storage include freezing, lyophilizing, and spray drying the liquid protein formulation. In some cases, the lyophilized formulation is frozen for storage at subzero temperatures, such as at about −80° C. or in liquid nitrogen. In some cases, a lyophilized or aqueous formulation is stored at 2-8° C.

Non-limiting examples of diluents useful for reconstituting a lyophilized formulation prior to injection include sterile water, bacteriostatic water for injection (BWFI), a pH buffered solution (e.g., phosphate-buffered saline), sterile saline solution, Ringer's solution, dextrose solution, or aqueous solutions of salts and/or buffers. In some cases, the formulation is spray-dried and then stored.

IV. Administration to an Individual in Need Thereof

The protein formulations, including, but not limited to, reconstituted formulations, are administered to a person in need thereof by intramuscular, intraperitoneal (i.e., into a body cavity), intracerobrospinal, or subcutaneous injection using an 18-32 gauge needle (optionally a thin-walled needle), in a volume of less than about 5 mL, less that about 3 mL, preferably less than about 2 mL, more preferably less than about 1 mL.

The appropriate dosage ("therapeutically effective amount") of the protein, such as a mAb, will depend on the condition to be treated, the severity and course of the disease or condition, whether the protein is administered for preventive or therapeutic purposes, previous therapy, the patient's clinical history and response to the protein, the type of protein used, and the discretion of the attending physician. The protein is suitably administered at one time in single or multiple injections, or over a series of treatments, as the sole treatment, or in conjunction with other drugs or therapies.

Dosage formulations are designed so that the injections cause no significant signs of irritation at the site of injection, for example, wherein the primary irritation index is less than 3 when evaluated using a Draize scoring system. In an alternative embodiment, the injections cause macroscopically similar levels of irritation when compared to injections of equivalent volumes of saline solution. In another embodiment, the bioavailability of the protein is higher when compared to the otherwise same formulation without the viscosity-lowering agent(s) administered in the same way. In another embodiment, the formulation is at least approximately as effective pharmaceutically as about the same dose of the protein administered by intravenous infusion.

In a preferred embodiment, the formulation is injected to yield increased levels of the therapeutic protein. For example, the AUC value may be at least 10%, preferably at least 20%, larger than the same value computed for the otherwise same formulation without the viscosity-lowering agent(s) administered in the same way.

The viscosity-lowering agent may also affect bioavailability. For example, the percent bioavailability of the protein may be at least 1.1 times, preferably at least 1.2 times the percent bioavailability of the otherwise same formulation without the viscosity-lowering agent(s) administered in the same way.

The viscosity-lowering agent may also affect the pharmacokinetics. For example, the $C_{MAX}$ after SC or IM injection may be at least 10%, preferably at least 20%, less than the $C_{MAX}$ of an approximately equivalent pharmaceutically effective intravenously administered dose.

In some embodiments, the proteins are administered at a higher dosage and a lower frequency than the otherwise same formulations without the viscosity-lowering agent(s).

The lower viscosity formulations require less injection force. For example, the injection force may be at least 10%, preferably at least 20%, less than the injection force for the otherwise same formulation without the viscosity-lowering agent(s) administered in the same way. In one embodiment, the injection is administered with a 27 gauge needle and the injection force is less than 30 N. The formulations can be administered in most cases using a very small gauge needle, for example, between 27 and 31 gauge, typically 27, 29 or 31 gauge.

The viscosity-lowering agent may be used to prepare a dosage unit formulation suitable for reconstitution to make a liquid pharmaceutical formulation for subcutaneous or intramuscular injection. The dosage unit may contain a dry powder of one or more proteins; one or more viscosity-lowering agents; and other excipients. The proteins are present in the dosage unit such that after reconstitution in a pharmaceutically acceptable solvent, the resulting formulation has a protein concentration from about 100 mg to about 2,000 mg per 1 mL (mg/mL). Such reconstituted formulations may have an absolute viscosity of from about 1 cP to about 50 cP at 25° C.

The low viscosity formulation can be provided as a solution or in a dosage unit form where the protein is lyophilized in one vial, with or without the viscosity-lowering agent and the other excipients, and the solvent, with or without the viscosity-lowering agent and other excipients, is provided in a second vial. In this embodiment, the solvent is added to the protein shortly before or at the time of injection to ensure uniform mixing and dissolution.

The viscosity-lowering agent(s) are present in the formulations at concentrations that cause no significant signs of toxicity and/or no irreversible signs of toxicity when administered via subcutaneous, intramuscular, or other types of injection. As used herein, "significant signs of toxicity" include intoxication, lethargy, behavioral modifications such as those that occur with damage to the central nervous system, infertility, signs of serious cardiotoxicity such as cardiac arrhythmia, cardiomyopathy, myocardial infarctions, and cardiac or congestive heart failure, kidney failure, liver failure, difficulty breathing, and death.

In preferred embodiments the formulations cause no significant irritation when administered not more than twice daily, once daily, twice weekly, once weekly or once monthly. The protein formulations can be administered causing no significant signs of irritation at the site of injection, as measured by a primary irritation index of less than 3, less than 2, or less than 1 when evaluated using a Draize scoring system. As used herein, "significant signs of irritation" include erythema, redness, and/or swelling at the site of injection having a diameter of greater than 10 cm, greater than 5 cm, or greater than 2.5 cm, necrosis at the site of injection, exfoliative dermatitis at the site of injection, and severe pain that prevents daily activity and/or requires medical attention or hospitalization. In some embodiments, injections of the protein formulations cause macroscopically similar levels of irritation when compared to injections of equivalent volumes of saline solution.

The protein formulations can exhibit increased bioavailability compared to the otherwise same protein formulation without the viscosity-lowering agent(s) when administered via subcutaneous or intramuscular injection. "Bioavailability" refers to the extent and rate at which the bioactive species such as a mAb, reaches circulation or the site of action. The overall bioavailability can be increased for SC or IM injections as compared to the otherwise same formulations without the viscosity-lowering agent(s). "Percent bioavailability" refers to the fraction of the administered dose of the bioactive species which enters circulation, as determined with respect to an intravenously administered dose. One way of measuring the bioavailability is by comparing the "area under the curve" (AUC) in a plot of the plasma concentration as a function of time. The AUC can be calculated, for example, using the linear trapezoidal rule. "$AUC_\infty$", as used herein, refers to the area under the plasma concentration curve from time zero to a time where the plasma concentration returns to baseline levels. "$AUC_{0\text{-}t}$", as used herein, refers to the area under the plasma concentration curve from time zero to a time, t, later, for example to the time of reaching baseline. The time will typically be measured in days, although hours can also be used as will be apparent by context. For example, the AUC can be increased by more than 10%, 20%, 30%, 40%, or 50% as compared to the otherwise same formulation without the viscosity-lowering agent(s) and administered in the same way.

As used herein, "$t_{max}$" refers to the time after administration at which the plasma concentration reaches a maximum.

As used herein, "$C_{max}$" refers to the maximum plasma concentration after dose administration, and before administration of a subsequent dose.

As used herein, "$C_{min}$" or "$C_{trough}$" refers to the minimum plasma concentration after dose administration, and before administration of a subsequent dose.

The $C_{max}$ after SC or IM injection may be less, for example, at least 10%, more preferably at least 20%, less than the $C_{max}$ of an intravenously administered dose. This reduction in $C_{max}$ may also result in decreased toxicity.

The pharmacokinetic and pharmacodynamic parameters may be approximated across species using approaches that are known to the skilled artisan. The pharmacokinetics and pharmacodynamics of antibody therapeutics can differ markedly based upon the specific antibody. An approved murine mAb was shown to have a half-life in humans of ~1 day, while a human mAb will typically have a half-life of ~25 days (Waldmann et al., *Int. Immunol.*, 2001, 13:1551-1559). The pharmacokinetics and pharmacodynamics of antibody therapeutics can differ markedly based upon the route of administration. The time to reach maximal plasma concentration after IM or SC injection of IgG typically ranges from 2 to 8 days, although shorter or longer times may be encountered (Wang et al., *Clin. Pharm. Ther.*, 2008, 84(5):548-558). The pharmacokinetics and pharmacodynamics of antibody therapeutics can differ markedly based upon the formulation.

The low-viscosity protein formulations can allow for greater flexibility in dosing and decreased dosing frequencies compared to those protein formulations without the viscosity-lowering agent(s). For example, by increasing the dosage administered per injection multiple-fold, the dosing frequency can in some embodiments be decreased from once every 2 weeks to once every 6 weeks. The protein formulations, including, but not limited to, reconstituted formulations, can be administered using a heated and/or self-mixing syringe or autoinjector. The protein formulations can also be pre-heated in a separate warming unit prior to filling the syringe.

i. Heated Syringes

The heated syringe can be a standard syringe that is pre-heated using a syringe warmer. The syringe warmer will generally have one or more openings each capable of receiving a syringe containing the protein formulation and a means for heating and maintaining the syringe at a specific (typically above the ambient) temperature prior to use. This will be referred to herein as a pre-heated syringe. Suitable heated syringe warmers include those available from Vista Dental Products and Inter-Med. The warmers are capable of accommodating various sized syringes and heating, typically to within 1° C., to any temperature up to about 130° C. In some embodiments the syringe is pre-heated in a heating bath such as a water bather maintained at the desired temperature.

The heated syringe can be a self-heating syringe, i.e. capable of heating and maintaining the liquid formulation inside the syringe at a specific temperature. The self-heating syringe can also be a standard medical syringe having attached thereto a heating device. Suitable heating devices capable of being attached to a syringe include syringe heaters or syringe heater tape available from Watlow Electric Manufacturing Co. of St. Louis, Mo., and syringe heater blocks, stage heaters, and in-line perfusion heaters available from Warner Instruments of Hamden, Conn., such as the SW-61 model syringe warmer. The heater may be controlled through a central controller, e.g. the TC-324B or TC-344B model heater controllers available from Warner Instruments.

The heated syringe maintains the liquid protein formulation at a specified temperature or to within 1° C., within 2° C., or within 5° C. of a specified temperature. The heated syringe can maintain the protein formulation at any temperature from room temperature up to about 80° C., up to about 60° C., up to about 50° C., or up to about 45° C. as long as the protein formulation is sufficiently stable at that temperature. The heated syringe can maintain the protein formulation at a temperature between 20° C. and 60° C., between 21° C. and 45° C., between 22° C. and 40° C., between 25° C. and 40° C., or between 25° C. and 37° C. By maintaining the protein formulations at an elevated temperature during injection, the viscosity of the liquid formulation is decreased, the solubility of the protein in the formulation is increased, or both.

ii. Self-Mixing Syringes

The syringe can be self-mixing or can have a mixer attached. The mixer can be a static mixer or a dynamic mixer. Examples of static mixers include those disclosed in U.S. Pat. Nos. 5,819,988, 6,065,645, 6,394,314, 6,564,972, and 6,698,622. Examples of some dynamic mixers can include those disclosed in U.S. Pat. Nos. 6,443,612 and 6,457,609, as well as U.S. Patent Application Publication No. US 2002/0190082. The syringe can include multiple barrels for mixing the components of the liquid protein formulation. U.S. Pat. No. 5,819,998 describes syringes with two barrels and a mixing tip for mixing two-component viscous substances.

iii. Autoinjectors and Pre-Filled Syringes of Protein Formulations

The liquid protein formulation can be administered using a pre-filled syringe autoinjector or a needleless injection device. Autoinjectors include a handheld, often pen-like, cartridge holder for holding replaceable pre-filled cartridges and a spring based or analogous mechanism for subcutaneous or intramuscular injections of liquid drug dosages from a pre-filled cartridge. Autoinjectors are typically designed for self-administration or administration by untrained personnel. Autoinjectors are available to dispense either single dosages or multiple dosages from a pre-filled cartridge. Autoinjectors enable different user settings including inter alia injection depth, injection speed, and the like. Other injection systems can include those described in U.S. Pat. No. 8,500,681.

The lyophilized protein formulation can be provided in pre-filled or unit-dose syringes. U.S. Pat. Nos. 3,682,174; 4,171,698; and 5,569,193 describe sterile syringes containing two-chambers that can be pre-filled with a dry formulation and a liquid that can be mixed immediately prior to injection. U.S. Pat. No. 5,779,668 describes a syringe system for lyophilization, reconstitution, and administration of a pharmaceutical composition. In some embodiments the protein formulation is provided in lyophilized form in a pre-filled or unit-dose syringe, reconstituted in the syringe prior to administration, and administered as a single subcutaneous or intramuscular injection. Autoinjectors for delivery of unit-dose lyophilized drugs are described in WO 2012/010,832. Auto injectors such as the Safe Click Lyo™ (marketed by Future Injection Technologies, Ltd., Oxford, U.K.) can be used to administer a unit-dose protein formulation where the formulation is stored in lyophilized form and reconstituted just prior to administration. In some embodiments the protein formulation is provided in unit-dose cartridges for lyophilized drugs (sometimes referred to as Vetter cartridges). Examples of suitable cartridges can include those described in U.S. Pat. Nos. 5,334,162 and 5,454,786.

V. Methods of Purification and Concentration

The viscosity-lowering agents can also be used to assist in protein purification and concentration. The viscosity-lowering agent(s) and excipients are added to the protein in an effective amount reduce the viscosity of the protein solution. For example, the viscosity-lowering agent is added to a concentration of between about 0.01 M and about 1.0 M, preferably between about 0.01 M and about 0.50 M, and most preferably between about 0.01 M and about 0.25 M.

The viscosity-lowering agent solution containing protein is then purified or concentrated using a method selected from the group consisting of ultrafiltration/diafiltration, tangential flow filtration, centrifugal concentration, and dialysis.

Examples

The foregoing will be further understood by the following non-limiting examples.

All viscosities of well-mixed aqueous mAb solutions were measured using either a mVROC microfluidic viscometer (RheoSense) or a DV2T cone and plate viscometer (Brookfield; "C & P") after a 5 minute equilibration at 25° C. (unless otherwise indicated). The mVROC viscometer was equipped with an "A" or "B" chip, each manufactured with a 50 micron channel. Typically, 0.10 mL of protein solution was back-loaded into a gastight microlab instrument syringe (Hamilton; 100 µL), affixed to the chip, and measured at multiple flow rates, approximately 20%, 40%, and 60% of the maximum pressure for each chip. For example a sample of approximately 50 cP would be measured at around 10, 20, and 30 µL/min (approximately 180, 350, and 530 s$^{-1}$, respectively, on an "A" chip) until viscosity stabilized, typically after at least 30 seconds. An average absolute viscosity and standard deviation was then calculated from at least these three measurements. The C & P viscometer was equipped with a CPE40 or CPE52 spindle (cone angle of 0.8° and 3.0°, respectively) and 0.50 mL samples were measured at multiple shear rates between 2 and 400 s$^{-1}$. Specifically, samples were measured for 30 seconds each at 22.58, 24.38, 26.25, 28.13, 30, 31.88, 45, 67.5, 90, 112.5, 135, 157.5, 180, 202.5, 247, 270, 292.5, 315, 337.5, 360, 382, 400 s$^{-1}$, starting at a shear rate that gave at least 10% torque, and continuing until instrument torque reached 100%. An extrapolated zero-shear viscosity was then determined from a plot of dynamic viscosity versus shear rate for the samples measured on a DV2T cone and plate viscometer. The extrapolated zero-shear viscosities reported are the average and standard deviation of at least three measurements.

Example 1: Effect of a Viscosity-Lowering Agent, Camphorsulfonic Acid Lysine (CSAL), on the Viscosity of Solutions of Biosimilar ERBITUX®

Materials and Methods

A commercially-obtained biosimilar ERBITUX® (100-400 mg) containing pharmaceutical excipients (Polysorbate 80, phosphate buffer, and NaCl) was purified. First, Polysorbate 80 was removed using DETERGENT-OUT® TWEEN® Medi Columns (G-Biosciences). Next, the resulting solutions were extensively buffer-exchanged into 20 mM sodium phosphate buffer (PB; pH 7.0) or 20 mM CSAL (pH 7.0) and concentrated to a final volume of less than 10 mL on Jumbosep centrifugal concentrators (Pall Corp.). The collected protein solution was freeze-dried. The dried protein cakes, containing protein and buffer salts or agent, were reconstituted to a final volume of 0.15-1.3 mL. These samples were reconstituted using additional PB (pH 7.0) or CSAL (pH 7.0) sufficient to bring the final concentration of PB or CSAL to 0.25 M. The final concentration of mAb in solution was determined by light absorbance at 280 nm. Reported protein concentrations represent the range of all protein samples included in each Table or Figure. Specifically, reported values are the median plus or minus half the range. Extrapolated zero-shear using an experimentally determined extinction coefficient of 1.4 L/g·cm and viscosities reported were measured on a DV2T cone and plate viscometer.

Results

Figure 1B:
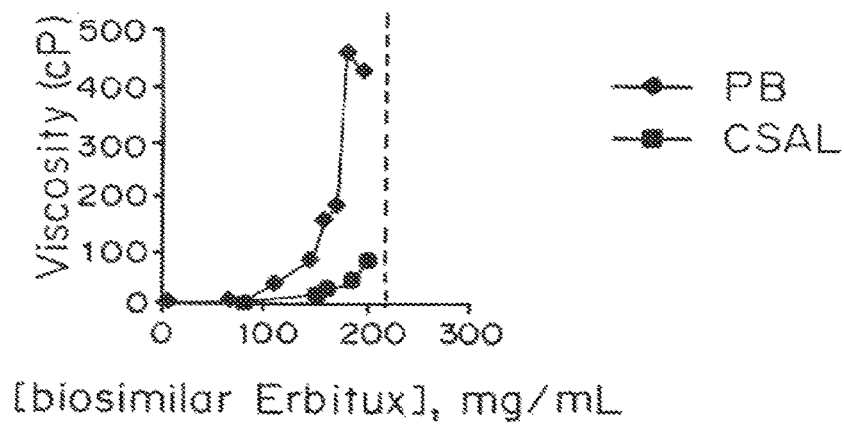

The data in FIG. 1A and FIG. 1B demonstrate the viscosity-lowering effect of CSAL on aqueous solutions of biosimilar ERBITUX®. The viscosity of a solution of biosimilar ERBITUX® in phosphate buffer (PB) increases exponentially with increasing mAb concentration. The viscosity of a solution of biosimilar ERBITUX® in the presence of CSAL is seen to increase exponentially with increasing mAb concentration, but to a lesser extent than the formulation in PB i.e. the viscosity gradient is reduced. The data in FIG. 1A and FIG. 1B show that the higher the concentration of mAb, the greater the viscosity-lowering effect. The magnitude of viscosity-lowering effects afforded by the replacement of PB with CSAL varied from 1.1-fold at 100±5 mg/mL to 10.3-fold at 227±5 mg/mL mAb.

Example 2: Viscosity-Lowering Effect of a Viscosity-Lowering Agent, Camphorsulfonic Acid Lysine (CSAL), as a Function of Concentration of Biosimilar AVASTIN®

Materials and Methods

A biosimilar AVASTIN® obtained commercially and containing pharmaceutical excipients (Polysorbate 20, phosphate buffer, citrate buffer, mannitol, and NaCl) was purified, buffer exchanged, concentrated, dried, reconstituted, and analyzed as described in Example 1 above (using the extinction coefficient of 1.7 L/g·cm at 280 nm). The protein was formulated to contain either 0.25 M phosphate buffer or 0.25 M CSAL.

Results

Figure 2A:
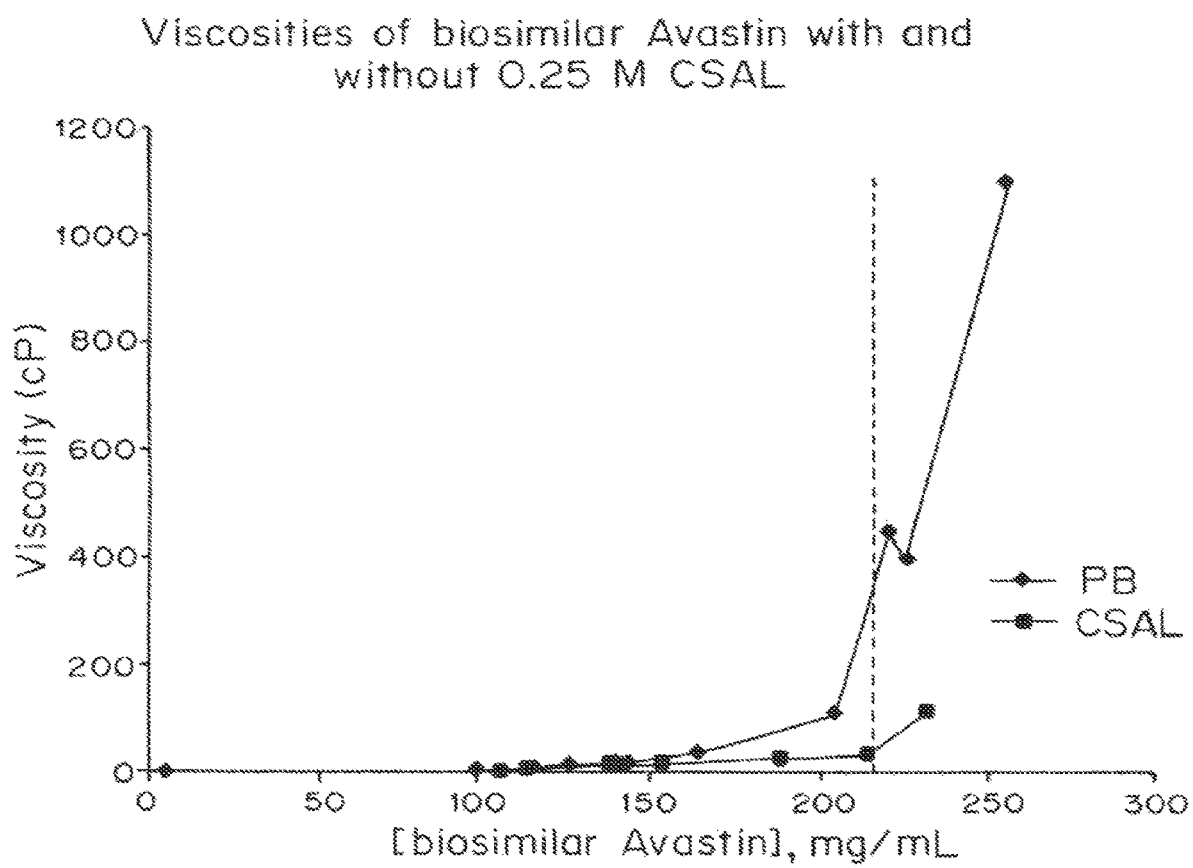
FIG. 2A and FIG. 2B depict the viscosity in cP as a function of the protein concentration (in mg/mL) for solutions of biosimilar bevacizumab (AVASTIN®) in 0.25 M phosphate buffer (PB; diamonds) and 0.25 M CSAL (squares) at 25° C. and final pH of 7.0. The data points incorporate standard deviations which, however, are often smaller than the symbols.
Figure 2B:
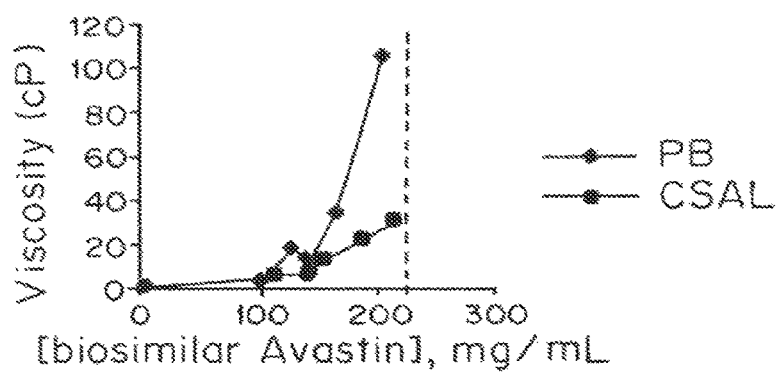

FIG. 2A and FIG. 2B depict the viscosity of aqueous mAb solutions as a function of mAb concentration in aqueous buffered solution and with CSAL. The viscosity of biosimilar AVASTIN® in aqueous phosphate buffer and in the presence of CSAL increases exponentially with increasing concentration; however, as in the case of biosimilar ERBITUX®, this increase is much less marked for the CSAL-containing formulation, i.e. the viscosity gradient is reduced. In general, the higher the mAb concentration, the greater the viscosity-lowering effect observed. The magnitude of viscosity-lowering effects afforded by the replacement of PB with CSAL varied from 2.1-fold at 80 mg/mL to 3.7-fold at 230±5 mg/mL mAb.

Example 3: Viscosity-Lowering Effect as a Function of CSAL Concentration for Aqueous Solutions of Biosimilar ERBITUX®

Materials and Methods

Samples were purified, buffer exchanged, concentrated, dried, reconstituted, and analyzed similarly to Example 1 above. The final concentration of CSAL upon reconstitution in an aqueous CSAL solution ranged from 0.25 M to 0.50 M.

Results

Table 1 shows the viscosity of solutions of biosimilar ERBITUX® formulated in 0.25 M phosphate buffer (no CSAL as a control) and with varying concentrations of CSAL. The viscosity-lowering effect of CSAL is seen to rise from 8.4- to 12.1-fold with increasing viscosity-lowering agent concentration. The data in Table 1 show that the higher the concentration of CSAL, the greater the viscosity-lowering effect, at least within the agent concentration range tested.

TABLE 1

Viscosities of aqueous solutions of biosimilar
ERBITUX ® (155 ± 5 mg/mL, pH 7.0)
in the presence of different concentrations of CSAL at 25° C.

| [CSAL], M | Viscosity, cP | Fold viscosity reduction (compared to no CSAL present) |
| --- | --- | --- |
| 0 | 154 ± 0 | 1 |
| 0.25 | 18.3 ± 0.0 | 8.4 |
| 0.38 | 14.9 ± 0.1 | 10.3 |
| 0.50 | 12.7 ± 0.1 | 12.1 |

Example 4: Viscosities of Solutions of Biosimilar ERBITUX® as a Function of Temperature in the Presence of Various Viscosity-Lowering Agents Materials and Methods Aqueous solutions of biosimilar ERBITUX® containing various viscosity-lowering agents were prepared as described in Example 1. Specifically, 20 mM solutions of the viscosity-lowering agents of interest were used for buffer exchange, and the lyophilized cakes were reconstituted to 0.25 M of each viscosity-lowering agent. For the sample containing CSA-APMI, biosimilar ERBITUX® was extensively buffer exchanged into 2 mM PB (pH 7.0), and concentrated to a final volume of less than 10 mL on Jumbosep centrifugal concentrators (Pall Corp.). The sample was first aliquoted. Then, an appropriate amount of CSAAPMI solution (pH 7.0) was added to each aliquot such that upon reconstitution with water, the final excipient concentration is 0.25 M. The protein solutions were then freeze-dried. The dried protein cakes, containing protein and viscosity-lowering agent (and a negligible amount of buffer salts) were reconstituted to a final volume of approximately 0.10 mL and viscosity-lowering agent concentration as previously described.

Results

Table 2 shows viscosity data for biosimilar ERBITUX® in the presence of six viscosity-lowering agents—camphorsulfonic acid lysine (CSAL), camphorsulfonic acid arginine (CSAA), benzenesulfonic acid lysine (BSAL), benzenesulfonic acid arginine (BSAA), naphthalenesulfonic acid arginine (NSAA), and camphorsulfonic acid 1-(3-aminopropyl)-2-methyl-1H-imidazole (CSAAPMI). The data in Table 2 show a reduction in viscosity of at least about 9-fold for all six viscosity-lowering agents compared to a solution of biosimilar ERBITUX® in phosphate buffer under otherwise the same conditions. The most efficacious viscosity-lowering agent—CSAAPMI—lowered viscosity by >40-fold.

Additionally, the data in Table 3 show that at multiple temperatures ranging from 20° C. to 30° C., a 225 mg/mL solution of biosimilar ERBITUX® prepared with 0.25 M CSAA had the lowest viscosity of the five viscosity-lowering agents. Thus, the observed trends in viscosities at 25° C. seem to be predictive of those at temperatures of at least 20° C. and 30° C.

TABLE 2

Reduction in viscosity of aqueous solutions of biosimilar
ERBITUX ® (226 ± 6 mg/mL, pH 7.0) formulated
with various 0.25M viscosity-lowering agents, as compared
to that in 0.25M sodium phosphate buffer (PB) at 25° C.

| Agent | Viscosity, cP | Fold reduction |
| --- | --- | --- |
| PB | 1130 ± 7 | 1 |
| CSAL | 109 ± 1 | 10.4 |
| CSAA | 58.0 ± 0.3 | 19.5 |
| BSAL | 126 ± 1 | 9.0 |
| BSAA | 61.3 ± 0.9 | 18.4 |
| NSAA | 69.4 ± 0.6 | 16.3 |
| CSAAPMI | 25.7 ± 1.5 | 44.0 |

TABLE 3

Viscosities of aqueous solutions of biosimilar ERBITUX ® (225 ± 5 mg/mL, pH 7.0) formulated with various 0.25M viscosity-lowering agents.

| Temp. | Viscosity, cP Agent | | | | | |
|---|---|---|---|---|---|---|
| | PB | CSAL | CSAA | BSAL | BSAA | NSAA |
| 20° C. | 1810 ± 10 | 166 ± 2 | 79.6 ± 0.9 | 193 ± 0 | 85.2 ± 0.6 | 103 ± 0 |
| 25° C. | 1130 ± 7 | 109 ± 1 | 58.0 ± 0.3 | 126 ± 1 | 61.3 ± 0.9 | 69.4 ± 0.6 |
| 30° C. | 723 ± 0 | 78.4 ± 1.5 | 46.9 ± 0.6 | 89.8 ± 0.8 | 50.5 ± 1.9 | 60.9 ± 4.3 |

Example 5: The Effect of Temperature on Viscosity of Aqueous Solutions of Biosimilar AVASTIN® Formulated with Various Viscosity-Lowering Agents Materials and Methods Solutions of biosimilar AVASTIN® containing different viscosity-lowering agents were prepared as described in Example 1 above. In particular, 20 mM solutions of the viscosity-lowering agents of interest were used for buffer exchange, and the lyophilized cakes were reconstituted to 0.15 or 0.25 M viscosity-lowering agent.

Results

As seen in Table 4, 0.25 M CSAL lowered the viscosity of a 230±5 mg/mL solution of biosimilar AVASTIN® at all three temperatures between 20 and 30° C. Furthermore, 0.15 M CSAL reduces viscosity to approximately the same absolute value as 0.25 M CSAL at 20 and 25° C. and is equally effective at 30° C.

The data in Table 5 compare the effects of CSAL and BSAL at a concentration of 0.15 M. CSAL is a superior viscosity-lowering agent compared to BSAL at all three temperatures.

TABLE 4

Viscosities of aqueous solutions of biosimilar AVASTIN ® (230 ± 5 mg/mL, pH 7.0) formulated with 0.25 and 0.15M CSAL at different temperatures.

| Temperature | Viscosity, cP | | |
|---|---|---|---|
| | 0.25M PB | 0.25M CSAL | 0.15M CSAL |
| 20° C. | 563 ± 2 | 152 ± 0 | 157 ± 0 |
| 25° C. | 397 ± 2 | 107 ± 4 | 113 ± 0 |
| 30° C. | 311 ± 4 | 95.5 ± 5.4 | 91.7 ± 3.3 |

TABLE 5

Viscosities of aqueous solutions of biosimilar AVASTIN ® (230 ± 5 mg/mL, pH 7.0) formulated with 0.15M CSAL and BSAL at different temperatures.

| Temperature | Viscosity, cP | | |
|---|---|---|---|
| | 0.25M PB | 0.15M CSAL | 0.15M BSAL |
| 20° C. | 563 ± 2 | 157 ± 0 | 395 ± 3 |
| 25° C. | 397 ± 2 | 113 ± 0 | 227 ± 5 |
| 30° C. | 311 ± 4 | 91.7 ± 3.3 | 175 ± 7 |

Example 6: Removal of CSAL Reverses Viscosity-Lowering Effect in mAb Solutions Materials and Methods Three samples each of biosimilar ERBITUX® and biosimilar AVASTIN® were prepared. First, Polysorbate was removed from the commercially obtained mAb solutions. The resulting solution with remaining pharmaceutical excipients was either (i) concentrated on a centrifugal device with a 100-kDa molecular weight cutoff (MWCO) (Pall Corp.) as a control sample (original excipients), (ii) buffer exchanged into 0.25 M CSAL as described in Example 1, or (iii) buffer exchanged into 0.25 M CSAL as described in Example 1, reconstituted, and then further exchanged into 0.25 M PB. In this third instance, exchange into 0.25 M phosphate buffer proceeded first by overnight dialysis against 20 mM PB (50-kDa MWCO, Spectrum Labs). The partially dialyzed samples were then diluted to 60 mL in 0.25 M PB and subjected to centrifugal concentration (30-kDa MWCO Jumbosep (Pall Corp.), followed by a 100-kDa MWCO Macrosep device (Pall Corp.)). The viscosities of these three aqueous solutions were determined as described in Example 1 above.

Results

The viscosities of aqueous solutions of both biosimilar ERBITUX® and biosimilar AVASTIN® decreased in the presence of CSAL—2.7- and 1.5-fold, respectively—but then increased when CSAL was removed (see Tables 6 and 7). Furthermore, upon removal of CSAL, mAb solution viscosities returned to approximately the same level as the original solutions, suggesting that CSAL does not damage the protein and showing that it is necessary for the observed viscosity reduction.

TABLE 6

Viscosities of aqueous solutions of biosimilar ERBITUX ® (80 ± 5 mg/mL, pH 7.0) at 25° C.

| Formulation | Viscosity, cP |
|---|---|
| Original excipients | 8.30 ± 0.04 |
| 0.25M CSAL | 3.08 ± 0.18 |
| 0.25M CSAL exchanged into 0.25M PB | 9.43 ± 0.04 |

TABLE 7

Viscosities of aqueous solutions of biosimilar AVASTIN ® (101 ± 5 mg/mL, pH 7.0) at 25° C.

| Formulation | Viscosity, cP |
|---|---|
| Original excipients | 6.08 ± 0.19 |
| 0.25M CSAL | 4.03 ± 0.24 |
| 0.25M CSAL exchanged into 0.25M PB | 6.61 ± 0.08 |

Example 7: Camphorsulfonic Acid-Containing Viscosity-Lowering Agents Provide Large Viscosity Reductions in Aqueous Solutions of AVASTIN® and Biosimilar AVASTIN®

Materials and Methods

AVASTIN® and a biosimilar AVASTIN® obtained commercially and containing pharmaceutical excipients (AVASTIN®: trehalose, sodium phosphate buffer, and Polysorbate 20; biosimilar AVASTIN®: Polysorbate 20, phosphate buffer, citrate buffer, mannitol, and NaCl) were purified, buffer exchanged, concentrated, freeze-dried, and reconstituted as described above. Samples in Table 8 were prepared as described in Example 1 above (using the protein extinction coefficient of 1.7 L/g·cm at 280 nm) and measured on a C & P viscometer. Viscosity-reduced samples in Table 9 were prepared as described in Example 4 above, but mAb was extensively buffer exchanged into 2 mM PB. Subsequently, the appropriate amount of viscosity-lowering agent was added to result in a final viscosity-lowering agent concentration of 0.15-0.35 M upon reconstitution. Viscosities were measured using a RheoSense mVROC microfluidic viscometer equipped with an "A" or "B" chip.

Results

The data in Tables 8 and 9 demonstrate the viscosity-lowering effect of different viscosity-lowering agents on aqueous solutions of biosimilar AVASTIN®. Viscosity reductions up to 2.5-fold (compared to mAb solutions in PB) are observed for aqueous solutions of biosimilar AVASTIN® in the presence of viscosity-lowering agents containing CSA.

TABLE 8

Viscosities of aqueous solutions of biosimiar AVASTIN ® (200 ± 5 mg/mL, pH 7.0) at 25° C. with various viscosity-lowering agents.

| Agent | [Salt] (M of anion) | Viscosity (cP) |
|---|---|---|
| PB | 0.25 | 96.8 ± 0.9 |
| NaCl | 0.25 | 121 ± 8 |
| Arginine•HCl | 0.25 | 83.2 ± 2.8 |
| Arginine•HCl | 0.3 | 71.8 ± 2.2 |
| Lysine•HCl | 0.25 | 137 ± 2 |
| BSA sodium salt | 0.25 | 133 ± 3 |
| CSA sodium salt | 0.25 | 55.7 ± 0.2 |
| BSAA | 0.25 | 75.3 ± 0.4 |
| Benzoic acid arginine | 0.15 | 52.2 ± 0.5 |
| Benzoic acid arginine | 0.25 | 51.4 ± 0.5 |
| CSAA | 0.25 | 48.5 ± 1.9 |
| CSA betaine* | 0.25 | 66.0 ± 0.7 |
| diCSA cadaverine | 0.25 | 85.5 ± 5.2 |
| diCSA cadaverine | 0.35 | 65.6 ± 1.6 |
| CSA canavanine | 0.15 | 60.5 ± 0.6 |
| CSA canavanine | 0.25 | 75.6 ± 3.0 |
| CSA carnitine* | 0.25 | 72.4 ± 1.7 |
| CSA dimethylpiperazine | 0.25 | 47.4 ± 1.3 |
| CSA dimethylpiperazine | 0.35 | 51.7 ± 0.9 |
| CSAL | 0.25 | 54.9 ± 0.9 |
| Chlorotheophylline arginine | 0.25 | 104.5 ± 6.5 |
| Ethandisulfonate diarginine* | 0.15 | 77.1 ± 0.3 |
| Ethandisulfonate diarginine* | 0.25 | 105 ± 4 |
| MSA arginine | 0.25 | 93.1 ± 0.9 |
| Toluenesulfonic acid arginine | 0.25 | 159 ± 5 |
| Toluenesulfonic acid lysine | 0.25 | 118 ± 1 |

*Contains equimolar NaCl; CSA = Camphorsulfonic acid, BSA = Benzenesulfonic acid, MSA = Methanesulfonic acid, PB = Phosphate buffer

TABLE 9

Viscosities of aqueous solutions of biosimilar AVASTIN ® (pH 7.0) at 25° C. with 0.15M viscosity-lowering agents (unless otherwise noted).

| Agent | [biosimilar AVASTIN] (mg/mL) | Viscosity (cP) |
|---|---|---|
| 0.25M PB | 220 | 213 ± 10 |
| 0.25M PB | 200 | 96.8 ± 0.9 |
| CSA-piperazine | 212 | 64.5 ± 13.1 |
| Lactobionic acid-tris | 219 | 109 ± 5 |
| CSA-4-aminopyridine | 229 | 86.4 ± 1.1 |
| Glucuronic acid-tris | 221 | 151 ± 5 |

Figure 3:
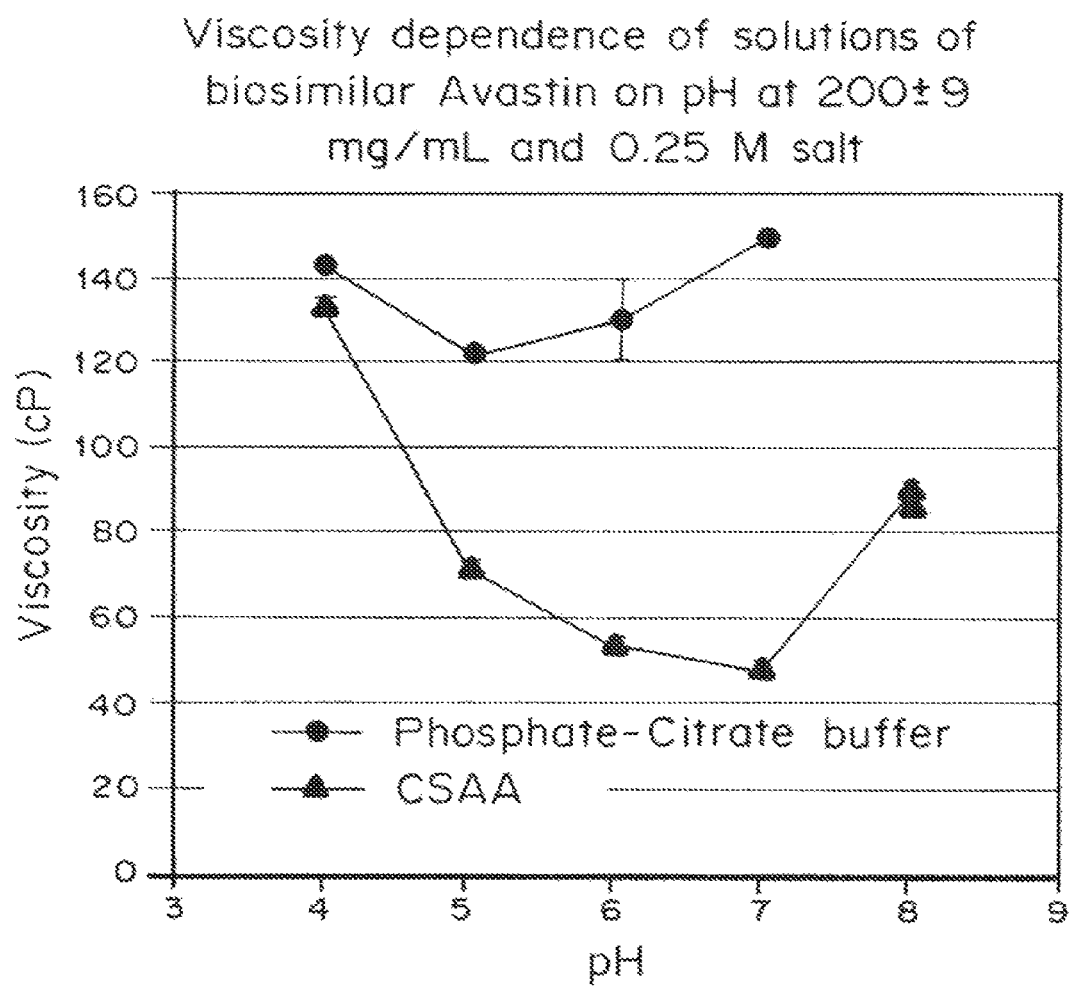
FIG. 3 is a graph of the viscosity (cP) of aqueous solutions of 200±9 mg/mL biosimilar bevacizumab (AVASTIN®) as a function of pH along the x-axis containing either phosphate-citrate buffer or camphorsulfonic acid arginine (CSAA) at a concentration of 0.25 M.

The viscosity of a 200±9 mg/mL aqueous solution of biosimilar AVASTIN® with CSAA was measured as a function of pH as depicted in FIG. 3. As pH increases, the magnitude of the viscosity-lowering effect resulting from the presence of CSAA in aqueous solutions of biosimilar AVASTIN® also increases, reaching a minimum viscosity and maximum viscosity-lowering effect around pH 7. The viscosity reduction by CSAA was compared as a function of pH for two different concentrations of biosimilar AVASTIN®. FIG. 4 demonstrates that 0.25 M CSAA results in a greater reduction in viscosity with increasing (i) concentration of the biosimilar AVASTIN® and (ii) pH.

Table 10 compares the viscosity reduction of biosimilar AVASTIN® to that of branded AVASTIN® with and without CSAL. The branded AVASTIN® solution has a much higher viscosity than a solution of the biosimilar mAb in the absence of the agent. However, the presence of 0.25 M CSAL results in a 1.8- and 3.3-fold reduction in viscosity of the biosimilar and branded AVASTIN® respectively; the viscosities of biosimilar and branded AVASTIN® are seen to be similar in the presence of 0.25 M CSAL.

TABLE 10

Viscosities of aqueous solutions containing 205 ± 5 mg/mL of biosimilar AVASTIN ® or branded AVASTIN ® with or without 0.25M CSAL measured at 25° C. and pH 7.0.

| Salt | Biosimilar AVASTIN ® (cP) | Branded AVASTIN ® (cP) |
|---|---|---|
| Phosphate Buffer | 96.8 ± 0.9 | 154 ± 4 |
| 0.25M CSAL | 54.9 ± 0.9 | 46.7 ± 0.9 |

CSAL = camphorsulfonic acid lysine

As demonstrated in Table 11, CSA 1-(3-aminopropyl)-2-methyl-1H-imidazole (CSAAPMI) with HCl provides superior viscosity reduction than CSAL, reducing the viscosity more than 5-fold as compared to the PB control for a solution of 210 mg/mL biosimilar AVASTIN®.

TABLE 11

Viscosities of aqueous solutions of biosimilar AVASTIN ® with various viscosity-lowering agents at 25° C. and pH 7.0.

| Agent | [Agent], M | [Protein], mg/mL | Viscosity, cP |
|---|---|---|---|
| PB | 0.25 | 220 | 213 ± 10 |
| CSAL | 0.25 | 210 | 63.0 ± 1.8 |
| CSAAPMI-2HCl | 0.25 | 210 | 40.9 ± 0.5 |

APMI = 1-(3-aminopropyl)-2-methyl-1H-imidazole

For a solution containing ~230 mg/mL biosimilar AVASTIN®, Table 12 demonstrates viscosity reduction of approximately 5-fold with sulfosalicylic acid-containing viscosity-lowering agents as well as for CSAAPMI and CSA thiamine.

TABLE 12

Viscosities of aqueous solutions containing 228 ± 5 mg/mL biosimilar AVASTIN® with viscosity-lowering agents at 25° C. and pH 7.0.

| Agent | Agent Concentration [M] | Viscosity (cP) |
| --- | --- | --- |
| PB | 0.25 | 397 ± 2 |
| CSAA | 0.25 | 116 ± 2 |
| CSAL | 0.25 | 113 ± 0 |
| Sulfosalicylic acid diarginine | 0.15 | 81.6 ± 1.7 |
| Sulfosalicylic acid dilysine | 0.25 | 73.4 ± 0.4 |
| CSAAPMI-2HCl | 0.25 | 71.8 ± 3.2 |
| CSAthiamine- 2NaCl | 0.15 | 83.7 ± 2.2 |

APMI = 1-(3-aminopropyl)-2-methyl-1H-imidazole;
CSA = camphorsulfonic acid

Example 8. The Effect of Viscosity-Lowering Agents on Aqueous Solutions of ERBITUX® and Biosimilar ERBITUX®

Materials and Methods

Aqueous solutions of biosimilar and branded ERBITUX® containing various viscosity-lowering agents were prepared as described in Example 1. Specifically, 20 mM solutions of the salts of interest were used for buffer exchange, and the lyophilized cakes were reconstituted to contain 0.25 M of each agent. Viscosities were measured using either a RheoSense mVROC microfluidic viscometer equipped with an "A" or "B" chip or a DV2T cone and plate viscometer.

Results

Table 13 shows data for biosimilar ERBITUX® (222±5 mg/mL) in the presence of five viscosity-lowering agents: CSAA, CSAL, BSAA, BSAL, and NSAA. Table 14 compares the viscosity reduction of biosimilar ERBITUX® solutions using CSAA and CSAL to arginine or lysine alone.

TABLE 13

Viscosities of aqueous solutions of biosimilar ERBITUX® (222 ± 5 mg/mL, pH 7.0) with 0.25M viscosity-lowering agents at 25° C.

| Agent | Viscosity (cP) | Fold Reduction |
| --- | --- | --- |
| Phosphate Buffer | 1130 ± 7 | 1.0 |
| CSA Arginine | 52.5 ± 1.0 | 21.5 |
| CSA Lysine | 109 ± 1 | 10.4 |
| BSA Arginine | 53.4 ± 5.5 | 21.2 |
| BSA Lysine | 126 ± 1 | 9.0 |
| NSA Arginine | 69.4 ± 0.6 | 16.3 |

TABLE 14

Viscosities of aqueous solutions of biosimilar ERBITUX® (222 ± 5 mg/mL, pH 7.0) with 0.25M viscosity-lowering agents at 25° C.

| Agent | Viscosity (cP) | Fold Reduction |
| --- | --- | --- |
| Phosphate Buffer | 1130 ± 7 | 1.0 |
| CSAA | 52.5 ± 1.0 | 21.5 |
| CSA Sodium | 393 ± 14 | 2.9 |

TABLE 14-continued

Viscosities of aqueous solutions of biosimilar ERBITUX® (222 ± 5 mg/mL, pH 7.0) with 0.25M viscosity-lowering agents at 25° C.

| Agent | Viscosity (cP) | Fold Reduction |
| --- | --- | --- |
| Arginine HCl | 45.3 ± 0.5 | 24.9 |
| CSAL | 109 ± 1 | 10.4 |
| Lysine HCl | 128 ± 2 | 8.8 |

The data in Table 13 show a reduction in viscosity of at least 9.0-fold for all five viscosity-lowering agents compared to an aqueous solution of biosimilar ERBITUX® in phosphate buffer under otherwise the same conditions. The most efficacious viscosity-lowering agents, CSAA and BSAA, lowered the solution viscosity some 21-fold.

The viscosities of aqueous solutions of biosimilar ERBITUX® containing 0.25 M CSAA were compared as a function of pH at varying protein concentrations. FIG. 5 demonstrates that a viscosity minimum is observed around pH 7.0 for all protein concentrations. The effect of pH on viscosity is most pronounced for higher protein concentrations (253 mg/mL in the example).

As seen in Table 15, the aqueous solutions of biosimilar and branded ERBITUX® have similar viscosities in the presence of the arginine salt BSAA at 0.25 M.

TABLE 15

Viscosities of 224 ± 4 mg/mL aqueous solutions of biosimilar ERBITUX® or branded ERBITUX® with or without 0.25M BSAA at 25° C. and pH 7.0.

| Agent | Biosimilar ERBITUX® viscosity (cP) | Branded ERBITUX® viscosity (cP) |
| --- | --- | --- |
| Phosphate Buffer | 1130 ± 7 | 556 ± 20 |
| 0.25M BSAA | 53.4 ± 5.5 | 44.1 ± 0.5 |

The impact of the viscosity-lowering agents on the formation of irreversible protein aggregates was examined for biosimilar ERBITUX®. Aqueous liquid formulations were prepared of (i) biosimilar ERBITUX® and (ii) biosimilar ERBITUX® containing 0.25 M CSAL. These solutions were stored for 90 days at 4□C and pH 5.4 and 7.0, respectively. The stored samples were examined using size exclusion chromatography (column: Tosoh TSKgel UltraSW Aggregate; mobile phase: 0.1 M potassium phosphate/0.1 M sodium sulfate, pH 6.8 at 0.8 mL/min; injection: 20 µL of a 5 mg/mL mAb solution). The data in Table 16 reveal no significant aggregate formation in either the commercial drug product or high-concentration viscosity-lowered formulation.

TABLE 16

Percentage of protein aggregate formation after 90 days of storage at 4° C. as measured by size exclusion chromatography for aqueous solutions containing of biosimilar ERBITUX® with or without 0.25M CSAL.

| Sample | % Monomer | % Dimer | % Aggregate |
| --- | --- | --- | --- |
| Biosimilar ERBITUX® 5 mg/mL | 99.0 | 1.0 | 0.0 |
| Biosimilar ERBITUX® 210 mg/mL with 0.25M CSAL | 98.4 | 0.9 | 0.7 |

Example 9. The Effect of Viscosity-Lowering Agents on Aqueous Solutions of REMICADE®

Materials and Methods

Commercially-obtained REMICADE® containing pharmaceutical excipients (sucrose, Polysorbate 80, sodium phosphate buffer) was prepared as per instructions in the prescribing information sheet. Subsequently, the aqueous drug product was purified, buffer exchanged, concentrated, dried, reconstituted, and analyzed as described in Example 1 above (using the extinction coefficient of 1.4 L/g*cm at 280 nm). Viscosities were measured using either a RheoSense mVROC microfluidic viscometer equipped with an "A" or "B" chip.

Results

Figure 6A:
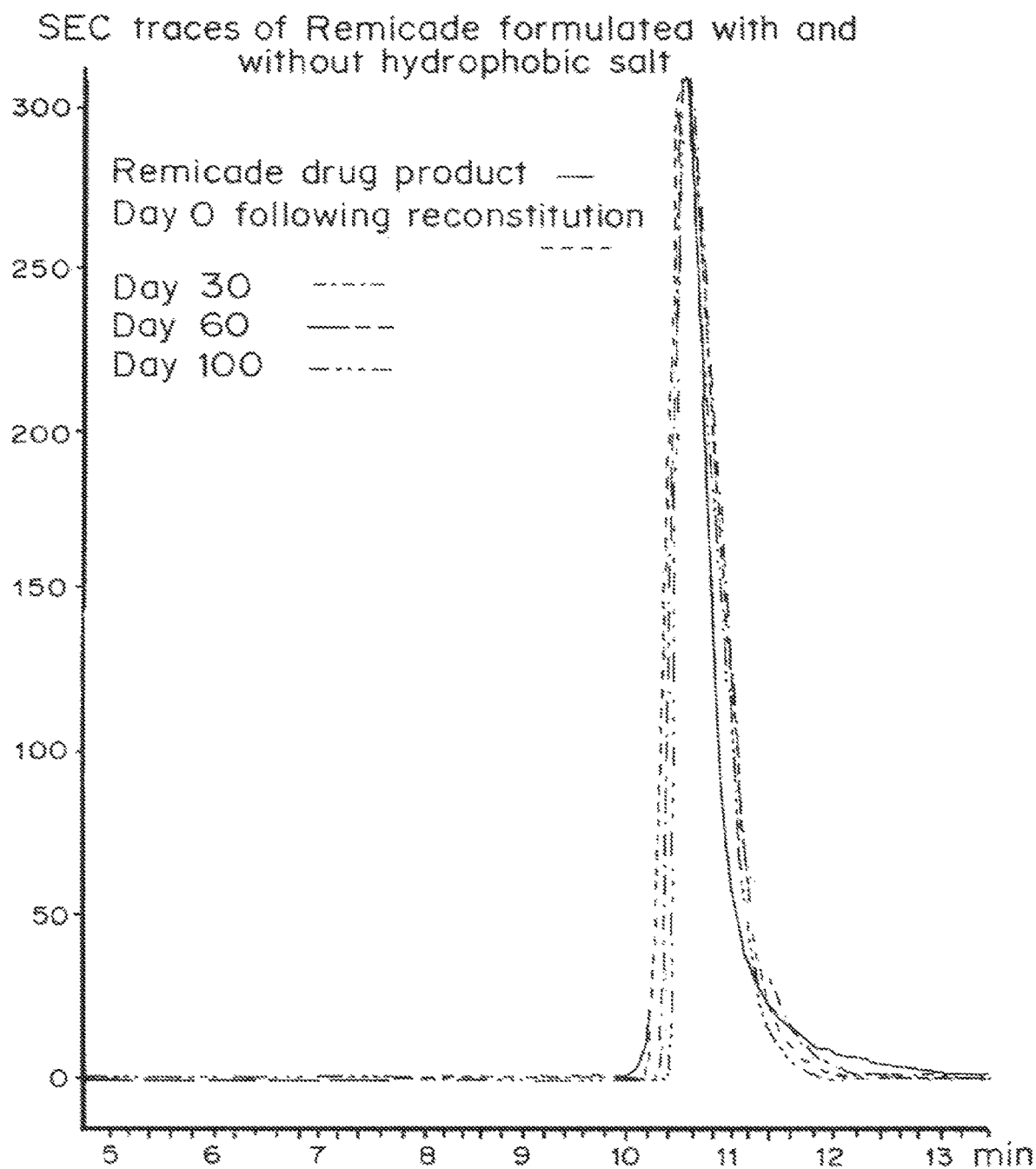
FIG. 6A and FIG. 6B are size-exclusion chromatography traces depicting absorbance intensity (at 280 nm) as a function of elution time (in minutes) for a 220 mg/mL aqueous solution of REMICADE® stored at 4° C. for up to 100 days, compared to freshly reconstituted commercial drug product.
Figure 6B:
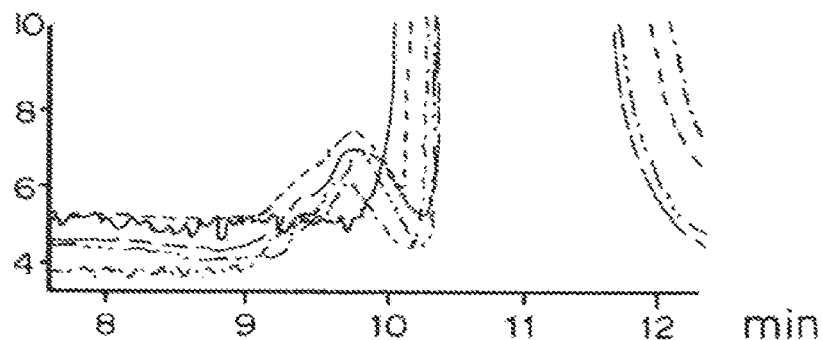

The data for aqueous REMICADE® solutions in Table 17 demonstrate that (i) viscosity-lowering agents containing a bulky cyclic group provide greater than 15-fold viscosity reductions, and (ii) CSAA, CSAAPMI, and sulfosalicylic acid diarginine (SSA DiArg) provide the greatest viscosity reduction of about 29-fold. Solution viscosities in the presence of ArgHCl alone are significantly higher than those with the bulky cyclic groups.

phate/0.1 M sodium sulfate buffer pH 6.8 at 0.8 mL/min; 20 µL injection of ~4.5 mg/mL solutions), is similar to the drug product at all time points and no detectable aggregation is observed after storage for 100 days at 4° C. The viscosity, as measured using a microfluidic viscometer, was demonstrated to remain stable after storage for 30 days at 4° C. (Table 20). Additionally, antigen binding of this processed REMICADE® protein was measured with a REMICADE®-specific ELISA assay and no decrease in binding was seen between days 0 and 100 (Table 20). Similarly, the monomer content (Table 21) and antigen binding (normalized to that of the drug product, Table 22) of concentrated solutions of REMICADE® in 0.25 M CSAA are comparable to the drug product after 1 week of storage at room temperature. Lastly, Table 23 demonstrates that storage of a lyophilized cake containing CSAA at 4° C. for 75 days has no negative effects on the solution viscosity or extent of protein aggregation when the sample is reconstituted. The results in Tables 19-23 and FIG. 6A and FIG. 6B demonstrate the biophysical stability of REMICADE® formulated with CSAA before and after storage for at least 100 days at 4° C.

TABLE 17

Viscosities of aqueous solutions of REMICADE ® containing 0.25M viscosity-lowering agents at 25° C. and pH 7.0.

| [REMICADE ®] (mg/mL) | Viscosity (cP) | | | | | | |
|---|---|---|---|---|---|---|---|
| | PB | ArgHCl | CSAA | CSA APMI | BSAA | CSAL | SSA DiArg |
| 222 ± 6 | 1557 ± 22 | 486 ± 34 | 53.7 ± 9.3 | 56.3 ± 2.7 | 92.3 ± 1.4 | 95.3 ± 1.1 | 55.9 ± 1.8 |
| 166 ± 4 | 513 ± 15 | 110 ± 1 | 19.1 ± 0.2 | 31.7 ± 0.3 | 26.7 ± 1.2 | 27.4 ± 0.2 | 27.1 ± 0.3 |

PB = phosphate buffer; ArgHCl = arginine HCl; CSAA = camphorsulfonic acid arginine; CSA APMI = camphorsulfonic acid 1-(3-aminopropyl)-2-methyl-1H-imidazole; BSAA = benzene sulfonic acid arginine; CSAL = camphorsulfonic acid lysine; SSA DiArg = sulfosalicylic acid di-arginine.

The dependence of the viscosity reduction on the agent concentration was examined for aqueous solutions of REMICADE® in the presence of CSAA. The results presented in Table 18 demonstrate that viscosity reduction increases with increasing agent concentration. The viscosity reduction, for example, is more than twice as large (the viscosity is less than half) with 0.35 M agent as compared to 0.20 M agent.

TABLE 18

Viscosity of an aqueous solution of REMICADE ® (215 ± 5 mg/mL) in the presence of various concentrations of CSAA measured at 25° C. and pH 7.0.

| [CSAA], (M) | Viscosity (cP) |
|---|---|
| 0 | 1557 ± 22 |
| 0.20 | 81.3 ± 1.0 |
| 0.25 | 53.7 ± 9.3 |
| 0.35 | 38.2 ± 0.9 |

Biophysical properties of solutions of REMICADE® formulated with 0.25 M CSAA were assessed over 90 days. Samples of REMICADE® formulated with 0.25 M CSAA were prepared as described in Example 1 above. As seen in Table 19 and FIG. 6A and FIG. 6B, the monomer content of concentrated solutions of REMICADE® in 0.25 M CSAA as determined by size exclusion chromatography (Tosoh TSK-gel UltraSW Aggregate column; 0.1 M potassium phos-

TABLE 19

No increased aggregation (compared to drug product) is observed in an aqueous solution of REMICADE ® (227 mg/mL, pH 7) after formulation with 0.25M CSAA and storage at 4° C.

| Day | % monomer |
|---|---|
| Drug Product | 99.9 ± 0.03 |
| 0 | 99.7 ± 0.07 |
| 30 | 99.7 ± 0.04 |
| 100 | 99.9 ± 0.1 |

TABLE 20

Reduced viscosity and antigen binding are retained over time in an aqueous solution of REMICADE ® (227 mg/mL, pH 7) after formulation with 0.25M CSAA and storage at 4° C.

| Day | Viscosity (cP) | % binding (ELISA) |
|---|---|---|
| 0 | 65.2 ± 0.7 | 105 ± 14 |
| 30 | 62.2 ± 1.4 | 98 ± 12 |
| 100 | n.d. | 101 ± 5 |

TABLE 21

No increased aggregation (compared to drug product) is observed in an aqueous solution of REMICADE ® (219 mg/mL, pH 7) after formulation with 0.25M CSAA and storage at room temperature.

| | % monomer | |
| --- | --- | --- |
| Day | Drug Product | 0.25M CSAA |
| 0 | 99.7 ± 0.1 | 99.9 ± 0.1 |
| 4 | 99.9 ± 0.1 | 97.9 ± 0 |
| 7 | 100 ± 0 | 100 ± 0 |

TABLE 22

Antigen binding persists in an aqueous solution of REMICADE ® (219 mg/mL, pH 7) after formulation with 0.25M CSAA and storage at room temperature.

| | % binding (normalized to drug product) | |
| --- | --- | --- |
| Day | Drug Product | 0.25M CSAA |
| 0 | 100 ± 12 | 88.6 ± 5.2 |
| 7 | 100 ± 28 | 114 ± 2.4 |

TABLE 23

REMICADE ® stored as a lyophilized powder retains low viscosity and monomer content upon reconstitution after storage at 4° C. for 75 days

| Storage time (days) | Viscosity, cP | % Monomer (SEC) |
| --- | --- | --- |
| 0 | 65.2 ± 0.7 | 99.7 ± 0.1 |
| 75 | 59.3 ± 1.0 | 98.9 ± 0.1 |

Example 10. The Effect of Viscosity-Lowering Agents on Aqueous Solutions of HERCEPTIN®

Materials and Methods

Commercially-obtained HERCEPTIN® containing pharmaceutical excipients (histidine buffer, trehalose, Polysorbate 20) was prepared as per instructions in the prescribing information sheet. Subsequently, the aqueous drug product was purified, buffer exchanged, concentrated, dried, reconstituted, and analyzed as described in Example 1 above (using the extinction coefficient of 1.5 L/g*cm at 280 nm). Viscosities were measured using a RheoSense mVROC microfluidic viscometer equipped with an "A" or "B" chip.

Results

The data presented in Table 24 show that the viscosity of an aqueous solution of HERCEPTIN® containing viscosity-lowering agents—compared to those containing PB—is lowest in the presence of CSAA. At higher protein concentrations (i.e. >250 mg/mL) Arginine HCl alone reduces viscosity significantly and CSA further enhances the effect.

TABLE 24

Viscosities of aqueous solutions of HERCEPTIN ® containing 0.25M salts at 25° C. and pH 7.0.

| [HERCEPTIN ®] | Viscosity (cP) | | | |
| --- | --- | --- | --- | --- |
| (mg/mL) | PB | ArgHCl | CSAA | BSAA |
| 270 ± 6 | 400 ± 4 | 179 ± 17 | 96.7 ± 4.7 | 115 ± 6 |
| 254 ± 3 | 172 ± 5 | 116 ± 24 | 78.0 ± 8.7 | 75.4 ±5.0 |
| 216 ± 0 | n.d. | 44.8 ± 1.1 | 55.7 ± 2.3 | n.d. |

PB = phosphate buffer;
ArgHCl = arginine HCl;
n.d. = not determined

Example 11. The Effect of Viscosity-Lowering Agents on Aqueous Solutions of TYSABRI®

Materials and Methods

Commercially-obtained TYSABRI® containing pharmaceutical excipients (sodium phosphate buffer, sodium chloride, Polysorbate 80) was purified, buffer exchanged, concentrated, dried, reconstituted, and analyzed as described in Example 1 above (using the extinction coefficient of 1.5 L/g*cm at 280 nm). Viscosities were measured using a RheoSense mVROC microfluidic viscometer equipped with an "A" or "B" chip.

Results

The data presented in Table 25 show that the viscosity reduction of an aqueous solution of TYSABRI® containing viscosity-lowering agents is approximately 2.5-fold (compared to solution containing PB) near 276 mg/mL protein.

TABLE 25

Viscosities of aqueous solutions of TYSABRI ® containing 0.25M viscosity-lowering agents at 25° C. and pH 7.0.

| [TYSABRI ®] | Viscosity (cP) | | | |
| --- | --- | --- | --- | --- |
| (mg/mL) | PB | ArgHCl | CSAA | BSAA |
| 276 ± 8 | 255 ± 5 | 97.2 ± 5.7 | 92.9 ± 2.6 | ad. |
| 237 ± 4 | 182 ± 6 | 52.3 ± 4.5 | 47.1 ± 2.1 | ad. |
| 230 ± 2 | n.d. | 37.0 ± 0.1 | n.d. | 34.9 ± 1.3 |

PB = phosphate buffer; ArgHCl = arginine HCl; n.d. = not determined.

Example 12. The Effect of Viscosity-Lowering Agents on Aqueous Solutions of Biosimilar RITUXAN®

Materials and Methods

Commercially-obtained biosimilar RITUXAN® containing pharmaceutical excipients (citrate buffer, sodium chloride, and TWEEN® 80) was purified, buffer exchanged, concentrated, dried, reconstituted, and analyzed as described in Example 1 above (using the extinction coefficient of 1.7 L/g*cm at 280 nm). Viscosities were measured using a RheoSense mVROC microfluidic viscometer equipped with an "A" or "B" chip.

Results

The data presented in Table 26 show that the viscosity reduction for an aqueous solution of biosimilar RITUXAN® containing viscosity-lowering agents is over 13-fold at approximately 213 mg/mL protein and over 5-fold at approximately 202 mg/mL, compared to the mAb formulated in PB.

TABLE 26

Viscosities of aqueous solutions of biosimilar RITUXAN ® with viscosity-lowering agents at 25° C. and pH 7.0.

| [RITUXAN ®] (mg/mL) | PB 0.25M | Arg HCl 0.25M | Arg HCl 0.45M | SSA diArg 0.25M | SSA diAPMI 0.25M | CSA Na 0.25M | CSAA 0.25M | CSA APMI 0.25M | CSA DMF 0.25M |
|---|---|---|---|---|---|---|---|---|---|
| 213 ± 4 | 636 ± 32 | 99.9 ± 5.0 | 86.8 ± 1.8* | 68.3 ± 0.8* | 46.6 ± 1.9 | 211 ± 2 | 103 ± 0 | 78.6 ± 2.0 | 161 ± 4 |
| 202 ± 2 | 251 ± 1 | n.d. | 46.9 ± 0.8 | 44.1 ± 0.1 | n.d. | 76.1 ± 1.3 | 78.4 ± 0.3 | 38.7 ± 0.7 | n.d. |

*[RITUXAN ®] is 220 mg/mL
DMP = dimethylpiperazine

Example 13. The Effect of Viscosity-Lowering Agents on Aqueous Solutions of VECTIBIX®

Materials and Methods

Commercially-obtained VECTIBIX® containing pharmaceutical excipients was purified, buffer exchanged, concentrated, dried, reconstituted, and analyzed as described in Example 1 above (using the extinction coefficient of 1.25 L/g*cm at 280 nm). Viscosities were measured using a RheoSense mVROC microfluidic viscometer equipped with an "A" or "B" chip.

Results

The data presented in Table 27 show that the viscosity reduction of an aqueous solution of VECTIBIX® containing viscosity-lowering agents is approximately 2-fold at 291 mg/mL and 3-fold at 252 mg/mL, compared to solutions with PB but no viscosity-lowering agents.

TABLE 27

Viscosities of aqueous solutions of VECTIBIX ® with 0.25M viscosity-lowering agents at 25° C. and pH 7.0.

| [VECTIBIX ®] (mg/mL) | Viscosity (cP) | | |
|---|---|---|---|
| | PB | ArgHCl | CSAA |
| 291 ± 3 | 328 ± 12 | n.d. | 162 ± 1 |
| 264 | ad | n.d. | 44.3 ± 2.3 |
| 252 ± 3 | 80.3 ± 3.3 | 36.2 ± 1.0 | 27.4 ± 1.2 |
| 233 ± 4 | 38.7 ± 1.8 | 24.7 ± 1.3 | 26.2 ± 6.5 |

Example 14. The Effect of Viscosity-Lowering Agents on Aqueous Solutions of ARZERRA®

Materials and Methods

Commercially-obtained ARZERRA® containing pharmaceutical excipients was purified, buffer exchanged, concentrated, dried, reconstituted, and analyzed as described in Example 1 above (using the extinction coefficient of 1.5 L/g*cm at 280 nm). Viscosities were measured using a RheoSense mVROC microfluidic viscometer equipped with an "A" or "B" chip.

Results

The data presented in Table 28 show that the viscosity reduction of an aqueous solution of ARZERRA® containing viscosity-lowering agents is approximately 3-fold at 274 mg/mL and 2-fold at 245 mg/mL, compared to solutions with PB but no viscosity-lowering agents.

TABLE 28

Viscosities of aqueous solutions of ARZERRA ® with 0.25M viscosity-lowering agents at 25° C. and pH 7.0.

| [ARZERRA ®] (mg/mL) | Viscosity (cP) | | |
|---|---|---|---|
| | PB | CSAA | CSAAPMI |
| 274 ± 10 | 349 ± 2 | 125 ± 7 | 98.9 ± 0.7 |
| 245 ± 4 | 120 ± 4 | n.d. | 53.6 ± 0.6 |

Example 15. Comparison of Different Methods for Measuring Viscosity

Materials and Methods

Aqueous solutions containing 220 mg/mL REMICADE® and 0.25 M CSAA were prepared as described above Example 1. The viscosities at 25° C. and pH 7.0 are reported in Table 29 as extrapolated zero-shear viscosities from cone and plate viscometer measurements and as absolute viscosities measured with a microfluidic viscometer. The cone and plate measurements used a DV2T cone and plate viscometer (Brookfield) equipped with a CPE40 or CPE52 spindle measured at multiple shear rates between 2 and 400 $s^{-1}$. An extrapolated zero-shear viscosity was determined from a plot of absolute viscosity versus shear rate. The microfluidic viscometer measurements were performed using a RheoSense mVROC microfluidic viscometer equipped with an "A" or "B" chip at multiple flow rates (approximately 20%, 40%, and 60% of the maximum pressure for each chip).

Results

The data in Table 29 demonstrates that the absolute viscosities from the microfluidic viscometer can be directly compared to the extrapolated zero-shear viscosities determined from the cone and plate viscometer.

TABLE 29

Viscosities of aqueous solutions of REMICADE ® (220 mg/mL) with 0.25M CSAA at 25° C. and pH 7.0 measured on two different viscometers.

| Instrument | Viscosity (cP) |
|---|---|
| Cone and plate viscometer (C&P) | 62.3 ± 0.1 |
| Microfluidic viscometer on a chip (mVROC) | 53.7 ± 9.3 |

In order to compare a broader range of viscosities and protein concentrations, aqueous solutions of a model antibody, bovine gamma globulin, were prepared with and without 0.25 M CSAL. The viscosities were measured as described above at protein concentrations ranging from 110 mg/mL to 310 mg/mL. The data presented in Table 30 demonstrates that the absolute viscosities from the microfluidic viscometer can be directly compared to the extrapolated zero-shear viscosities for both low and high viscosity protein solutions.

TABLE 30

Viscosities of aqueous gamma globulin solutions with and without 0.25M CSAL at 25° C. and pH 7.0 measured on two different viscometers.

| [gamma globulin] (mg/mL) | Viscosity (cP) | | | |
|---|---|---|---|---|
| | without CSAL | | With CSAL | |
| | C & P | microfluidic | C & P | microfluidic |
| 110 | 3.81 ± 0.19 | 2.66 ± 0.01 | n.d. | n.d. |
| 170 | 12.0 ± 0.6 | 11.0 ± 0.1 | 10.3 ± 1.0 | 10.6 ± 0.1 |
| 260 | 167 ± 1 | 161 ± 1 | 93.5 ± 1.2 | 85.3 ± 0.3 |
| 310 | 399 ± 1 | 377 ± 2 | 223 ± 1 | 203 ± 2 |

Example 16. Viscosity-Lowering Agents Show No Signs of Toxicity when Injected Subcutaneously Materials and Methods Thirty 11-week old Sprague-Dawley rats were separated into 6 groups of 5 rats each (3 saline control groups and 3 CSAA groups). The rats were injected subcutaneously with 0.5 mL of either endotoxin-free phosphate-buffered saline or endotoxin-free 0.25 M CSAA according to the following schedule: One group from each condition was injected once on day 1 and then sacrificed 1 hour later; one group from each condition was injected once on day 1 and once on day 2 and then sacrificed 24 hours after the second injection; and one group from each condition was injected once on day 1, once on day 2, and once on day 3, and then sacrificed 24 hours after the third injection.

Clinical observations were recorded for any pharmacotoxicological signs pre-dose, immediately post-dose, at 1 and 4 hours (±15 minutes) post-dose, and daily thereafter. Irritation, if any, at injection sites was scored using the Draize evaluation scores pre-dose, immediately post-dose, at 1 hour (±15 minutes) post dose, and prior to sacrifice.

Results

Overall, the observed consequences of the injections of saline and CSAA were macroscopically similar throughout the course of the study. Both induced from no irritation to slight irritation with edema scores of 0-2 at various time points. Microscopic examination of injection sites suggests a very minor, clinically insignificant, irritative effect with CSAA that was no longer evident by day 4.

Example 17. Concentrated Aqueous Solutions of REMICADE® Formulated with Viscosity-Lowering Agents Exhibit Low Syringe Extrusion Forces and High Monomer Content when Expelled Through Various Gauge Needles Materials and Methods Commercially-obtained REMICADE® containing pharmaceutical excipients (sucrose, Polysorbate 80, sodium phosphate buffer) was prepared per instructions in the prescribing information sheet. Subsequently, the aqueous drug product was purified, buffer exchanged, concentrated, dried, reconstituted, and analyzed as described in Example 1 above (using the extinction coefficient of 1.4 L/g*cm at 280 nm). 20 mM solutions of either phosphate buffer, CSAAPMI or CSAA were used for buffer exchange, and the lyophilized cakes were reconstituted to 0.25 M of each viscosity-lowering agent. Following reconstitution, the viscosity of each solution was measured using the microfluidic viscometer as described in previous examples. The solutions were then back-loaded into 1 mL BD insulin syringes with 27, 29, or 31 gauge fixed needles. The force required to extrude the concentrated REMICADE® solutions was then measured using an Instron at a rate of displacement equivalent to a fluid flow rate of 3 mL/min. The expelled solution was collected from the syringe and analyzed by size-exclusion chromatography.

Results

All REMICADE® solutions containing viscosity-lowering agents were able to be expelled through the syringes at relatively low extrusion forces (Table 31). The solution containing phosphate buffer could not be expelled due to high viscosity. Both solutions containing viscosity-lowering agents retained high monomer content post-extrusion regardless of needle gauge, as indicated in Table 31.

TABLE 31

Syringeability of concentrated aqueous solutions of REMICADE® extruded through various gauge needles.

| Agent | [REMICADE®] (mg/mL) (viscosity in cP) | Needle gauge | % Monomer | Syringe Force (N) |
|---|---|---|---|---|
| 0.25M Phosphate Buffer | 220 (1,500) | pre-syringe | 98.8 ± 0.0 | na |
| | | 27 | could not be | na |
| | | 29 | extruded | |
| | | 31 | | |
| 0.25M CSAAPMI | 230 (90.8 ± 8.4) | pre-syringe | 99.2 ± 0.32 | na |
| | | 27 | 99.1 ± 0.0 | 21.9 |
| | | 29 | 99.0 ± 0.0 | 30.4 |
| | | 31 | 99.0 ± 0.0 | 38.4 |
| 0.25M CSAA | 224 (60.9 ± 1.1) | pre-syringe | 99.7 ± 0.3 | na |
| | | 27 | 99.5 ± 0.1 | 18.4 |
| | | 29 | 99.4 ± 0.2 | 24.9 |
| | | 31 | 99.5 ± 0.2 | 33.0 |

Example 18: Viscosity-Lowering Agents Reduce the Viscosity of Concentrated Aqueous Solutions of Biosimilar AVASTIN®

Materials and Methods

A commercially-obtained biosimilar AVASTIN® containing pharmaceutical excipients (Polysorbate 20, phosphate and citrate buffers, mannitol, and NaCl) was purified. First, Polysorbate 20 was removed using DETERGENT-OUT® TWEEN Medi Columns (G-Biosciences). Next, the resulting solutions were extensively buffer-exchanged into 20 mM sodium phosphate buffer (PB) for PB samples and 2 mM PB for viscosity-lowering agent samples, and concentrated to a final volume of less than 10 mL on Jumbosep centrifugal concentrators (Pall Corp.). The viscosity-lowering agent was then added to the 2 mM PB samples as described in Example 4 above. The viscosity-lowering agent(s) were added in an amount sufficient to give concentration upon reconstitution as specified below. In cases of combinations of agents, the concentration of each component is 0.15 M. The protein solutions were then freeze-dried. The dried protein cakes were reconstituted in phosphate buffer (for PB samples) or water (for samples containing viscosity-lowering agents) to a final volume of approximately 0.10 mL. The final concentration of mAb in solution was determined by either a Coomassie protein quantification assay by comparing unknown concentrations of samples to a standard curve of biosimilar AVASTIN® or by A280 using the extinction coefficient of 1.7 L/g*cm, when possible. Viscosities reported were measured on a RheoSense mVROC microfluidic viscometer. Results are reported in Table 32.

Results

Many GRAS, JIG, and API compounds are capable of reducing the viscosity of concentrated biosimilar AVASTIN® solutions relative to phosphate-buffered samples. Of those compounds included in Table 32, local anesthetics such as procaine and lidocaine, as well as GRAS agents such as biotin are among the most efficacious viscosity reducing excipients.

TABLE 32

Effect of Viscosity-Lowering Agents on Solutions of Biosimilar AVASTIN ®.

| Agent | [Biosimilar AVASTIN ®], mg/ml | Viscosity, cP |
| --- | --- | --- |
| 0.25M Phosphate Buffer | 235 | 397 ± 2 |
|  | 220 | 213 ± 10 |
|  | 200 | 96.8 ± 0.9 |
| CSA-1-o-tolybiguanide | 228 | 121 ± 1 |
| HEPES-Tris | 214 | 90.5 ± 1.8 |
| CSA-Na-Creatinine | 202 | 38.4 ± 0.9 |
| CSA-Na-aminocyclohexane carboxylic acid | 182 | 51.4 ± 0.1 |
|  | 225 | 69.2 ± 3.7 |
| Ethane disulfonate-diTris-2Na | 219 | >150 |
| CSA-piperazine† | 212 ± 0 | 64.5 ± 13.1 |
| Sulfacetamide-Na | 214 | 113 ± 1 |
| Trimetaphosphate-3Na | 211 | 121 ± 6 |
| CSA-Tris | 206 | 64.4 ± 1.4 |
|  | 197 | 50 ± 1 |
| Creatinine (0.6M) | 243 | 50.8 ± 0.5 |
| Creatinine (0.3M) | 192 | 24.5 ± 0.7 |
| Creatinine | 232 | 72.7 ± 0.8 |
|  | 218 | 53.4 ± 1.0 |
|  | 194 | 36.1 ± 0.2 |
| Lactobionic acid-Tris | 219 | 109 ± 5 |
| CSA-4-amino pyridine | 229 | 86.4 ± 1.1 |
| Sucralose | 230 | 147 ± 4 |
| Quaternium 15 | 232 | 172 ± 4 |
| Glucuronic acid-Tris | 221 | 151 ± 5.0 |
| Biotin-Na | 189 | 45.1 ± 0.9 |
|  | 213 | 60.7 ± 0.6 |
| Procaine HCl | 188 | 40.8 ± 0.9 |
|  | 222 | 65.8 ± 0.8 |
| Lidocaine HCl | 237 | 97.3 ± 1.8 |
| N-(4-Pyridiyl)pyridinium Cl HCl | 221 | 68.5 ± 1.1 |
| Creatinine Thiamine HCl | 228 | 59.6 ± 0.5 |
| Pyridoxine | 227 | 107 ± 0 |
| Riboflavin-5-phosphate | 225 | 131 ± 4 |
| CSA Triethanolamine | 238 | 144 ± 1 |
| Lidocaine HCl | 218 | 147 ± 15 |
| Chloroquine Phosphate (0.10M) | 200 | 27.9 ± 0.6 |
|  | 219 | 58.6 ± 1.6 |
|  | 228 | 71.8 ± 0.9 |
| Scopolamine HBr | 210 | 35.3 ± 1.1 |
|  | 223 | 64.0 ± 0.8 |
|  | 238 | 87.8 ± 1.5 |
| Levetiracetam | 195 | 31.8 ± 0.3 |
|  | 192 | 37.1 ± 1.3 |
|  | 215 | 85.5 ± 3.7 |
| Cimetidine HCl | 203 | 53.8 ± 2.4 |
| Metoclopramide HCl | 230 | 64.4 ± 1.6 |
| Sumatriptan Succinate (0.25M) | 212 | 93.2 ± 2.7 |
| Phenylephrine HCl | 201 | 108 ± 1 |
| Cidofovir hydrate (0.02M) | 210 | 121 ± 2 |
| Mepivacaine HCl | 223 | 129 ± 3 |
| Clindamycin Phosphate | 200 | 164 ± 17 |
| Piperacillin sodium salt | 206 | 197 ± 5 |
| Colistin sulfate salt | 240 | 261 ± 58 |
| Ceftriaxone sodium salt | 198 | 301 ± 5 |

TABLE 32-continued

Effect of Viscosity-Lowering Agents on Solutions of Biosimilar AVASTIN ®.

| Agent | [Biosimilar AVASTIN ®], mg/ml | Viscosity, cP |
| --- | --- | --- |
| Cefazolin | 229 | 60.6 ± 1 |
| Granisetron HCl | 168 | 37.9 ± 0.6 |
|  | 237 | 308 ± 34 |

†Average of two biological replicates
CSA = camphorsulfonic acid.

Example 19. Viscosity Reduction is an Agent-Concentration-Dependent Effect

Materials and Methods

Aqueous solutions of a commercially-obtained biosimilar AVASTIN® were prepared as described in Example 4. The dried protein cakes were reconstituted in phosphate buffer or water to a final volume of about 0.10 mL and a final 1-(3-aminopropyl)-2-methyl-1H-imidazole dihydrochloride (APMI*2HCl) concentration of either 0.10 or 0.25 M. The final concentration of mAb in solution was determined by a Coomassie protein quantification assay by comparing unknown concentrations of samples to a standard curve of biosimilar AVASTIN®. Viscosities reported were measured on a RheoSense mVROC microfluidic viscometer.

Results

Figure 7:
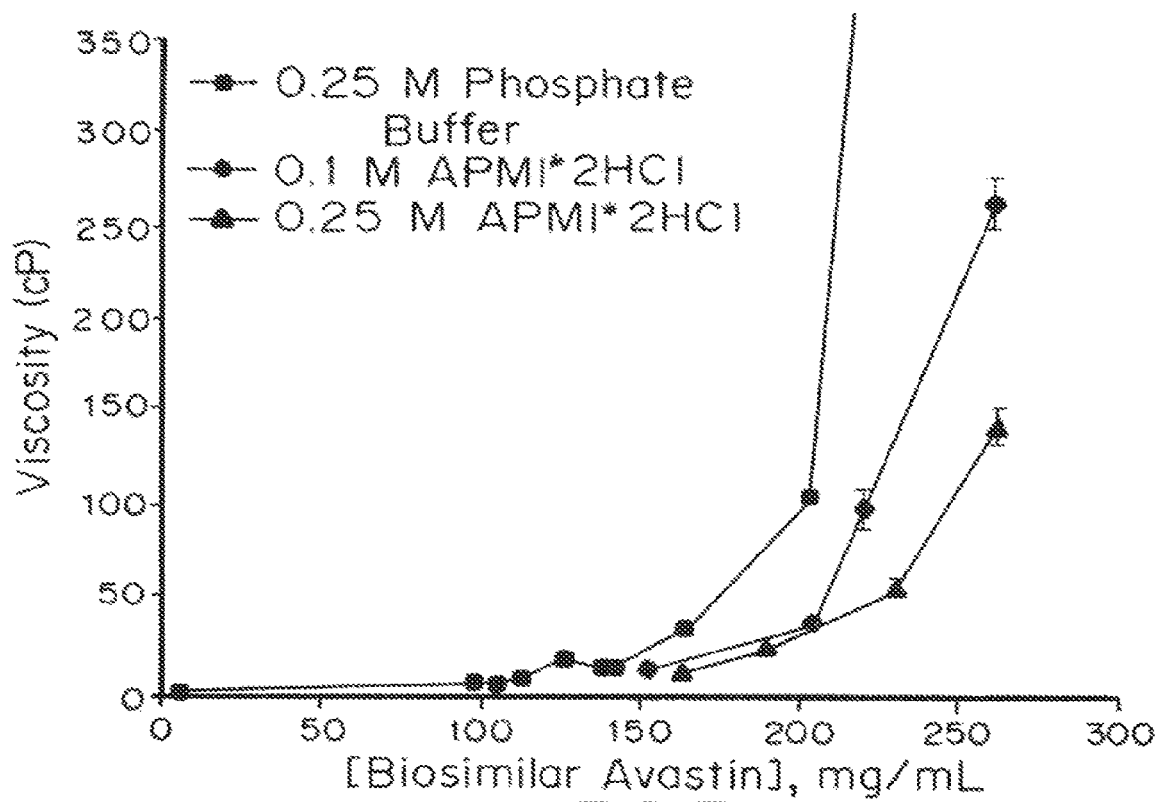
FIG. 7 depicts the viscosity (cP) as a function of protein concentration (mg/mL) of aqueous solutions of biosimilar bevacizumab (AVASTIN®) in 0.25 M phosphate buffer, 0.10 M or 0.25 M APMI*2HCl ((1-(3-aminopropyl)-2-methyl-1H-imidazole bis-HCl).

As depicted in FIG. 7, viscosity-lowering effect was increased as the concentration of APMI*2HCl was increased.

Example 20. A Single Viscosity-Lowering Agent Lowers the Viscosity of Many Therapeutically Relevant Monoclonal Antibodies Materials and Methods Aqueous solutions of a commercially-obtained biosimilar AVASTIN® were prepared as described in Example 4. The dried protein cakes were reconstituted in phosphate buffer or water to a final volume of about 0.10 mL and a final thiamine HCl concentration of 0.10 or 0.25 M. The final concentration of mAb in solution was determined by a Coomassie protein quantification assay by comparing unknown concentrations of samples to a standard curve of biosimilar AVASTIN®.

Commercially-obtained TYSABRI® containing pharmaceutical excipients (sodium phosphate buffer, NaCl, Polysorbate 80) was purified, buffer exchanged, concentrated, dried, reconstituted, and analyzed in the same manner. Commercially-obtained HERCEPTIN® containing pharmaceutical excipients (sodium phosphate buffer, NaCl, Polysorbate 80) was purified, buffer exchanged, concentrated, dried, reconstituted, and analyzed in the same manner. Commercially obtained biosimilar ERBITUX® containing pharmaceutical excipients (Polysorbate 80, phosphate buffer, and NaCl) was purified, buffer exchanged, concentrated, dried, reconstituted and analyzed in the same manner. Commercially-obtained REMICADE® containing pharmaceutical excipients (sucrose, Polysorbate 80, sodium phosphate buffer) was prepared as per instructions in the prescribing information sheet. Subsequently, the aqueous drug product was purified, buffer exchanged, concentrated, dried, reconstituted, and analyzed as described in the same manner. Viscosities reported were measured on a RheoSense mVROC microfluidic viscometer.

Results

The data in Table 33 demonstrate that thiamine HCl can lower the viscosity of concentrated aqueous solutions of many therapeutically relevant mAbs. Thiamine HCl can produce a greater than 4-fold viscosity reduction for each mAb.

TABLE 33

Effect of Thiamine HCl on Solution Viscosity.

| mAb | Agent | [Excipient], M | [Protein], mg/mL | Viscosity, cP |
|---|---|---|---|---|
| Biosimilar AVASTIN ® | PB | 0.25 | 220 | 213 ± 10 |
|  |  |  | 195 | 96.8 ± 0.9 |
|  | Thiamine HCl | 0.25 | 225 | 53.3 ± 6.8 |
|  |  | 0.1 | 190 | 31.5 ± 1.7 |
| TYSABRI ® | PB | 0.25 | 237 | 182 ± 6 |
|  | Thiamine HCl | 0.1 | 244 | 43.4 ± 0.7 |
| HERCEPTIN ® | PB | 0.25 | 253 | 172 ± 4 |
|  | Thiamine HCl | 0.1 | 218 | 41.6 ± 0.5 |
| Biosimilar ERBITUX ® | PB | 0.25 | 235 | 1370 ± 3 |
|  | Thiamine HCl | 0.15 | 245 | 29.5 ± 0.9 |
| REMICADE ® | PB | 0.25 | 176 | 432 ± 30 |
|  | Thiamine HCl | 0.15 | 178 | 40.7 ± 0.3 |

Examples 21-24. Viscosity-Lowering Agents Reduce the Viscosity of Aqueous Solutions of Many Therapeutically Relevant Monoclonal Antibodies Materials and Methods Aqueous solutions of commercially-obtained biosimilar RITUXAN®, TYSABRI®, HERCEPTIN®, biosimilar ERBITUX®, and REMICADE® were prepared as described in Examples 18 and 19. Tables 34-38 demonstrate that viscosity-lowering agents can be advantageously employed for many different monoclonal antibodies.

Results

TABLE 34

Viscosities of Aqueous Solutions of Biosimilar RITUXAN ® in the Presence of 0.15M Viscosity-Lowering Agents

| Agent | [biosimilar RITUXAN ®], mg/ml | Viscosity, cP |
|---|---|---|
| 0.25M Phosphate Buffer | 240 | 1270 ± 153 |
|  | 215 | 636 ± 32 |
|  | 199 | 251 ± 1 |
| CSA-1-o-tolybiguanide | 190 | 40.4 ± 1.9 |
| HEPES- Tris | 191 | 50.0 ± 3.8 |
| CSA-Na-Creatinine (0.3M) | 190 | 33.3 ± 1.1 |
| CSA-Na-aminocyclohexane carboxylic acid | 191 | 61.3 ± 2.5 |
| Ethane disulfonate- diTris-2Na | 191 | 80.3 ± 16.0 |
| CSA-piperazine | 191 | 57.5 ± 0.4 |
| Sulfacetamide-Na | 181 | 64.1 ± 1.6 |
| Trimetaphosphate-3Na | 199 | 126 ± 3.3 |
| CSA-Tris | 191 | 59.1 ± 0.7 |
| Creatinine (0.6M) | 197 | 28.4 ± 0.2 |
| Creatinine | 203 | 71.8 ± 0.8 |
| Lactobionic acid-Tris | 211 | 130 ± 1 |
| CSA-4-amino pyridine | 233 | 66.5 ± 0.8 |
|  | 195 | 47.0 ± 1.4 |
| Sucralose | 234 | 111 ± 8 |
| Quaternium 15 | 221 | 135 ± 5 |

TABLE 34-continued

Viscosities of Aqueous Solutions of Biosimilar RITUXAN ® in the Presence of 0.15M Viscosity-Lowering Agents

| Agent | [biosimilar RITUXAN ®], mg/ml | Viscosity, cP |
|---|---|---|
| Glucuronic acid-Tris | 207 | 149 ± 13 |
| CSA-Na-Ornidazole | 242 | 63.0 ± 3.5 |
|  | 188 | 40.7 ± 0.5 |
| Biotin-Na† | 191 ± 3 | 96.8 ± 12.2 |
| Procaine HCl | 222 | 46.2 ± 1.1 |
|  | 195 | 33.4 ± 1.2 |
| Metoclopramide HCl | 194 | 39.3 ± 0.4 |
| Scopolamine HBr | 197 | 42.3 ± 1.0 |
| Mepivacaine HCl | 185 | 46.8 ± 0.6 |
| Cimetidine HCl | 215 | 49.5 ± 1.2 |
| Granisetron HCl | 204 | 51.2 ± 0.8 |
| Phenylephrine HCl | 193 | 57.1 ± 2.8 |
| Chloroquine Phosphate (0.10M) | 210 | 67.1 ± 1.1 |
| Penicillin G sodium salt | 207 | 114 ± 7 |
| Piperacillin sodium salt | 194 | 127 ± 2 |
| Levetiracetam | 205 | 130 ± 2 |
| Moxifloxacin HCl | 193 | 152 ± 8 |
| Ceftriaxone sodium salt | 222 | 198 ± 17 |
| Clindamycin Phosphate | 203 | 199 ± 8 |
| Colistin sulfate salt | 230 | 228 ± 19 |
| Cefazolin | 206 | 65.1 ± 1.8 |

†Average of two biological replicates

TABLE 35

Viscosities of Aqueous Solutions of TYSABRI ® in the Presence of 0.15M Viscosity-Lowering Agents (Unless Otherwise Indicated).

| Agent | [TYSABRI ®], mg/mL | Viscosity, cP |
|---|---|---|
| PB | 310 | 715 ± 106 |
|  | 278 | 255 ± 5 |
|  | 237 | 182 ± 6 |
| Creatinine (0.30M) | 219 | 40.8 ± 1.8 |
| Procaine HCl | 228 | 45.1 ± 1.5 |
| Biotin Na | 233 | 75.8 ± 0.4 |
| Thiamine HCl (0.10M) | 244 | 43.4 ± 0.7 |

TABLE 36

Viscosities of Aqueous Solutions of HERCEPTIN ® in the Presence of 0.15M Viscosity-Lowering Agents (Unless Otherwise Indicated).

| Agent | [HERCEPTIN ®], mg/mL | Viscosity, cP |
|---|---|---|
| PB | 272 | 400 ± 4 |
|  | 253 | 172 ± 5 |
|  | 239 | 122 ± 17 |
|  | 218 | 71.6 ± 3.9 |
| Creatinine (0.3M) | 222 | 45.7 ± 0.3 |
| Procaine HCl | 222 | 41.8 ± 0.6 |
| CSA piperazine | 236 | 50.3 ± 0.6 |
| CSA-Na Ornidazole | 232 | 60.1 ± 0.6 |
| Biotin-Na | 230 | 69.9 ± 2.3 |
| Thiamine HCl (0.10M) | 245 | 41.5 ± 0.5 |

TABLE 37

Viscosities of Aqueous Solutions of ERBITUX ® in the Presence of 0.15M Viscosity-Lowering Agents (Unless Otherwise Indicated).

| Agent | [ERBITUX ®], mg/mL | Viscosity, cP |
|---|---|---|
| PB | 235 | 1370 ± 3 |
|  | 228 | 1130 ± 7 |
| Creatinine (0.30M) | 240 | 131 ± 4 |
| Procaine HCl | 230 | 35.9 ± 0.3 |
| Lidocaine HCl | 223 | 33.8 ± 0.4 |
| Nicotinamide | 232 | 292 ± 10 |
| Riboflavin-5-Phosphate (0.10M) | 237 | 492 ± 9 |
| Cimetidine HCl | 183 | 19.7 ± 0.2 |
| Metoclopramide HCl | 172 | 23.0 ± 0.2 |
| Granisetron HCl | 180 | 23.0 ± 0.2 |
| Scopolamine HBr | 173 | 23.4 ± 0.6 |
| Mepivacaine HCl | 182 | 27.8 ± 0.2 |
| Clindamycin Phosphate | 209 | 36.5 ± 0.0 |
| Chloroquine Phosphate (0.10M) | 179 | 37.4 ± 0.9 |
|  | 199 | 54.8 ± 0.2 |
| Phenylephrine HCl | 183 | 54.1 ± 2.9 |
| Moxifloxacin HCl | 186 | 66.7 ± 1.0 |
| Piperacillin sodium salt | 182 | 75.3 ± 1.6 |
| Penicillin G sodium salt | 178 | 82.1 ± 3.6 |
| Levetiracetam | 176 | 103 ± 3 |
|  | 199 | 178 ± 2 |
| Fosphenytoin disodium salt | 188 | 119 ± 2 |
| Ceftriaxone sodium salt | 190 | 120 ± 2 |
| Colistin sulfate salt | 203 | 138 ± 4 |
| Cefoxitin sodium salt | 194 | 166 ± 8 |
| Aztreonam (0.02M) | 179 | 256 ± 4 |
| Cidofovir hydrate (0.02M) | 189 | 284 ± 5 |

TABLE 38

Viscosities of Aqueous Solutions of REMICADE ® in the Presence of 0.15M Viscosity-Lowering Agents (Unless Otherwise Indicated).

| Agent | [REMICADE ®], mg/mL | Viscosity, cP |
|---|---|---|
| PB | 176 | 432 ± 30 |
| Creatinine | 144 | 37.1 ± 0.5 |
| Procaine HCl | 174 | 23.4 ± 0.2 |
| Thiamine HCl | 178 | 40.7 ± 0.3 |

Example 25. Viscosity-Lowering Effect of TPP and TPPAPMI, as a Function of Concentration of Biosimilar AVASTIN®

Aqueous solutions of a commercially-obtained biosimilar AVASTIN® were prepared as described in Example 1 above. The protein was formulated to contain either 0.25 M phosphate buffer, 0.10 M thiamine pyrophosphate (TPP), or 0.10 M TPP-1-(3-aminopropyl)-2-methyl-1H-imidazole (TPPAPMI).

Figure 8:
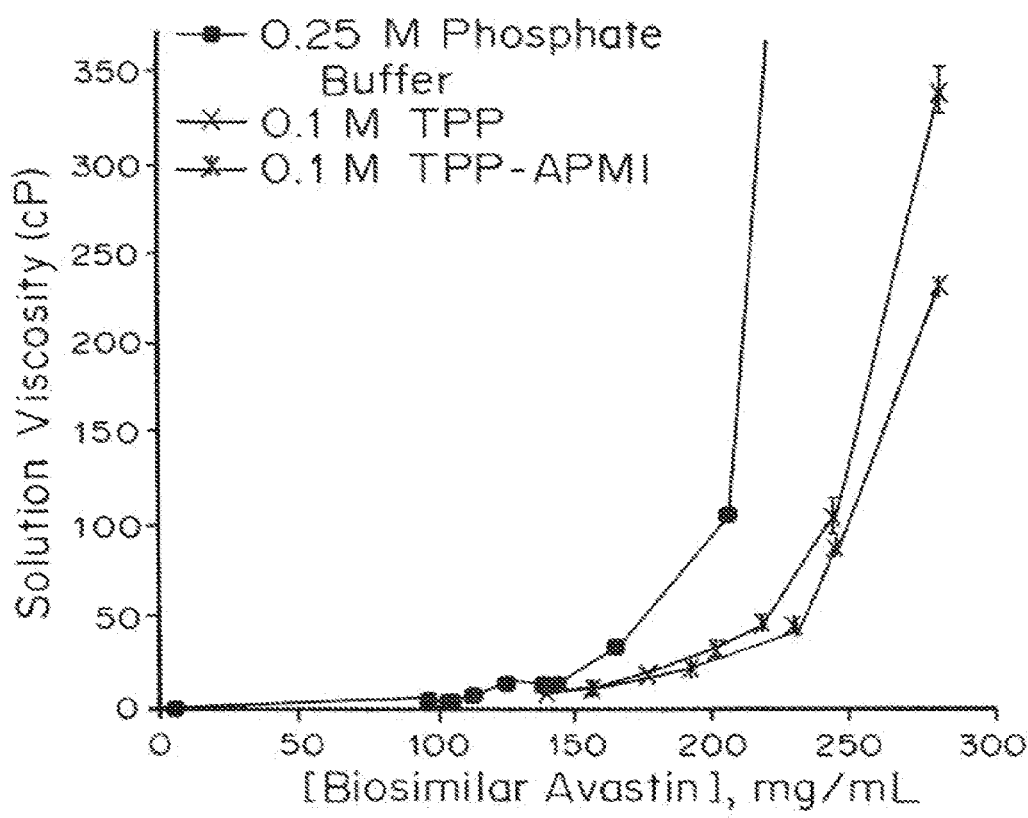
FIG. 8 depicts the viscosity (cP) as a function of protein concentration (mg/mL) of aqueous solutions of biosimilar bevacizumab (AVASTIN®) in 0.25 M phosphate buffer, 0.10 M thiamine pyrophosphate (TPP), or 0.10 M TPP1-(3-aminopropyl)-2-methyl-1H-imidazole (APMI).

FIG. 8 depicts the viscosity of aqueous biosimilar AVASTIN® solutions as a function of mAb concentration with either phosphate buffer, TPP, or TPPAPMI. The viscosity of biosimilar AVASTIN® in phosphate buffer increases exponentially within the tested protein concentration range. In the presence of TPP-containing excipients, the increase in viscosity is attenuated i.e. the viscosity gradient is reduced.

Example 26: Viscosity-Reducing Effect of a Viscosity-Lowering Agent, Thiamine HCl, as a Function of Concentration of Biosimilar SIMPONI ARIA®

Materials and Methods

SIMPONI ARIA® obtained commercially and containing pharmaceutical excipients (Histidine, Sorbitol, Polysorbate 80) was purified, buffer exchanged, concentrated, dried, reconstituted, and analyzed as described in Example 1 above (using the extinction coefficient of 1.4 L/g·cm at 280 nm). The protein was formulated to contain either 0.15 M phosphate buffer or 0.15 M thiamine HCl.

Results

Figure 9:
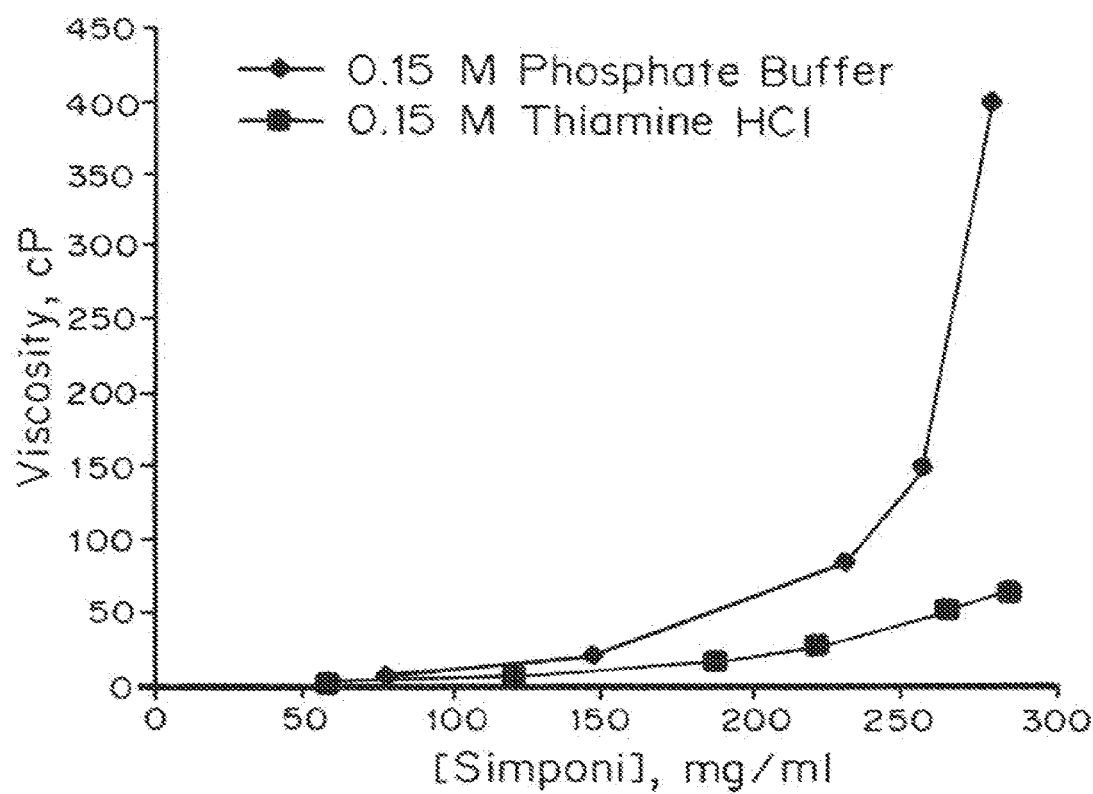
FIG. 9 depicts the viscosity (cP) of aqueous solutions of golimumab (SIMPONI ARIA®) as a function of protein concentration (mg/mL) with 0.15 M phosphate buffer or 0.15 M thiamine HCl.

FIG. 9 depicts the viscosity of aqueous SIMPONI ARIA® solutions as a function of mAb concentration with either phosphate buffer or thiamine HCl. The viscosity of SIMPONI ARIA® in phosphate buffer increases exponentially within the tested protein concentration range. In the presence of thiamine HCl, the increase in viscosity is attenuated i.e. the viscosity gradient is reduced.

Example 27. Viscosity-Lowering Effect of Thiamine HCl, as a Function of Concentration of ENBREL®

Materials and Methods

ENBREL® obtained commercially and containing pharmaceutical excipients (Mannitol, Sucrose, Tromethamine) was purified, buffer exchanged, concentrated, dried, reconstituted, and analyzed as described in Example 1 above (using the extinction coefficient of 0.96 L/g·cm at 280 nm). The protein was formulated to contain either 0.15 M phosphate buffer or 0.15 M Thiamine HCl.

Results

Table 39 depicts the viscosity of aqueous ENBREL® solutions with either phosphate buffer or thiamine HCl. The addition of thiamine HCl reduces the viscosity of ENBREL® up to about 2-fold.

TABLE 39

Viscosities of Aqueous Solutions of ENBREL ® in the Presence of 0.15M PB or Thiamin HCl

| [ENBREL], mg/mL | 0.15M PB | 0.15M Thiamin HCl |
|---|---|---|
| 271 ± 0 | 1120 ± 26 | 626 ± 32 |
| 250 ± 3 | 439 ± 11 | 305 ± 7 |
| 212 ± 7 | 316 ± 11 | 141 ± 3 |

Example 28. Isotonic Solutions of Viscosity-Lowering Excipients Reduce the Viscosity of Concentrated Solutions of REMICADE®

Materials and Methods

Commercially-obtained REMICADE® containing pharmaceutical excipients (sucrose, Polysorbate 80, sodium phosphate buffer) was prepared as per instructions in the prescribing information sheet. Subsequently, the aqueous drug product was purified, buffer exchanged, concentrated, dried, reconstituted, and analyzed as described in Example 1, except that isotonic amounts of charged hydrophobic compounds were added.

Results

As demonstrated in Table 40, isotonic amounts of both CSAA and CSAAPMI are capable of substantially reducing the viscosity of concentrated solutions of REMICADE®, in some cases by up to about 10-fold.

TABLE 40

Viscosities of solutions of REMICADE ® in the presence of isotonic (0.3 molal) viscosity-lowering excipients

| Salt | [REMICADE ®] (mg/mL) | Viscosity (cP) |
| --- | --- | --- |
| PB | 171 | 432 ± 30 |
| CSAAPMI | 167 | 41.4 ± 0.7 |
| PB | 131 | 175 ± 15 |
| CSAAPMI | 124 | 16.4 ± 1.2 |
| CSAA | 128 | 25.8 ± 0.8 |

Unless expressly defined otherwise above, all technical and scientific terms used herein have the same meanings as commonly understood by one of skill in the art. Those skilled in the art will recognize, or will be able to ascertain using no more than routine experimentation, many equivalents to the specific embodiments of the invention described herein. Such equivalents are intended to be encompassed by the following claims.

What is claimed:

1. A liquid composition comprising:
  (i) from about 100 mg/ml to about 300 mg/ml of an antibody;
  (ii) from about 0.10 M to about 0.25 M thiamine or a pharmaceutically acceptable salt thereof; and
  (iii) a pharmaceutically acceptable solvent;
  wherein the composition, when in a volume suitable for subcutaneous or intramuscular injection, has an absolute viscosity from about 1 cP to about 100 cP at 25° C. as measured using a cone and plate viscometer or a microfluidic viscometer, and wherein the absolute viscosity of the composition is less than an absolute viscosity of a control composition, the control composition comprising the antibody and the pharmaceutically acceptable solvent but without the thiamine or pharmaceutically acceptable salt thereof.

2. The liquid composition of claim 1, wherein the antibody is a monoclonal antibody.

3. The liquid composition of claim 1, wherein the solvent is aqueous.

4. The liquid composition of claim 1, wherein the antibody has a molecular weight of from about 120 kDa to about 250 kDa.

5. The liquid composition of claim 1, further comprising one or more pharmaceutically acceptable excipients, the pharmaceutically acceptable excipients comprising a sugar, sugar alcohol, buffering agent, preservative, carrier, antioxidant, chelating agent, natural polymer, synthetic polymer, cryoprotectant, lyoprotectant, surfactant, bulking agent, stabilizing agent, or any combination thereof.

6. The liquid composition of claim 5, wherein the one or more pharmaceutically acceptable excipients comprise a polysorbate, poloxamer 188, sodium lauryl sulfate, a polyol, poly(ethylene glycol), glycerol, propylene glycol, or a poly(vinyl alcohol).

7. The liquid composition of claim 5, wherein the sugar alcohol is sorbitol or mannitol.

8. The liquid composition of claim 1 in a unit-dose vial, multi-dose vial, cartridge, or pre-filled syringe.

9. The liquid composition of claim 1, wherein the composition is isotonic to human blood serum.

10. The liquid composition of claim 1, wherein the absolute viscosity is measured at a shear rate of at least about $0.5 \text{ s}^{-1}$ when measured using a cone and plate viscometer or a shear rate of at least about $1.0 \text{ s}^{-1}$ when measured using a microfluidic viscometer.

11. The liquid composition of claim 1, wherein the liquid composition is reconstituted from a lyophilized composition.

12. A lyophilized composition comprising:
  (i) an antibody and
  (ii) thiamine or a pharmaceutically acceptable salt thereof;
  wherein the lyophilized composition is reconstitutable to have from about 100 mg/ml to about 300 mg/ml of the antibody, from about 0.1 M to about 0.25 M of thiamine, and an absolute viscosity of from about 1 cP to about 100 cP at 25° C. as measured using a cone and plate viscometer or a microfluidic viscometer, wherein the absolute viscosity is an extrapolated zero-shear viscosity.

13. The lyophilized composition of claim 12, further comprising one or more pharmaceutically acceptable excipients, the pharmaceutically acceptable excipients comprising a sugar, sugar alcohol, buffering agent, preservative, carrier, antioxidant, chelating agent, natural polymer, synthetic polymer, cryoprotectant, lyoprotectant, surfactant, bulking agent, stabilizing agent, or any combination thereof.

14. A method of administering a therapeutically effective amount of an antibody to a subject, the method comprising subcutaneously or intramuscularly injecting the composition of claim 1 into the subject.

15. The method of claim 14, wherein the composition has a volume equal to or less than about 1.5 mL for the subcutaneous injecting, or equal to or less than about 3 mL for the intramuscular injecting.

16. The method of claim 14, wherein the injecting is performed with a heated syringe, a self-mixing syringe, an auto-injector, a pre-filled syringe, or a combination thereof.

17. The method of claim 14, wherein the injecting produces a primary irritation index of less than 3 when evaluated using a Draize scoring system.

18. The method of claim 14, wherein the injecting has an injection force that is at least 20% less than an injection force for a control composition, the control composition comprising the antibody and the pharmaceutically acceptable solvent, but without the thiamine, wherein the control composition is administered in the same way as the composition.

19. The method of claim 18, wherein the injecting is performed with a needle that is between 27 and 31 gauge in diameter.

20. The method of claim 19, wherein the injecting has an injection force of less than 30 N with a 27 gauge needle.

* * * * *